United States Patent
Cho et al.

(10) Patent No.: US 11,464,771 B2
(45) Date of Patent: *Oct. 11, 2022

(54) BROMODOMAIN AND EXTRA-TERMINAL PROTEIN INHIBITOR COMBINATION THERAPY

(71) Applicant: CELGENE QUANTICEL RESEARCH, INC., San Diego, CA (US)

(72) Inventors: Robert Cho, Sunnyvale, CA (US); Jeffrey Alan Stafford, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/033,311

(22) Filed: Sep. 25, 2020

(65) Prior Publication Data
US 2021/0008056 A1 Jan. 14, 2021

Related U.S. Application Data

(60) Continuation of application No. 16/750,996, filed on Jan. 23, 2020, now Pat. No. 10,881,655, which is a division of application No. 16/191,319, filed on Nov. 14, 2018, now Pat. No. 10,576,075, which is a continuation of application No. 15/796,571, filed on Oct. 27, 2017, now Pat. No. 10,166,227.

(60) Provisional application No. 62/413,763, filed on Oct. 27, 2016, provisional application No. 62/560,840, filed on Sep. 20, 2017.

(51) Int. Cl.
| | |
|---|---|
| A61K 31/472 | (2006.01) |
| A61P 35/00 | (2006.01) |
| A61K 31/337 | (2006.01) |
| A61K 31/495 | (2006.01) |
| A61K 38/15 | (2006.01) |
| A61K 45/06 | (2006.01) |

(52) U.S. Cl.
CPC .......... *A61K 31/472* (2013.01); *A61K 31/337* (2013.01); *A61K 31/495* (2013.01); *A61K 38/15* (2013.01); *A61K 45/06* (2013.01); *A61P 35/00* (2018.01); *A61K 2300/00* (2013.01)

(58) Field of Classification Search
CPC .............................. A61K 31/472; A61P 35/00
USPC ......................................................... 514/309
See application file for complete search history.

(56) References Cited

U.S. PATENT DOCUMENTS

| | | | |
|---|---|---|---|
| 8,980,879 B2 | 3/2015 | Liu et al. | |
| 9,034,900 B2 | 5/2015 | Bennett et al. | |
| 10,166,227 B2 | 1/2019 | Cho et al. | |
| 10,576,075 B2 * | 3/2020 | Cho | ........................ A61P 35/00 |
| 2014/0142102 A1 | 5/2014 | Fairfax et al. | |
| 2015/0183784 A1 | 7/2015 | Bennett et al. | |
| 2016/0022684 A1 | 1/2016 | Kuo et al. | |
| 2016/0310423 A1 | 10/2016 | Betancort et al. | |
| 2017/0182025 A1 | 1/2017 | Nikolova et al. | |

FOREIGN PATENT DOCUMENTS

| | | |
|---|---|---|
| WO | WO 2014/096965 A2 | 6/2014 |
| WO | WO 2014/182929 A1 | 11/2014 |
| WO | WO 2015/002754 A2 | 1/2015 |
| WO | WO 2015/018522 A1 | 2/2015 |
| WO | WO 2015/058160 A1 | 4/2015 |
| WO | WO 2015/070020 A2 | 5/2015 |
| WO | WO 2015/160986 A2 | 10/2015 |
| WO | WO 2016/097870 A1 | 6/2016 |
| WO | WO 2017/112703 A1 | 6/2017 |

OTHER PUBLICATIONS

Pastor et al., "BET bromodomain proteins are required for glioblastoma cell proliferation," *Epigenetics*, vol. 9, No. 4, pp. 611-620 (Apr. 2014).
Gaudio et al., "The BET Inhibitor OTX015 (MK-8628) Shows in Vivo Antitumor Activity in Combination with Additional Targeted Agents in Diffuse Large B-Cell Lymphoma (DLBCL)," *Blood*, vol. 126, No. 23, 57th Annual Meeting of the American-Society-of-Hematology, (Dec. 2015), 5 pages.
Boi et al., The BET Bromodomain Inhibitor OTX015 Affects Pathogenetic Pathways in Preclinical B-cell Tumor Models and Synergizes with Targeted Drugs, *Clinical Cancer Research*, vol. 21, No. 7, pp. 1628-1638 (Jan. 2015).
Bernasconi, et al., "The BET Bromodomain Inhibitor OTX015 Shows Synergy with Several Anticancer Agents in Preclinical Models of Mantle Cell Lymphoma (MCL) and Multiple Myeloma (MM)," *European Journal of Cancer*, vol. 50, No. S6, Nov. 21, 2014, p. 184.
Gaudio, et al., "Bromodomain Inhibitor OIX015 (MK-8628) Combined with Targeted Agents Shows Strong in vivo/iantitumor Activity in Lymphoma," *Oncotarget*, vol. 7, No. 36, pp. 58142-58147 (Sep. 2016).
Search Report issued in co-pending European Patent Application No. 16879991.4, dated Jun. 17, 2019.
Written Opinion issued in co-pending Singapore Patent Application No. 11201805385Q, dated Aug. 5, 2019.
International Search Report and Written Opinion dated Jan. 11, 2018, in PCT/US2017/058614, filed Oct. 26, 2017.

(Continued)

*Primary Examiner* — Charanjit Aulakh
(74) *Attorney, Agent, or Firm* — Foley & Lardner LLP

(57) ABSTRACT

The present disclosure relates generally to compositions and methods of treating neoplastic diseases or cancers, such as glioblastoma and non-Hodgkin's lymphomas, or other cancers in which the subject suffers from an advanced solid tumor, comprising a combination of, or administering a combination of, a bromodomain and extra-terminal protein (BET) inhibitor and at least one chemotherapeutic agent, which does not inhibit BET directly. The BET inhibitor/chemotherapeutic agent combination, or combination therapy, can yield synergistic effects, thereby increasing the effectiveness of the cancer treatment as compared with the administration of either the BET inhibitor or the chemotherapeutic agent alone.

15 Claims, 7 Drawing Sheets

(56) References Cited

OTHER PUBLICATIONS

Vaibhav Sahai, et al., "Targeting BET Bromodomain Proteins in Solid Tumors," *Oncotarget*, vol. 7, No. 33, pp. 53997-54009 (Aug. 2016).
Office Communication issued in co-pending European Patent Application No. 17864117.1, dated Apr. 20, 2020.
Klingbeil, et al., "Inhibition of BET Bromodomain-Dependent XIAP and FLIP expression sensitizes KRAS-mutated NSCLC to pro-apoptotic agents," *Cell Death and Disease*, vol. 7, e2365 (2016).
Examination Report issued in co-pending Australian Patent Application No. 2017347853, dated Mar. 31, 2021.
Notice of Allowance issued in co-pending U.S. Appl. No. 16/750,996, dated Aug. 12, 2020.

\* cited by examiner

BROMODOMAIN AND EXTRA-TERMINAL PROTEIN INHIBITOR COMBINATION THERAPY

CROSS REFERENCE

This application is a continuation of U.S. patent application Ser. No. 16/750,996, filed Jan. 23, 2020, which is a divisional of U.S. patent application Ser. No. 16/191,319, filed Nov. 14, 2018, which is a continuation of U.S. patent application Ser. No. 15/796,571, filed Oct. 27, 2017, which claims the benefit of priority from U.S. Provisional Patent Application No. 62/413,763, filed Oct. 27, 2016, and U.S. Provisional Patent Application No. 62/560,840, filed Sep. 20, 2017, the contents of which are hereby incorporated by reference in their entireties.

FIELD

The embodiments described herein provide compositions, formulations, and methods for treating cancer and neoplastic disease; in which such treatments include combination therapies comprising administration of a bromodomain and extra-terminal (BET) protein inhibitor and a chemotherapeutic agent, such as temozolomide or paclitaxel.

BACKGROUND

There remains a need for compositions, formulations, and methods for treating subjects with cancers such as, for example, basal cell carcinoma, relapsed or refractory non-Hodgkin's lymphomas (NHL), glioblastoma multiforme, anaplastic astrocytoma, or other advanced solid tumors.

For example, basal cell carcinoma (BCC) is a common cancer throughout the world, and its incidence is increasing. In the United States alone, more than 3.5 million new patients are diagnosed annually with non-melanoma skin cancer. Most BCCs can be cured by topical therapy, surgery, radiotherapy, or a combination thereof. Advanced BCC, however, often causes significant disfigurement and morbidity with associated physical and psychological sequelae, because BCC occurs commonly in sun-exposed areas such as the face. Further, a small proportion of these cancers are metastatic and not amenable to typical therapy. Near all BCCs are associated with aberrant hedgehog (Hh) signaling, which stimulates unregulated cell growth, and several therapeutic Hh inhibitors have proved useful in treating BCC. Unfortunately, about 20% of BCCs develop resistance to current Hh inhibitors, usually via Hh pathway reactivation by mutations that either interfere with the drug binding pocket, increase Hh signaling activity, or act through concurrent copy number changes in suppressor genes. Patients will benefit from the development of well-tolerated agents that overcome these resistance pathways by, for example, targeting proteins downstream in relevant signaling pathways.

SUMMARY

The aspects and embodiments of the present disclosure provide for methods and pharmaceutical compositions for treating subjects with cancer and neoplastic disease; such as those with advanced solid tumors, relapsed or refractory non-Hodgkin's lymphomas, glioblastoma multiforme, anaplastic astrocytoma, basal cell carcinoma, or other cancers. At least one embodiment provides a method for treating cancer and neoplastic disease comprising administering to a subject in need thereof a therapeutically effective amount of at least one BET inhibitor and a therapeutically effective amount of at least one chemotherapeutic agent. The chemotherapeutic agent may be an alkylating agent, such as temozolomide, or a mitotic inhibitor such as paclitaxel or paclitaxel protein-bound particles. An exemplary BET inhibitor is 4-[2(cyclopropylmethoxy)-5-methylsulfonylphenyl]-2-methylisoquinolin-1-one. According to the method, administration of a BET inhibitor and chemotherapeutic agent may be concurrent or sequential.

In at least one embodiment, a BET inhibitor and chemotherapeutic agent of the combination therapy may be administered in a single pharmaceutical composition. Some embodiments provide a composition comprising a pharmaceutically effective amount of a BET inhibitor and temozolomide, formulated in a pharmaceutically acceptable carrier. Some embodiments provide a composition comprising a pharmaceutically effective amount of a BET inhibitor and protein-bound paclitaxel, formulated in a pharmaceutically acceptable carrier. In one embodiment, BET inhibitor and chemotherapeutic agent of the combination therapy may exist as separate pharmaceutical compositions administered either concurrently or sequentially. In another embodiment, BET inhibitor and chemotherapeutic agent are independent pharmaceutical compositions that are admixed before administration (i.e., admixed in a pharmaceutically acceptable solution for injection or infusion). In still another embodiment, BET inhibitor and chemotherapeutic agent are disposed as separate pharmaceutical compositions that are packaged together for administration (e.g., a blister-pack containing oral formulations, or packaging comprising an oral dosage form and an injectable dosage form).

In at least one embodiment, administering the BET inhibitor and the chemotherapeutic agent results in a synergistic inhibition of cell proliferation or increased cell death (e.g., tumor cell death) compared with administration of either the BET inhibitor or the chemotherapeutic agent alone. The chemotherapeutic agent can be an anti-proliferative or proapoptotic compound, and can be selected so as to show a synergistic anti-proliferative or proapoptotic effect when co-administered with a BET inhibitor.

Combinatorial treatment with a BET inhibitor and a chemotherapeutic agent can result in a synergistic anti-cancer effect or can overcome developed resistance. Synergistic effects or overcoming developed resistance can allow lower doses, significantly reducing therapy cost in a substantial patient population.

DETAILED DESCRIPTION

Figure 1:
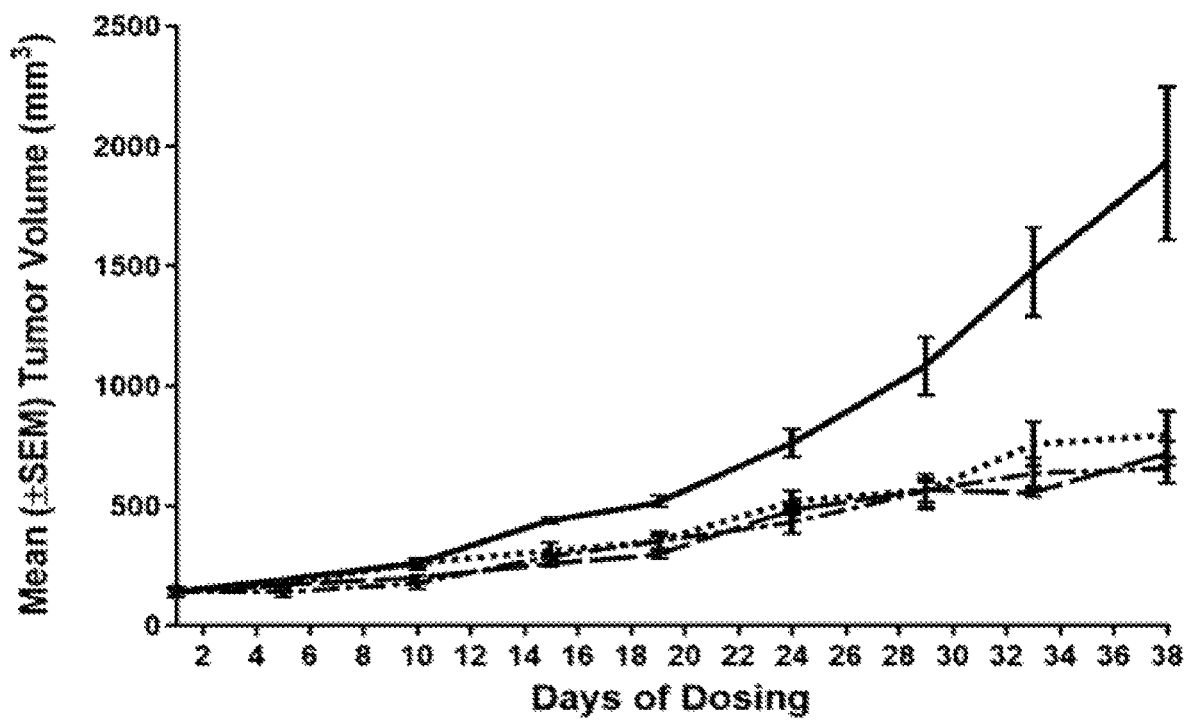
FIG. 1 is a graph showing dose-dependent tumor growth inhibition as measured by tumor volume in a TNBC PDX model, COH70, following dosing with Compound A (4-[2-(cyclopropylmethoxy)-5-methylsulfonylphenyl]-2-methyl-isoquinolin-1-one). Compound A dosing by mouth (PO) once daily for 3 consecutive days, followed by 4 days off (3×/week); ——— Vehicle; - - - - Compound A 12.5 mg/kg PO 3×/week; ——— ——— Compound A 16 mg/kg PO 3×/week; - ——— - ——— Compound A 20 mg/kg PO 3×/week; SEM is the standard error of the mean.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" when used in connection with percentages may mean±1%. Unless defined otherwise, all technical and scientific terms used herein have the same meaning as those commonly understood to one of ordinary skill in the art to which this invention pertains.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

At least one embodiment provides for a method of treating cancer with a combination therapy comprising administration of an in inhibitor of a bromodomain and extraterminal (BET) protein and a chemotherapeutic agent. For example, the BET inhibitor may be a bromodomain inhibitor, such as 4-[2-(cyclopropylmethoxy)-5-methylsulfonylphenyl]-2methylisoquinolin-1-one (Compound A); and the chemotherapeutic agent may be temozolomide (4-methyl-5-oxo-2,3,4,6,8-pentazabicyclo[4.3.0]nona-2,7, 9-triene-9-carboxamide), protein bound paclitaxel (e.g., ABRAXANE@), or romidepsin (1S,4S,7Z,10S,16E,21R)-7-ethylidene4,21-diisopropyl-2-oxa-12,13-dithia-5,8,20,23-tetrazabicyclo[8.7.6]tricos-16-ene-3,6,9,19,22pentone).

Accordingly, an example embodiment provides combination therapy comprising Compound A and temozolomide. Another example embodiment provides combination therapy comprising Compound A and protein-bound paclitaxel. And yet another example embodiment provides combination therapy comprising Compound A and romidepsin. As described in more detail herein. Compound A is a potent and reversible inhibitor of the epigenetic BET proteins. Surprisingly, combination therapy comprising administration of a BET inhibitor (e.g., Compound A) and a chemotherapeutic agent (e.g., temozolomide, protein bound paclitaxel, or romidepsin) exhibited synergistic therapeutic results.

At least one embodiment provides for treatment of subjects with cancer, particularly advanced solid tumors or relapsed/refractory NHLs, comprising administering a pharmaceutical formulation comprising a BET inhibitor and a chemotherapeutic agent, such as an alkylating agent (temozolomide) or mitotic inhibitor (such as a protein-bound paclitaxel). For example, the BET inhibitor may be a bromodomain inhibitor such as Compound A. A specific example relates to assessing the safety, tolerability, pharmacokinetics and preliminary efficacy of Compound A in human subjects.

The present embodiments provide methods and compositions, such as pharmaceutical formulations that provide therapeutic benefit in the treatment of cancers, such as advanced solid tumors or relapsed/refractory NHLs, for example, DLBCL or iNHL. Additional examples of cancers associated with solid tumors include fibrosarcoma, myxosarcoma, liposarcoma, chondrosarcoma, osteogenic sarcoma, chordoma, angiosarcoma, endotheliosarcoma, lymph-angiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma. Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

The terms "subject" or "patient" as used herein refer to any subject, particularly a mammalian subject, for whom diagnosis, prognosis, or therapy of a cancer, such as a solid tumor or relapsed/refractory NHL (e.g., diffuse large B-cell lymphoma (DLBCL) or indolent NHL (iNHL)) is relevant. The terms "subject" or "patient" may include any human or nonhuman animal as context indicates.

As used herein the terms "treat." "palliating," "ameliorating," "treatment." or "treatment of" (e.g., in the phrase "treating a patient having an advanced solid tumor or relapsed/refractory NHL) are used interchangeably herein and refer, in general, therapeutic benefit or prophylactic benefit, e.g., reducing the potential for disease, reducing the occurrence of disease, or reducing the severity of disease. For example, treating can refer to the ability of a therapy when administered to a subject, to prevent further tumor growth or malignancy, or to cure or to alleviate at least partially a disease symptom, sign, or cause. Treating also refers to mitigating or decreasing at least one clinical symptom or inhibition or delay in the progression of the condition or prevention or delay of the onset of a disease or illness. Thus, the terms "treat." "treating." or "treatment of" (or grammatically equivalent terms) refer to both prophylactic and therapeutic treatment regimes. These terms refer to an approach for obtaining beneficial or desired results, including but not limited to therapeutic benefit or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Accordingly, "therapeutic agent" as used herein refers to any therapeutically active substance that is administered to a subject to produce a desired, usually beneficial, effect. The term therapeutic agent includes. e.g., classical low molecular weight therapeutic agents commonly referred to as small molecule drugs; and biologics including, but not limited to, antibodies or functionally active portions thereof, peptides, lipids, protein drugs, protein conjugate drugs, fusion proteins, enzymes, nucleic acids, ribozymes, genetic material, viruses, bacteria, eukaryotic cells, and vaccines. A therapeutic agent can also be a pro-drug. A therapeutic agent can also be a radioactive isotope. A therapeutic agent can be an agent activated by a form of energy such as light or ultrasonic energy, or activated by other circulating molecules that can be administered systemically or locally. In addition, the therapeutic agent can be pharmaceutically formulated.

References to "pharmaceutical agent," "therapeutic agent," "pharmaceutically active." "pharmaceutical," "drug." "medicament," "active agent," "active drug" "active pharmaceutical ingredient." and the like, refer in a general sense to substances useful in the medical and scientific arts, including, for example, drugs, biologics, diagnostic agents (e.g., dyes or contrast agents) or other substances used for therapeutic, diagnostic, or preventative (e.g., vaccines), or research purposes. Example pharmaceutical agents include small molecules, chemotherapeutic agents, contrast agents, anesthetics, interfering RNAs, gene vectors, biologics, immunogens, antigens, interferons, polyclonal antibody preparations, monoclonal antibodies, insulins, or combinations of any of these. As noted, a pharmaceutical composition or pharmaceutical formulation may comprise one or more active therapeutic agents, or a combination of active and diagnostic agents, etc., typically further comprising a suitable excipient(s).

Inactive" substances refer to carriers, excipients, diluents, and the like, which are well-known in the art, although such substances may have beneficial function in the mixed injectable, such as, for example, surfactant, inorganic or organic salt, stabilizer, diluent, solubilizer, reducing agent, antioxidant, chelating agent, preservative, adjuvants, isotonic or buffering agents, or any excipient conventionally used in pharmaceutical compositions (i.e., "pharmaceutically acceptable excipient") and the like. These active or inactive substances may also include substances having immediate, delayed, controlled, or sustained release characteristics.

A "pharmaceutical formulation," "formulation," or "pharmaceutical composition" refers to a drug product that includes at least one active agent and may further include at least one pharmaceutically acceptable excipient, carrier, buffer, stabilizer, or other material well known to those skilled in the art. For example, a typical injectable pharmaceutical formulation includes a parenterally acceptable aqueous solution which is pyrogen-free and has suitable pH, isotonicity, and stability. Pharmaceutical compositions can have diagnostic, therapeutic, or research utility in various species, such as for example in human patients or subjects. In at least one embodiment, a pharmaceutical composition comprises a BET inhibitor and a chemotherapeutic agent such as temozolomide, protein-bound paclitaxel, or romidepsin. For example, a BET inhibitor may be 4-[2-(cyclopropylmethoxy)-5-methylsulfonylphenyl]-2methyl-isoquinolin-1-one (Compound A). The agents and compositions described herein can be formulated by any conventional manner using one or more pharmaceutically acceptable carriers or excipients as described in accepted literature. See, e.g., REMINGTON—Science & Practice of Pharmacy, 22nd edition (Lloyd, ed., Pharmaceutical Press, London, U K. 2012). Such formulations contain a therapeutically effective amount of an active agent(s) described herein, preferably in purified form, together with a suitable amount of carrier so as to provide the form for proper administration to the subject.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism. The term "prodrug" is also meant to include any covalently bonded carriers, which release the active compound in vivo when such prodrug is administered to a mammalian subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino, or free mercapto group. Examples of prodrugs include, but are not limited to, acetate, formate and benzoate derivatives of alcohol or amine functional groups in active compounds. See, e.g., DESIGN OF PRODRUGS, at 7-9, 21-24 (Bundgaard. Ed., Elsevier, Amsterdam, 1985). For example, temozolomide is an imidazotetrazine derivative prodrug of the alkylating agent dacarbazine.

A pharmaceutical formulation can include a therapeutically effective amount of at least one active agent. Such effective amounts can be readily determined by one of ordinary skill in the art based, in part, on the effect of the administered dosage form, or the combinatorial effect of an agent and one or more additional active agents, if more than one agent is used. A therapeutically effective amount of an active agent can also vary according to factors such as the disease state, age, sex, and weight of the individual, and the ability of the agent (and one or more additional active agents) to elicit a desired response in the individual. e.g., amelioration of at least one condition parameter. For example, a therapeutically effective amount of a dosage form can inhibit (lessen the severity of or eliminate the occurrence of), prevent a particular disorder, or lessen any one of the symptoms of a particular disorder known in the art or described herein. A therapeutically effective amount may also be one in which any toxic or detrimental effects of the active agent or dosage form are outweighed by the therapeutically beneficial effects.

Accordingly, an active agent can be administered to a subject as a monotherapy, or as a combination therapy with another active agent in a combination dosage form, or as an additional treatment. e.g., another treatment for the same, an associated, or an additional disorder. For example, a BET inhibitor can be combined with a chemotherapeutic agent, such as temozolomide or protein-bound paclitaxel, in the same formulation, or in a different formulation administered simultaneously or sequentially. Additionally, combination therapy can include administering to the subject (e.g., a human patient) one or more agents (e.g., antibiotics, anticoagulants, anti-hypertensives, or anti-inflammatory drugs) that provide a therapeutic benefit to subject. In another example, combination therapy can include administering to the subject a BET inhibitor, temozolomide, or a combination comprising a BET inhibitor and temozolomide, and one or more additional agents that provide therapeutic benefit to a subject who has cancer, such as an advanced solid tumor or relapsed/refractory NHL. Similarly, in another example, combination therapy can include administering to the subject a BET inhibitor, protein-bound paclitaxel, or a combination comprising a BET inhibitor and paclitaxel, and one or more additional agents that provide therapeutic benefit to a subject who has cancer. Similarly, in yet another example, combination therapy can include administering to the subject a BET inhibitor, romidepsin, or a combination comprising a BET inhibitor and romidepsin, and one or more additional agents that provide therapeutic benefit to a subject who has cancer. In some embodiments, an active agent and one or more additional active agents are administered in a single dosage form. e.g., a pharmaceutical composition comprising a BET inhibitor and temozolomide, paclitaxel or romidepsin. In other embodiments, an active agent is administered first in time and an additional active agent(s) is administered second in time. In some embodiments, one or more additional active agents are administered at the same time, but using different drug delivery devices or delivery modes, for example, providing for combination therapy comprising administration of a BET inhibitor and temozolomide, or comprising a BET inhibitor and paclitaxel, or comprising a BET inhibitor and romidepsin. In at least one embodiment, the BET inhibitor is 4-[2-(cyclopropylmethoxy)-5-methylsulfonylphenyl]-2methylisoquinolin-1-one (Compound A).

The administration of a BET inhibitor, or both a BET inhibitor and chemotherapeutic agent as combination therapy described herein, may replace or augment a previously or currently administered therapy. For example, upon treating with one pharmaceutical formulation, administration of an additional active agent(s) can cease or be diminished, e.g., be administered at lower concentrations or with longer intervals between administrations. In some embodiments, administration of a previous therapy can be maintained. In some embodiments, a previous therapy is maintained until the level of an active agent reaches a level sufficient to provide a therapeutic effect. Accordingly, two therapies can be administered in combination, sequentially, or simultaneously.

In at least one embodiment, combination therapy comprising the administration of a BET inhibitor and a chemotherapeutic agent has an additive effect in comparison with therapy administration comprising either BET inhibitor or chemotherapeutic agent alone. In other embodiments, the administration of a BET inhibitor and a chemotherapeutic agent in combination therapy has a synergistic effect in comparison with therapy administration comprising either BET inhibitor or chemotherapeutic agent alone. In some embodiments, combination therapy comprising the administration of a BET inhibitor and a chemotherapeutic agent reduces side effects in comparison with therapy administration comprising either BET inhibitor or chemotherapeutic agent alone or administration of the one or more other agents alone. For example, a combined therapy comprising administration of Compound A and temozolomide, paclitaxel or romidepsin resulted in a synergistic therapeutic result.

A therapeutic benefit is not necessarily a cure for a particular cancer (e.g., advanced solid tumor or relapsed/refractory NHL), but rather encompasses a result that most typically includes alleviation; increased survival; elimination of a tumor; reduction of a symptom associated with a cancer; prevention or alleviation of a secondary disease, disorder, or condition resulting from the occurrence of a cancer; or prevention of metastasis. Advanced solid tumors include unresectable solid tumors. Relapsed or refractory NHLs include DLBCL and iNHL.

In at least one embodiment described herein, the disease state of the treated subject (e.g., advanced solid tumor or relapsed/refractory NHL) is associated with epigenetics or the epigenetic state of the subject. Epigenetics refers, in general, to cellular and physiological phenotypic trait variations in which external or environmental factors affect genetic expression, rather than affecting changes in a DNA sequence per se. In other words, unlike genetics based on changes to the DNA sequence (the genotype) changes in gene expression or cellular phenotype of epigenetics have other causes. For example, DNA methylation and posttranslational modifications of the nucleosome histone proteins alters chromatin organization and gene expression without altering the underlying DNA sequence. Thus, epigenetic modification may influence if, when, or where specific genes are expressed, permitting a cell to regulate differential gene expression both reversibly and selectively. Chaidos et al., 6 Ther. Adv. Hematol. 128 (2015). Epigenetic modification is a dynamic and reversible process written, erased, and read by families of enzymes: 'writers' covalently attach acetyl or methyl groups; 'erasers' remove these groups; and 'readers' recognize and bind to these groups. Arrowsmith et al., 11 Nature Rev. Drug Discov. 384 (2012). Initiation and progression of cancer has increasingly been linked to misreading, miswriting or miserasing of these modifications. Chi et al., 10 Nature Rev. Cancer 457 (2010).

Bromodomain and extra-terminal (BET) proteins are a group of epigenetic 'readers' that play a pivotal role in the epigenetic process, and indeed may control expression of genes involved in cell growth and oncogenesis. Wyce, 4 Oncotarget 2419 (2013a). The posttranslational acetylation of nucleosome histone N-terminal tails represents the fundamental epigenetic mark of open structure chromatin and active gene transcription. Members of the BET protein family feature highly homologous, tandem bromodomains (BD-1 and BD-2) that recognize and bind these acetylated lysine histone tails. The BET proteins then act as scaffolds that recruit transcription factors and chromatin organizers which are required for transcription. For example, via a set of hydrogen-bonding interactions between highly conserved asparagine and tyrosine residues and the acetylated lysine, the BET bromodomains link chromatin to the CDK9-containing complex P-TEFb, which phosphorylates the large subunit of RNA Polymerase II and facilitates pause release and transcript elongation. Chaidos et al., 2015.

The BET family includes four members: BRD2. BRD3, BRD4, and BRDT. Dawson et al., New Engl. J. Med. 367 (2012); Jenuwein & Allis, 293 Science 1074 (2001). BRDT is found exclusively in germ cells, but BRD2. BRD3, and BRD4 are ubiquitous in germ and somatic cells. Chaidos et al., 2015. BRD4 (bromodomain containing protein-4) acts as a transcriptional co-regulator that binds to ε-N-lysine acetylation pockets on the tails of histones H3 and H4; where it can regulate gene expression through recruitment of additional proteins to its chromatin binding sites, thereby affecting chromatin structure and function. Jacobson et al., 288 Science 1422 (2000). Additionally, BRD4 binds preferentially at hyperacetylated super enhancer promoter regions and regulates transcription of target genes by recruiting co-activator or co-expressor complexes. Jung et al., 12 J. Neuroinflammation 1 (2015); Junwei & Vakoc, 54 Molec. Cell 728 (2014); Jenuwein & Allis, 2001.

Additionally, BET protein deregulation has been observed in several tumorous diseases. For example, a rare aggressive epithelial tumor (nuclear protein in testis (NUT)), is driven by fusions of the NUT protein with BRD3 or BRD4; and BET inhibitors have shown preclinical activity in this tumor. Filippakopoulos & Knapp, 2010; French, 203 Cancer Genet. & Cytogen, 16 (2010). BRD4 deregulation also occurs in leukemia, hepatocellular carcinoma, and breast cancers. Zuber et al., 478 Nature 524 (2011); Li et al., 7 Oncotarg. 2462 (2015). Further, overexpression of BRD2 and BRD4 has been demonstrated in glioblastoma cells, and BET inhibition by I-BET-151 (GSK1210151A) showed activity in glioblastoma multiforme (GBM) xenografts, comparable to temozolomide. Pastori et al., 9 Epigen. 611 (2014). Separately, BET inhibition suppressed the oncogenic transcription factor FOSL1 and its targets in a lung adenocarcinoma cell line. Lockwood et al., 109 PNAS 19408 (2012).

BRD4 has also been shown to control expression of genes involved in cell growth and oncogenesis, such as MYC. FOSL1, and GLI1. Shi et al., 25 Cancer Cell 210 (2014); Filippakopoulos & Knapp, 13 Nat. Rev. 337 (2014). BRD-containing complexes binding at super-enhancer sites often localize to promoter regions of key transcription factors, such as the oncogene c-MYC, which is activated in nearly 70% of all cancers. Nilsson & Cleveland 22 Oncogene 9007 (2003); Whyte et al., 153 Cell 307 (2013); Lovén et al. 153 Cell 320 (2013). BET inhibitors disrupt these complexes, down regulate MYC and have shown activity in human tumor xenografts of MYC-driven hematologic and solid tumors. Mertz et al., 108 PNAS 16669 (2011); Puissant et al., 3 Canc. Discov. 308 (2013); Shimamura et al., 19 Clin. Canc. Res. 6183 (2013); Wyce et al., 8 PLoS One e72967 (2013b); Bandopadhayay et al., 20 Clin. Cancer Res. 912 (2014); Hu et al. 16 Int. J. Mol. Sci. 1928 (2015); Li et al., 2015; Mazur et al., 21 Nat. Med. 116 (2015). Moreover, activity has been seen in clinical trials of a BET inhibitor in refractory/resistant lymphoma and leukemia. Dombret et al., ASH 2014, Abstract 117. BRD4, therefore, may have a role in the transcription of many genes, and the inhibition of BRD4 can potentially down regulate these transcribed genes, including genes implicated in drug resistance such as drug pumps/Examples of genes involved in cancer drug/therapy resistance are multidrug resistance (P-Glycoprotein, MDR1), multidrug transporter protein (MRP1, ABCC1), breast cancer resistance protein (BCRP, MXR, ABCG2) and glutathione (GSH).

BET proteins also appear to have a role in epithelial-mesenchymal transition (EMT) and development of cancer stem cells (CSCs). Epithelial-mesenchymal transition is associated with progression and metastasis of many carcinomas, and there appears to be a correlation between EMT, chemo-resistance and emergence of CSCs. Thiery, 2 Nat. Rev. Cancer 442 (2002); Thiery, 15 Curr. Opin. Cell Biol. 740 (2003); Huber et al., 17 Curr. Opin. Cell Biol. 548 (2005); Mani et al., 133 Cell 704 (2008); Castellanos et al., 6 OncoTargets Ther. 1261 (2013); Satoh et al., 50 J. Gastroenterol. 140 (2015). CSC have unrestrained proliferation and can self-renew, differentiate into other cell types, and form tumors in immunodeficient mice. Castellanos et al., 2013. Indeed, CSC may be responsible for tumor initiation, progression, recurrence and metastasis, as well as tumor heterogeneity and resistance to treatment. Sheridan et al., 8 Breast Canc. Res. R59 (2006); Campbell & Polyak, 6 Cell Cycle 2332 (2007); Li et al., 100 J. Natl. Cancer Inst. 672 (2008); Zhu et al., 32 Clin. Translat. Med. 1 (2014); Dawood et al., 28 Oncol. J. 1101 (2014). CSCs have been identified in leukemias, breast (particularly basal-like breast cancer), colon, GBM, head and neck, hepatic, lung, melanoma, pancreas and prostate carcinomas. Fang et al., 65 Canc. Res 9328 (2005); Ma et al., 132 Gastroenterol. 2542 (2007);

Tang et al., 21 FASEB J. 3777 (2007); Eppert et al., 17 Nature Med. 1086 (2011); Lathia et al., 29 Genes & Devel. 120 (2015).

Further regarding EMT, the Twist transcription factor has been identified as a key activator of EMT. Wu & Donohoe, 2 RNA Dis. 1 (2016). Twist exists in high levels in both aggressive pancreatic cancer cells with high metastatic potential, and breast cancer CSCs. Mani et al., 2008; Von Burstin et al., 137 Gastroenterol. 361 (2009). Importantly, BRD4 binds to Twist and this Twist/BRD4 interaction invokes tumorigenicity and invasion in BLBC. Shi, (2014). BET inhibitors can block this Twist-BRD4 interaction, however, and inhibit growth in a basal-like breast cancer xenograft model. Work in colorectal carcinoma supports BRD4's key role in EMT: the BRD4 inhibitor, MS417, inhibited colon cell proliferation, migration, and invasion impaired growth in a CRC xenograft model; and suppressed development of liver metastases. Hu et al., 16 Intl. J. Mol. Sci. 1928 (2015).

Furthermore, BET proteins are critical regulators of the Hedgehog (Hh) pathway, which is activated in CSCs. Varnat et al., 1 EMBO Mol. Med. 338 (2009); Amakye, 19 Nature Med. 1410 (2013); Tang et al., 2014; Infante et al., 36 Trends Pharma. Sci. 54 (2015). The Hh pathway is a key regulator of cell growth and differentiation during embryogenesis but is normally inactive in adult tissues. Ingham & McMahon, 15 Genes Devel. 3059 (2001); Von Hoff et al., 361 New Engl. J. Med. 1164 (2009). Aberrant activation of this pathway is implicated in tumorigenesis of various cancers such as medulloblastoma, rhabdomyosarcoma, and almost all BCCs. Xie et al., 391 Nature 90 (1998); Epstein, 8 Nature Rev. 743 (2008); Teglund & Toftgard. 1805 Biochim. Biophys. Acta 181 (2010). Hh ligand over-expression has also been observed in breast, colorectal, esophageal, lung, gastric, pancreatic, and prostate tumors. Teglund & Toftgard, 2010.

Additionally, aberrant Hh pathway signaling activates the Smoothened receptor (SMO) which, in turn, up-regulates glioma-associated oncogene homolog 1 (GLI1) transcriptional activity. GLI transcription is otherwise independent of Hh signaling, being driven by tumor growth factor-beta and KRAS. GLI1-driven transcription contributes to pancreas cancer progression. Nolan-Stevaux et al., 23 Genes Devel. 24 (2009). BRD4 and other BET proteins regulate GLI1 transcription downstream of SMO. In particular. BRD4 directly occupies GLI1 and GLI2 promoters. Tang et al., 20 Nature 732 (2014). This occupancy can be inhibited by BET inhibitors, thus offering a target in Hh-driven tumors regardless of dependence on activation by SMO. Of note, the BET inhibitor. JQ1, decreased tumor cell proliferation in vitro and in vivo in Hh-driven tumors, including tumors resistant to SMO antagonists. Tang et al., 2014. Another BET inhibitor, I-BET-151, suppressed Hh-dependent growth of medulloblastoma in vitro and in vivo, and suppressed SMO-independent activation of the Hh pathway in vitro. Long et al., 289 J. Biol. Chem. (2014). Aberrant Hh signaling also occurs in 95% of basal cell carcinomas (BCC). Migden et al., 16 Lancet Oncol. 716 (2015).

BCC is a common cancer throughout the world, and its incidence is increasing. Rubin, 353 New Engl. J. Med. 2262 (2005); Am. Cancer. Soc., Skin Cancer Facts, via ACS website, 2015. An estimated two to three million non-melanoma skin cancers occur globally each year, and approximately 80% are BCCs. World Health Organization, Ultraviolet radiation & the INTERSUN Programme, website, (2015); ACS, 2015. This is likely an underestimate because in the United States, where the registry is better documented than most countries, it is estimated that more than 3.5 million new patients are diagnosed with non-melanoma skin cancer annually. Furthermore, the incidence in Europe is increasing by 1 per 100,000 per annum. ACS, 2015; Rubin et al., 2005; Lomas et al., 166 Br. J. Dermatol. 1069 (2012).

Most BCCs can be cured by topical therapy, surgery or radiotherapy or a combination thereof. NCCN, guidelines; Trakatelli et al., 24 Eur. J. Dermatol. 312 (2014). A small proportion, however, progress to, or present with, locally advanced, or in less than 1%, metastatic BCC, which is not amenable to such therapy. Alonso et al., 20 JEADV 735 (2006); Danial et al., 169 Br. J. Dermatol. 673 (2013); Sekulic et al., 366 New Engl. J. Med. 2171 (2013); Bassett-Seguin et al., 16 Lancet Oncol. 729 (2015). Advanced BCC often causes significant disfigurement and morbidity, with associated physical and psychological problems since it occurs most commonly in sun-exposed areas, such as the head. Wong et al., 327 Br. J. Med. 794 (2003). Treatment of advanced and metastatic cases was difficult prior to availability of Hh inhibitors.

In BCC, the aberrant Hh signaling pathway is initiated when the extracellular Hh protein binds to the transmembrane receptor Patched (PTCH1) and liberates the SMO transmembrane protein. Ingham, 15 Genes & Devel. 3059 (2001); Rubin et al., 2006. Signaling by SMO mobilizes the normally latent zinc finger transcription factor GLI2, which transactivates the GLI1 promoter. Huangfu & Anderson, 102 PNAS 11325 (2005); Haycraft et al., 1 PLoS Genet 48 (2005); Liu et al., 132 Devel. 3103 (2005). GLI1 and GLI2 directly activate transcription of Hh target genes, including several involved in cell growth, such as MYCN and CCND1. Daya-Grosjean & Couvé-Privat, 225 Cancer Lett. 181 (2005); Scales, 30 Trends Pharma Sci. 303 (2009); Oliver et al., 100 PNAS 7331 (2003); Tang et al., 2014. Additionally, GLI1 amplifies Hh signaling by activating transcription of GLI2 in a positive feedback loop. Regl et al., 21 Oncol. 5529 (2002). Further, mutations of PTCH1 and SMO have been identified in basal cell nevus syndrome and sporadic BCCs. Hahn, 1996; Gailani, 1996; Unden, 1997; Xie, 1998. In 80-90% of BCC cases, mutations cause loss of function of PTCH1, which normally inhibits the signaling activity of SMO. Alcedo, 1996; Hahn et al., 85 Cell 841 (1996); Johnson et al., 272 Science 1668 (1996); Bassett-Seguin. 2015. Another 10% of BCC cases are due to constitutive activation of SMO. Xie, 1998; Bassett-Seguin et al., 16 Lancet Oncol. 729 (2015); Reifenberger et al., 152 Br. J. Dermatol. 43 (2005). These mutations cause constitutive Hh pathway signaling and the resultant expression of GLI1 in basal cells is associated with development of BCC. Dahmane et al. 389 Nature 876 (1997); Von Hoff et al., 361 New Engl. J. Med. 1164 (2009). Accordingly, agents capable of inhibiting SMO were developed.

ERIVEDGE® (vismodegib) directly binds to and inhibits SMO, and hence decreases formation of GLI1. LoRusso et al., 17 Cancer Res 2502 (2011); Sekulic et al., 2012; Von Hoff et al., 2009. See, e.g., Erivedge (vismodegib) Eur. PAR (Grenzach-Wyhlen, Germany. Roche Pharma AG, 2015), available on-line at the EMA Europa website. Vismodegib targets BCCs associated with both constitutively activated SMO mutations and PTCH1 mutations. Although vismodegib has a 30.3% independently reviewed response rate for metastatic BCC and a 42.9% response rate for locally advanced BCC in subjects for whom surgery or radiotherapy was inappropriate, the median duration of response was only 7.6 months and two-thirds of treated subjects did not respond. A recent safety review, with at least 12-months follow-up, showed that 36% of subjects withdrew from vismodegib treatment due to adverse events, plus an additional 10% due to subject request. Bassett-Seguin et al., 2015. ODOMZO® (sonidegib), another SMO inhibitor, has a 58% independently reviewed response rate for locally advanced BCC and the responses appear somewhat more durable, with 60% of locally advanced BCC, having investigator-assessed responses lasting at least six months. Migden et al., 2015. Twenty-eight percent (28%) of subjects were discontinued, however, and 32% of subjects had dose adjustments for adverse reactions. Currently, the durability of responses and tolerance to SMO inhibitors leave a substantial number of subjects with unmet medical need. See, e.g., Odomzo (sonidegib), European PAR (Nuremberg, Germany. Novartis Pharma GmbH, 2015), available on-line from the EMA Europa website.

Importantly, about 20% of BCC cancers develop resistance. Ridky & Cotsarelis, 27 Cancer Cell 315 (2015). This is usually related to Hh pathway reactivation via SMO mutations that are present in only 15%-33% of untreated BCCs compared with 69%-77% of resistant BCCs. The SMO mutations either interfere with the drug binding pocket, increase basal SMO activity, or act through concurrent copy number changes in suppressor of fused protein (SUFU) and GLI2. Atwood et al., 27 Cancer Cell 342 (2015); Sharpe et al., 27 Cancer Cell 327 (2015). A well-tolerated agent that could overcome these resistance pathways by targeting mechanisms downstream of SMO would be beneficial.

BRD4 and other BET bromodomain proteins regulate GLI1 transcription downstream of SMO, with BRD4 directly occupying GLI1 and GLI2 promoters. This occupancy can be inhibited by BET inhibitors; and the BET inhibitor, JQ1, decreases tumor cell proliferation both in vitro and in vivo in Hh-driven tumors—even those resistant to SMO inhibition. Tang et al., 2014. Hence clinical investigation of a BET inhibitor in locally advanced or metastatic BCC subjects with de novo or acquired resistance is warranted.

Accordingly, certain substituted heterocyclic derivative compounds, based on isoquinolinones and related heterocyclic structures, have proved useful for epigenetic regulation as they inhibit bromodomain-mediated recognition of the acetyl lysine regions in proteins, such as histones; and are thus useful for the treatment of cancer and neoplastic disease. Example cancers for which these compounds and pharmaceutical compositions are useful include NUT midline carcinoma, Burkitts lymphoma, prostate cancer, breast cancer, bladder cancer, lung cancer, melanoma, glioblastoma, and the like. These substituted heterocyclic derivative compounds are based upon isoquinolinones and related heterocyclic structures, and are typically substituted at the 4-position with a group such as an aryl, a heteroaryl and the like, and on the nitrogen atom of the isoquinolinone or related heterocyclic structure with a small alkyl group, such as a methyl group. An example of such compounds, 4-[2-(cyclopropylmethoxy)-5methylsulfonylphenyl]-2-methyl-isoquinolin-1-one, discussed further herein, is potent and reversible inhibitor of the epigenetic target BET proteins, including BRDs. In general, the substituted heterocyclic derivatives of the present embodiments belong to a class of compounds having the structures represented by, for example, Formula I, Formula II, or salts thereof. See WO 2015058160; U.S. Patent Pub. No. US 20150111885; U.S. Pat. No. 9,034,900.

More specifically, an embodiment of a substituted heterocyclic derivative with BET inhibitor activity is shown in Formula I:

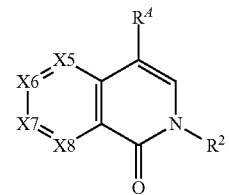

Formula I wherein $R^2$ is $CH_3$, $CH_2CH_3$, $CH_2CF_3$. $CH_2F$, $CHF_2$, $CF_3$, $CH_2D$, $CHD_2$, or $CD_3$;

X5 is C—$R^5$ or N, wherein $R^5$ is hydrogen, halogen, OH, CN, $OR^{61}$, $NHR^{61}$, $N(R^{61})_2$, alkyl, cycloalkyl, cycloalkylalkyl, aryl, aralkyl, heterocyclyl, heterocyclylalkyl, heteroaryl, or heteroarylalkyl, in which each $R^{61}$ is independently selected from alkyl, cycloalkyl, cycloalkylalkyl, aryl, aralkyl, heterocyclyl, heterocyclylalkyl, heteroaryl, or heteroarylalkyl;

X6 is C—$R^6$, or N wherein $R^6$ is hydrogen, halogen, OH, CN, alkyl, cycloalkyl, cycloalkylalkyl, amino, alkylamino, dialkylamino, cycloalkylalkylamino, alkoxy, or cycloalkylalkoxy;

X7 is C—$R^7$ or N wherein $R^7$ is hydrogen, halogen, OH, CN, $OR^{61}$, $NHR^{61}$, $N(R^{61})_2$, alkyl, cycloalkyl, cycloalkylalkyl, aryl, aralkyl, heterocyclyl, heterocyclylalkyl, heteroaryl, or heteroarylalkyl;

X8 is C—$R^8$ or N wherein $R^8$ is hydrogen, halogen, or alkyl; wherein no more than two of X5, X6, X7, or X8 may be N; and $R^4$ is

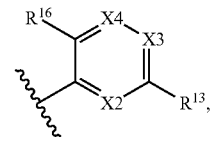

wherein

X2 is N or C—$R^{12}$, wherein $R^{12}$ is hydrogen, halogen, alkyl, or alkoxy;

$R^{13}$ is Y—Z; wherein

Y is selected from a bond, $CH_2$, $CH(C_1$-$C_4$ alkyl); and

Z is selected from $SO_2R^{21}$, $N(R^{22})SO_2R^{21}$, $SO_2N(R^{22})_2$, $N(R^{22})SO_2N(R^{22})_2$. $CON(R^{22})2$, $N(R^{22})CO_2R^{21}$, $N(R^{22})CON(R^{22})_2$, $N(R^{22})COR^{21}$, $COR^{21}$, $OC(O)N(R^{22})_2$, $OSO_2N(R^{22})_2$, or $N(R^{22})SO_3R^{21}$;

wherein each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

X3 is N or C—R$^{14}$, wherein R$^{14}$ is hydrogen, halogen, —CN, alkyl, cycloalkyl, or alkoxy; and X4 is N or C—R$^{15}$, wherein R$^{15}$ is hydrogen, halogen, alkyl, CN, or alkoxy; and R$^{16}$ is hydrogen, halogen, or W—X, wherein
W is a bond, O, S, or NH, and
X is selected from alkyl, aryl, aralkyl, cycloalkyl, cyclo-alkylalkyl, alkynyl, cycloalkylalkynyl, heterocyclyl, heterocyclylalkyl, heteroaryl, or heteroarylalkyl.

Another an embodiment of a substituted heterocyclic derivative with BET inhibitor activity is shown as Formula II:

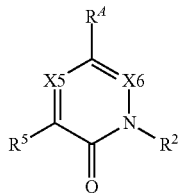

Formula II wherein
R$^2$ is alkyl, cycloalkyl, cycloalkylalkyl, heterocyclylalkyl, aralkyl, or heteroarylalkyl;
X5 is C—R$^5$ or N; wherein
R$^5$ is hydrogen, halogen, OH, CN, OR$^{61}$, NHR$^{61}$, N(R$^{61}$)$_2$, alkyl, cycloalkyl, cycloalkylalkyl, aryl, aralkyl, heterocyclyl, heterocyclylalkyl, heteroaryl, or heteroarylalkyl, wherein
each R$^{66}$ is independently selected from alkyl, cycloalkyl, cycloalkylalkyl, aryl, aralkyl, heterocyclyl, heterocyclylalkyl, heteroaryl, or heteroarylalkyl;
X6 is C—H or N, provided that if X6 is N, then X5 is C—R$^5$, and if X5 is N, then X6 is CH;
R$^6$ is hydrogen, halogen, OH, CN, alkyl, cycloalkyl, cycloalkylalkyl, amino, alkylamino, dialkylamino, cycloalkylalkylamino, alkoxy, S-alkyl, cycloalkylalkoxy, heterocyclyl, aralkoxy, heteroaryloxy, aryloxy, alkynyloxy, or N(H)COalkyl;

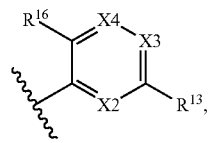

in which
X2 is N or C—R$^{12}$, wherein R$^{12}$ is hydrogen, halogen, alkyl, or alkoxy;
R$^{13}$ is —Y—Z, wherein
Y is selected from a bond. —CH$_2$—, or —CH(C$_1$-C$_4$ alkyl)-, and
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$;
each R$^{21}$ is independently selected from alkyl, cycloalkyl, cycloalkylalkyl, aryl, aralkyl, heterocyclyl, heterocyclylalkyl, heteroaryl, or heteroarylalkyl; and
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl;

X3 is N or C—R$^{14}$, wherein R$^{14}$ is hydrogen, halogen, —CN, alkyl, cycloalkyl, or alkoxy;

X4 is N or C—R$^{15}$, wherein R$^{15}$ is hydrogen, halogen, alkyl, —CN, or alkoxy; and R$^{16}$ is hydrogen, halogen. N(H)COX, or W—X, wherein W is a bond, O, S, or NH, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl; provided that when X6 is N, then R$^5$ and R$^6$ are not hydrogen.

A specific example of a heterocyclic derivative compound with BET inhibitor activity is 4-[2-(cyclopropylmethoxy)-5-methylsulfonylphenyl]-2-methylisoquinolin-1-one; which has the chemical formula C$_{21}$H$_{21}$NO$_4$S, a molecular weight 384, and the structure depicted in Formula III:

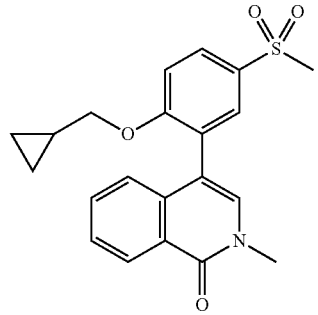

Formula III

See WO 2015058160; U.S. Patent Pub. No. US 20150111885; U.S. Pat. No. 9,034,900.

4-[2-(cyclopropylmethoxy)-5-methylsulfonylphenyl]-2-methylisoquinolin-1-one (Compound A) is a potent, reversible inhibitor of BET family members, including BRD2, BRD3, BRD4 and BRDT. It shows dose- and time-dependent inhibition of GLI1, and so is of value in the treatment of Hh-driven tumors and tumors with GLI-driven transcription. As discussed in more detail below, Compound A reduced tumor cell inoculation in a BLBC model in vivo, and showed more potent activity than the current clinical standard, temozolomide, in the GBM3 xenograft model. Interestingly, Compound A exhibited additive or synergistic effects in combination with temozolomide, suggesting it could be useful in tumors with CSCs and MYC-driven tumors. As noted and exemplified herein, Compound A can be formulated for oral administration.

Alkylating agents are example chemotherapeutic agents that can be used in combination with BET inhibitors for the treatment of cancers. For example, temozolomide is a prodrug and an imidazotetrazine derivative of the alkylating agent dacarbazine. The chemical name of temozolomide is 3,4-dihydro-3methyl-4-oxoimidazo[5,1-d]-as-tetrazine-8carboxamide, which has the following structure/formula:

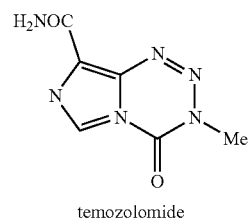

temozolomide

Temozolomide is rapidly hydrolyzed to the active 5-(3-methyltriazen-1-yl)imidazole-4-carboxamide (MTIC) at neutral and alkaline pH values, with hydrolysis taking place even faster at alkaline pH. See U.S. Pat. No. 5,260,291; WO 1997027202; WO 2002057269; WO 2008038031; EP 0252682; US 2006/183898.

Temozolomide is used as an alkylating agent in the treatment of some brain cancers, as a second-line treatment for astrocytoma, and a first-line treatment for glioblastoma multiforme. See NICE Guidance (2001); Stevens, in CANCER DRUG DESIGN & DISCOVERY (Neidle, Ed., Academic Press, New York, 2008). The therapeutic benefit of temozolomide depends on its ability to alkylate/methylate DNA, which most often occurs at the N-7 or O-6 positions of guanine residues. This methylation damages the DNA and triggers the death of tumor cells. Unfortunately, some tumor cells am able to repair this type of DNA damage by expressing $O^6$-alkylguanine DNA alkyltransferase (AGT), encoded in humans by the O-6methylguanine-DNA methyltransferase (MGMT) gene, thus diminishing the therapeutic efficacy of temozolomide. In some tumors, epigenetic silencing of the MGMT gene prevents the synthesis of this enzyme, and consequently such tumors are more sensitive to killing by temozolomide. Conversely, the presence of AGT protein in brain tumors predicts poor response to temozolomide. See Sitruk et al., 38 Gynécologie Obstétrique & Fertilité 660 (2010); Jacinto & Esteller, 6 DNA Repair 1155 (2007); Hegi et al., 352 New Eng. J. Med. 997 (2005); Hegi et al., 10 Lancet Oncol. 459 (2009).

Temozolomide can be formulated as a capsule for oral use, each capsule containing 5 mg, 20 mg, 100 mg, 140 mg, 180 mg, or 250 mg temozolomide. Temozolomide can also be formulated for injection, administered by intravenous infusion, in which the dose for infusion is the same as the dose for the oral capsule formulation. For example, in newly diagnosed glioblastoma, dosing consists of 75 mg/m² for 42 days (concomitant with focal radiotherapy) followed by 150 mg/m² for days 1 to 5 of a 28-day cycle. For refractory anaplastic astrocytoma, the initial dose is 150 mg/m² once daily for five consecutive days of a 28-day cycle.

Taxanes (paclitaxel and docetaxel) represent another example of a chemotherapeutic agent that may be used in combination therapy with BET inhibitors. See, e.g., U.S. Pat. No. 4,814,470. Originally isolated as a natural diterpene from *Taxus brevifolia* (pacific yew tree), the alkaloid paclitaxel binds the beta-tubulin subunits of microtubules, thus stabilizing microtubules from disassembly that must occur during cell division: blocking the normal progression of cell division by inhibiting spindle function eventually triggers apoptosis. Now obtained, inter alia, by extraction from plant cell fermentation, chromatographic purification and crystallization, paclitaxel is used to treat ovarian, breast, lung, pancreatic, and other cancers. The full chemical name of paclitaxel is (2α, 4α, 5β,7β, 10β, 13α)-4,10Bis(acetyloxy)-13-{[(2R,3S)-3-(benzoylamino)-2-hydroxy-3-phenylpropanoyl]oxy}-1,7dihydroxy-9-oxo-5,20-epoxytax-11-en-2-yl benzoate; and paclitaxel has the following structure:

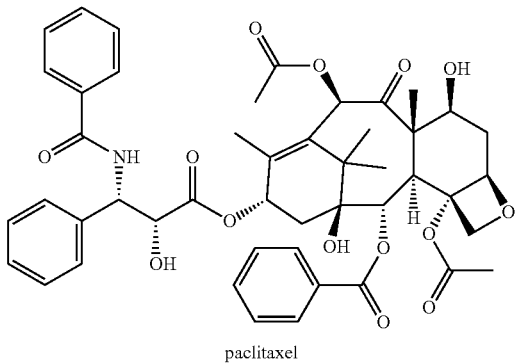 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

paclitaxel

In some embodiments, the taxane is nanoparticle albumin-bound ABRAXANE® (paclitaxel protein-bound particles for injectable suspension) (also called nab-paclitaxel). See, e.g., WO 2001089522A1. This protein-bound paclitaxel is indicated as first-line or combination therapy for several cancers, including non-small cell lung cancer, pancreatic cancer, and breast cancer. See, e.g., WO 2008057562. This composition uses the natural properties of albumin to reversibly bind paclitaxel, transport it across the endothelial cell, and concentrate paclitaxel in areas of tumor. More specifically, the mechanism of drug delivery involves, in part, glycoprotein-60-mediated endothelial cell transcytosis of paclitaxel-bound albumin and accumulation in the area of tumor by albumin binding to secreted protein, acidic, rich in cysteines (SPARC), also known as osteonectin, a glycoprotein predominantly expressed in tissues undergoing remodeling during normal development or in response to injury. Clinical studies have shown that nab-paclitaxel is significantly more effective than other paclitaxel formulations, the former almost doubling the response rate, increasing time before disease progression, and increasing survival in second-line patients. See WO 201006595.

Romidepsin acts as a prodrug with the disulfide bond undergoing reduction within the cell to release a zinc-binding thiol. The thiol reversibly interacts with a zinc atom in the binding pocket of Zn-dependent histone deacetylase to block its activity. Thus, it is an HDAC inhibitor. Many HDAC inhibitors are potential treatments for cancer through the ability to epigenetically restore normal expression of tumor suppressor genes, which may result in cell cycle arrest, differentiation, and apoptosis. Romidepsin is indicated for the treatment of patients with cutaneous T-cell lymphoma (CTCL) who have received ≥1 prior systemic therapy and patients with peripheral T-cell lymphoma (PTCL) who have received ≥1 prior therapy.

At least one embodiment provides a combination therapy comprising one of the heterocyclic derivative BET inhibitors and temozolomide. In at least one embodiment, the heterocyclic derivative is 4-[2-(cyclopropylmethoxy)-5-methylsulfonylphenyl]-2methylisoquinolin-1-one of Formula III (Compound A). In particular, synergistic effects have been observed for the use of Compound A and temozolomide in a temozolomide-resistant xenograft glioblastoma multiforme (GBM) model. More specifically, O-6-methylguanyl-methyl-transferase (MGMT) has been implicated in GBM resistance to the alkylating DNA damage of temozolomide. GBM3 is a GBM, patient-derived xenograft (PDX) mouse model with high MGMT expression, a non-methylated MGMT promoter, and a temozolomide-resistant phenotype. In previous studies of neurospheres cultured from GBM3. RT-PCR showed that Compound A down-regulated MGMT in a dose-responsive manner. When mice bearing GBM3 were given a single dose of Compound A, qRT-PCR showed MGMT down-regulation in the harvested tumor. An efficacy experiment explored whether Compound A could sensitize temozolomide-resistant GBM to temozolomide, and whether the combination had synergistic effects. Briefly, cohorts of mice bearing GBM3 were treated with either temozolomide. Compound A, or with a combination of Compound A and temozolomide. Tumor growth inhibition (TGI) was observed following dosing with Compound A alone or in combination with temozolomide. Although temozolomide, when given alone, did not yield significant TGI (3%); Compound A, when given alone, resulted in substantial TGI (63%) (12 mg/kg QD) and 76% (6 mg/kg BID). See FIG. 3. These data support the use of a BET inhibitor such as Compound A as a sensitizer to a chemotherapeutic agent such as temozolomide, perhaps by decreasing expression of genes responsible for resistance (e.g., drug pumps).

Surprisingly, the combination of Compound A and temozolomide was significantly superior to all other treatment regimens, and demonstrated synergy. See FIG. 3. As such, it is possible that lower dosages of both Compound A and temozolomide may be used effectively. This in turn reduces the toxicity and side effects, if any, associated with the administration either Compound A or temozolomide without reducing efficacy.

Figure 2:
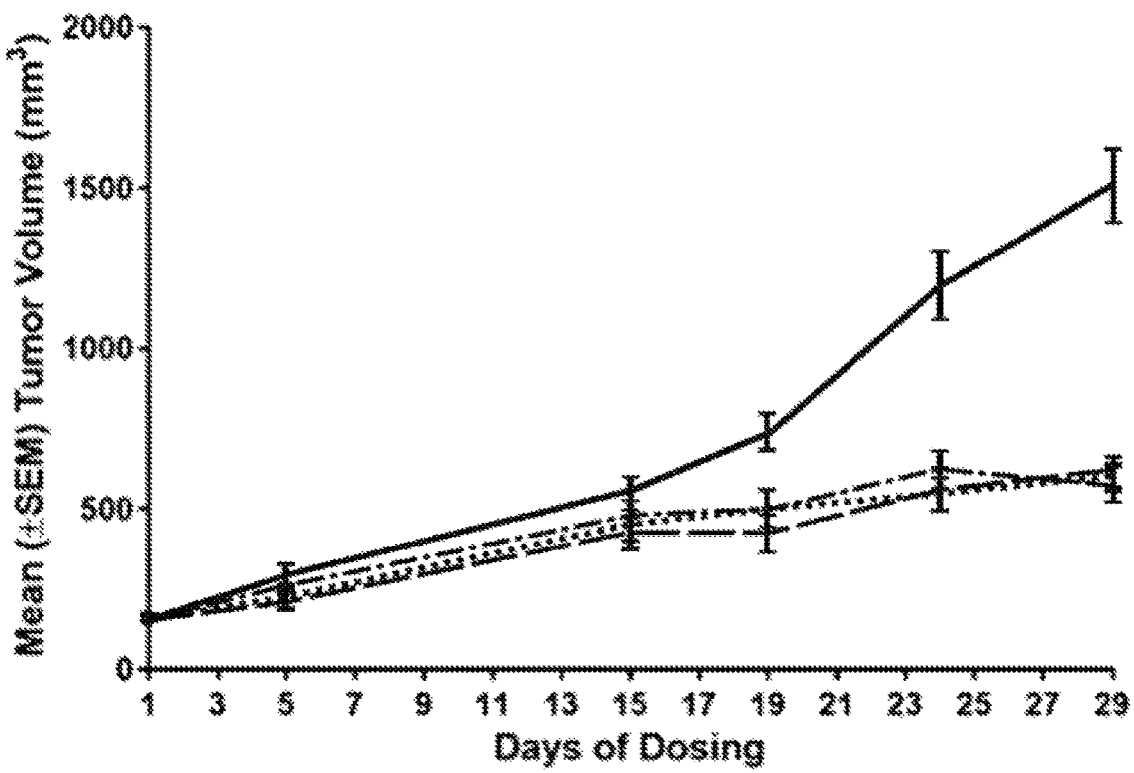
FIG. 2 is a graph showing dose-dependent tumor growth inhibition as measured by tumor volume in a GBM PDX model, GBM15, following dosing with Compound A. - Vehicle; - - - Compound A 15 mg/kg PO once daily for 5 consecutive days, followed by 2 days off (5/2); ——— ——— Compound A 25 mg/kg PO once daily for 3 consecutive days, followed by 4 days off (3/4); - ——— - ——— Compound A 37.5 mg/kg PO once daily for 2 consecutive days, followed by 5 days off (2/5); SEM is the standard error of the mean.

Other in vitro and in vivo studies have been conducted to characterize Compound A. For example TGI by Compound A was demonstrated in xenograft models of TNBC and GBM tumors. In the triple-negative breast cancer (TNBC) PDX model, COH7, Compound A treatment showed significant TGI in NOD/SCID/IL2Rγc$^{-/-}$ (NSG) mice. See FIG. 1. In the GBM PDX model, GBM15, efficacy of Compound A was exhibited using several treatment schedules. See FIG. 2. Compound A showed dose- and time-dependent inhibition of GLI1, and may be of value in the treatment of Hh-driven tumors or tumors with GLI-driven transcription, such as BCC. Compound A also reduced tumor cell inoculation in a basal-like breast cancer (BLBC) model in vivo, and showed more potent activity than the temozolomide in the GBM3 xenograft model, as well as exhibiting synergistic effects in combination with temozolomide, thus suggesting Compound A in combination with temozolomide is useful in tumors with cancer stem cells or MYC-driven tumors. For example, regulation of MYC gene expression by BRD4 has been shown in models of Burkitt's lymphoma with inhibition of BRD4, leading to growth arrest. Mertz, 2011.

Similarly, in a model of lung adenocarcinoma. BRD4 inhibition was also found to be antiproliferative; but this effect was ascribed to FOSL1 down-regulation. Lockwood, 2012. BRD4 also has been shown to regulate GLI1 gene expression, thereby modulating the hedgehog signaling pathway, which is known to be dysregulated in several cancer types. Tang, 2014. Compound A treatment inhibited MYC gene expression in Raji Burkitt's lymphoma cells with a mean $IC_{50}$ value of 0.06 μM; FOSL1 gene expression in U 87 glioblastoma astrocytoma cells with an $IC_{50}$ value of 0.03 μM; and GLI1 gene expression in MIA-PaCa-2 pancreatic adenocarcinoma cells with an $IC_{50}$ value of 0.24 μM. Treatment of mice bearing COH7 (a triple negative breast cancer (TNBC) patient-derived xenograft (PDX) tumor), with Compound A resulted in down-regulation of MYC, and modulation of MYC expression levels correlated with intratumor concentrations of Compound A. In addition to regulating gene expression in a dose dependent manner, growth of tumor cells was inhibited in vitro.

Several other in vitro and in vivo studies have been conducted to characterize the absorption, PK, distribution, metabolism and elimination of Compound A. Pharmacokinetics and oral bioavailability of Compound A were evaluated in Sprague-Dawley rats and Beagle dogs. In vivo treatment of mice bearing tumors replicated the in vitro data and provided dosing, scheduling, and plasma exposure information. Robust and reproducible bioanalytical methods for the quantitation of Compound A levels were developed and used in PK and toxicokinetic studies. Human PK parameters and exposures were predicted using allometric scaling.

Metabolism of Compound A was evaluated in vitro using human hepatocytes and the N-desmethyl derivative was identified as single metabolite. This metabolite was also observed in rat, dog, and monkey hepatocytes. No unique human metabolites were identified. Studies using recombinant CYP enzymes suggest multiple CYP enzymes can metabolize Compound A. In vitro. Compound A does not inhibit CYP1A2 and CYP3A4; but may inhibit CYP2C9, CYP2C19 and CYP2D6. In hepatocytes. Compound A did not induce CYP1A2, CYP2B6, or CYP3A4. Hence, at clinically relevant concentrations, Compound A has minimal potential to cause drug-drug interactions with co-administered drugs that are CYP substrates.

The safety and tolerability of combination therapy comprising Compound A and temozolomide in humans, as well as the biologic and clinical activity, are evaluated in a clinical study. Preclinical studies on Compound A are useful for this purpose. Based on the doses and exposures at which the principal treatment-related effects occurred in the GLP-compliant, four-week rat and dog studies, both species are considered of similar sensitivity to the toxicities associated with Compound A administration. A proposed human starting dose is 15 mg Compound A base, once daily for three consecutive days followed by four consecutive days off drug every week (3/7 day dose schedule). Because Compound A and temozolomide exhibit synergistic effect, the dose of either or both in combination therapy is examined.

The embodiments herein provide a method of treating a cancer comprising administration of a BET inhibitor and a chemotherapeutic agent; for example. Compound A and temozolomide. Accordingly, the embodiments further provide pharmaceutical compositions that include a BET inhibitor as an active ingredient, or both BET inhibitor and temozolomide as active ingredients. Such pharmaceutical compositions may take any physical form necessary depending on a number of factors including the desired method of administration and the physicochemical and stereochemical form taken by these agents or pharmaceutically acceptable salts thereof. Such physical forms include a solid, liquid, gas, sol, gel, aerosol, or any other physical form now known or yet to be disclosed. The concept of a pharmaceutical composition including the one or both of these agents also encompasses these agents without any other additive. The physical form of the pharmaceutical composition may affect the route of administration, and one skilled in the art knows to choose a route of administration that takes into consideration both the physical form of the composition and the disorder being treated. Pharmaceutical compositions that include either BET inhibitor or both BET inhibitor and temozolomide may be prepared using methodology well-known in the pharmaceutical art. A pharmaceutical composition that includes either Compound A or both Compound A and temozolomide may include an additional active agent. This additional active agent may have the same or a similar molecular target as Compound A. or a similar molecular target as temozolomide or albumin-bound paclitaxel, or it may act upstream or downstream of the molecular target(s) with respect to one or more biochemical pathways.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material. The combination therapy described herein encompasses BET inhibitors and temozolomide, paclitaxel or romidepsin prepared for the same or for different routes of administration. For example, Compound A may be prepared for oral administration, while temozolomide is prepared for infusion.

Determination of an effective amount of BET inhibitor (such as Compound A) and chemotherapeutic agent (such as temozolomide, paclitaxel or romidepsin) is within the capability of those skilled in the art in light of the disclosure provided herein. The effective amount of a pharmaceutical composition used for a particular purpose, as well as a pharmacologically acceptable dose determined by toxicity, excretion, and overall tolerance, may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of pharmaceutical compositions in vitro in cell lines or target molecules. Another example is the determination of the $LD_{50}$ (lethal dose causing death in 50% of the tested animals) of a pharmaceutical composition in experimental animals. The exact techniques used in determining an effective amount depend on factors such as the type and physical/chemical properties of the pharmaceutical composition, the property being tested, and whether the test is to be performed in vitro or in vivo. The determination of an effective amount of a pharmaceutical composition is well-known to one of skill in the art who uses data obtained from any tests in making that determination. Determination of an effective amount of a combination of agents, e.g., Compound A and temozolomide, paclitaxel or romidepsin, for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals. The toxicity and therapeutic efficacy of a pharmaceutical composition(s) may be determined by standard pharmaceutical procedures in cell cultures or animals. Examples include the determination of the $IC_{50}$ and the $LD_{50}$ for the combination therapy of the subject compounds. The data obtained from these cell culture assays and animal studies can be used in formulating a range of dosage for use in human. The dosage may vary depending upon the dosage form employed and the route of administration utilized.

Effective amounts of the active agents in the combined Compound A and temozolomide therapy results in the slowing of expansion of the cancer cells or TGI, but may have minimal effects on non-cancer cells. Concentrations that produce these effects can be determined using, for example, apoptosis markers such as the apoptotic index and/or caspase activities either in vitro or in vivo.

The method of treating cancer using the combination Compound A and temozolomide, paclitaxel or romidepsin include therapeutically effective amount of these and encompasses any method of dosing either one or both of these compounds. Dosing may include single or multiple administrations of any of a number of pharmaceutical compositions that include Compound A temozolomide, paclitaxel or romidepsin, or both Compound A and temozolomide, paclitaxel or romidepsin as an active ingredient(s). Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration depends on any of a number of factors including the subject being treated; the biomarkers determinative of a particular disease state or efficacy of an agent; the severity of the affliction; the manner of administration; the stage of disease development; the presence of one or more other conditions such as pregnancy, infancy; the presence of one or more additional diseases; or any other factor now known or yet to be disclosed that affects the choice of the mode of administration, the dose administered, and the time period over which the dose is administered.

Pharmaceutical compositions that include Compound A may be administered prior to, concurrently with, or after administration of a pharmaceutical composition that includes temozolomide, paclitaxel or romidepsin. If the compositions are administered concurrently, they are administered simultaneously or within one minute of each other. If not administered concurrently, the temozolomide, paclitaxel or romidepsin and Compound A pharmaceutical composition may be administered a period of one or more minutes, hours, days, weeks, or months before or after the pharmaceutical composition that includes the other agent. Alternatively, the combination of pharmaceutical compositions may be administered cyclically. Cycling therapy involves the administration of one or more pharmaceutical compositions for a period of time, followed by the administration of one or more different pharmaceutical compositions for a period of time, and repeating this sequential administration in order to reduce the development of resistance to one or more of the compositions, to avoid or reduce the side effects of one or more of the compositions, or to improve the efficacy of the treatment.

Additionally, set of genes has been identified whose expression is decreased upon ex vivo treatment with Compound A in peripheral blood mononuclear cells (PBMCs) and in whole blood. In the present study, changes in the expression of these genes in whole blood or other genes in tumor biopsy may provide confirmation that a dose is pharmacologically active and could help distinguish which dose shows the most compelling pharmacologic activity. Predictive biomarkers allow prospective identification of patients who are likely to benefit clinically from Compound A as a single agent, in combination with temozolomide, paclitaxel or romidepsin, or combined with other agents. Although the predictive diagnostic analyses in the current trial are exploratory in nature, they reveal associations between biomarkers and responses that provide a basis for future diagnostically driven studies.

These embodiments further encompass methods of treating cancer that comprise the combination therapy described herein and further comprise another treatment modality. Such treatment modalities include but are not limited to, radiotherapy, chemotherapy, surgery, immunotherapy, cancer vaccines, radioimmunotherapy, treatment with pharmaceutical compositions other than those described herein, or any other method that effectively treats cancer in combination with the disclosed compound now known or yet to be disclosed. The present combination therapy acts synergistically: the combination of Compound A and temozolomide, paclitaxel or romidepsin is more effective than either therapy administered alone. Another treatment modality could be additive or synergistic in efficacy. As such, lower dosages of both treatment modalities may be used effectively. This in turn reduces the toxicity and side effects, if any, associated with the administration either modality without a reduction in efficacy.

In another aspect, the combination therapy comprising Compound A and temozolomide is administered in combination with a therapeutically effective amount of radiotherapy. The radiotherapy may be administered concurrently with, prior to, or following the administration of the Compound A and temozolomide, paclitaxel or romidepsin therapy. The radiotherapy may act additively or synergistically with the combination therapy. This particular aspect of the invention would be most effective in cancers known to be responsive to radiotherapy. Cancers known to be responsive to radiotherapy include, but are not limited to, Non-Hodgkin's lymphoma. Hodgkin's disease. Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, other central nervous system neoplasms, or any other such tumor now known or yet to be disclosed.

In another aspect, a glioblastoma patient is treated by a bromodomain inhibitor, such as Compound A, in combination with temozolomide, paclitaxel or romidepsin. The effective dose of agents in the combination therapy are amounts effective to prevent occurrence of the symptoms of a disorder or to treat some symptoms of the disorder from which the patient suffers. Effective dose also includes an effective amount, a therapeutic amount, or any amount sufficient to elicit the desired pharmacological or therapeutic effects, thus resulting in effective prevention or treatment of the disorder. Thus, when treating a patient with glioblastoma, an effective amount of combination therapy provides amounts of Compound A and temozolomide, paclitaxel or romidepsin sufficient to slow, or arrest the progression, migration, metastasis, growth, or development of the tumor. The result may be that life is extended. A pharmacologically acceptable dose or maximum acceptable dose includes a dose that may be administered to a patient that is not lethal to the patient, nor causes effects that threaten the health or the life of the patient.

In particular, patients include any human being, nonhuman primate, companion animal, or mammal suffering from a disease. In one aspect, the patient has symptoms that signify the presence of a tumor or other growth in the brain. Such symptoms include headache, seizures, mental or personality changes, mass effect, or one of a number of focal or localized systems including ringing or buzzing sounds, hearing loss, loss of coordination, reduced sensation, weakness or paralysis, difficulty with walking or speech, difficulty keeping balance, decreased muscle control, or double vision. Patients may display one or more different brain tumor types including acoustic neurinoma, astrocytoma, ependyoma, glioblastoma multiforme, meningioma, metastatic tumors originating from another tumor type, mixed glioblastoma, oligodendroglioblastoma, or pineal region tumor.

Accordingly, the clinical investigation of an example BET inhibitor, Compound A, particularly in combination with temozolomide, paclitaxel or romidepsin, for antineoplastic activity in a variety of malignancies is warranted. A study in humans is designed to evaluate drug safety and pharmacokinetic profiles with various dose levels/regimens, and also reflects initial signals of drug efficacy in order to advance development of Phase 2 clinical trials. All human studies are conducted in compliance with International Conference on Harmonisation Good Clinical Practices.

More specifically, a study of a BET inhibitor in combination with a chemotherapeutic agent includes an open-label, Phase 1a, dose escalation and expansion, First-In-Human (FIH) clinical study in subjects with, for example, advanced solid tumors or relapsed/refractory NHLs. The study may be conducted in two parts: dose escalation (Part A) and dose expansion (Part B). An example proposed human starting dose is 15 mg Compound A base, once daily for 3 consecutive days followed by 4 consecutive days off drug every week (3/7 day dose schedule). A key exploratory objective identifies a dose of BET inhibitor and chemotherapeutic agent that is not only safe but that exhibits pharmacologic activity. For example, a proposed starting dose of temozolomide, paclitaxel or romidepsin and Compound A combination therapy can be ascertained with reference to the existing dosage regimens, typically with further pharmacokinetic, pharmacology, and toxicology studies.

Figure 4:
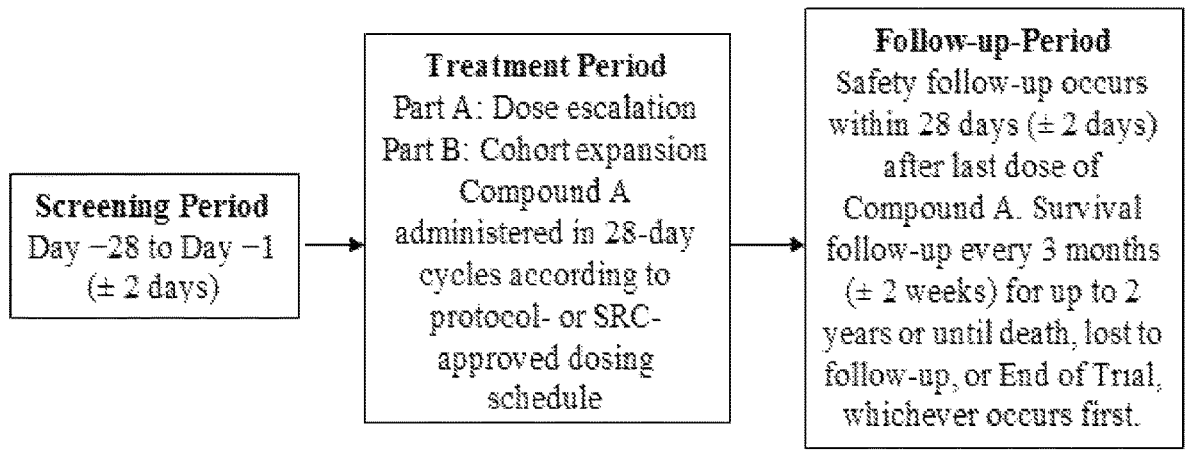
FIG. 4 is a schematic outlining an overall study design useful for demonstrating safety or efficacy of pharmaceutical compositions.

The dose escalation part of the study (Part A) explores escalating oral doses of combined therapy to estimate the maximum tolerated dose (MTD) and/or RPTD of the BET inhibitor and chemotherapeutic agent. The expansion part of the study (Part B) further evaluates the safety and efficacy of combination therapy administered at or below the MTD in selected expansion cohorts. One or more dosing regimens or disease subsets may be selected for cohort expansion. Parts A and B consist of three periods: Screening, Treatment, and Follow-up periods (see FIG. 4). Study Objectives are summarized in Table 1, and Study Endpoints are summarized in Table 2, both below:

TABLE 1

Study Objectives

Primary Objectives

The primary objectives of the study are:
Determine the safety and tolerability of BET inhibitor combination therapy.
Define the maximum tolerated dose (MTD) or the recommended Phase 2 dose (RP2D) of combination therapy.

Secondary Objectives

The secondary objectives are:
Provide information on the preliminary efficacy of combination therapy.
Characterize the pharmacokinetics (PK) of each component of combination therapy.

Exploratory Objectives

The exploratory objectives are:
Evaluate the pharmacodynamic (PD) effects of combination therapy on gene expression in peripheral blood and if available, in tumor samples.
Explore the relationship between combination therapy dose, plasma exposure, and selected clinical endpoints (e.g., measures of toxicities, preliminary activity, or biomarkers).
Characterize the principal metabolites of combination therapy in plasma provided sufficient data are available.

TABLE 2

Study Endpoints

| Endpoint | Name | Description | Timeframe |
| --- | --- | --- | --- |
| Primary | Safety endpoints | DLTs and MTD evaluated using the NCI CTCAE criteria. Version 4.03 | Dose escalation |
| Secondary | Preliminary efficacy | Determined by response rates by disease-appropriate response criteria | Dose escalation and expansion |
| | | Disease control rate (DCR), objective response rate (ORR), duration of response or stable disease, and progression-free survival (PFS) | Dose escalation and expansion |
| | Overall survival | From randomization to death due to any cause | Dose escalation and expansion |
| | PK endpoints | Peak (maximum) plasma concentration of drugs ($C_{max}$), area under the plasma concentration time-curve (AUC), time to peak (maximum) plasma concentration ($t_{max}$), terminal half-life ($t_{1/2}$), apparent clearance (CL/F), apparent volume of distribution (Vz/F), and accumulation index of each component of combined therapy | Dose escalation |
| Exploratory | PD endpoints | Gene expression in peripheral blood cell components | Dose escalation and expansion |
| | | Gene expression in tumor tissue, if available | |

DLT = dose-limiting toxicity; MTD = maximum tolerated dose; NCI CTCAE = National Cancer Institute Common Terminology Criteria for Adverse Events; NTD = non-tolerated dose; RNA = ribonucleic acid.

During the treatment period, formulations comprising BET inhibitor may be initially administered orally once daily (QD) for three consecutive days followed by four consecutive days off drug every week (three-/seven-day dose schedule) in each four-week cycle. Alternate dosing schedules (e.g., two-days-on/five-days-off, each week) are examined based on the SRC review of available safety, PK, pharmacodynamic (PD), and efficacy data. During the combination treatment period, formulations comprising BET inhibitor may be initially administered orally, once daily for three consecutive days followed by four consecutive days off drug every week (three-/seven-day dose schedule) in each four-week cycle; and formulations comprising temozolomide may be administered on days 7 to 9 and 22 to 24 of a four-week cycle. Alternate dosing schedules (e.g., two-days-on/five-days-off, each week) are examined based on the SRC review of available safety, PK, pharmacodynamic (PD), and efficacy data.

The decision to evaluate additional subjects within a dose cohort, a higher dose cohort, intermediate dose cohorts, smaller dose increments, alternate dosing schedules (e.g., BET inhibitor two-days-on/five-days-off, each week), or declare a MTD, is also determined by the SRC based on the BLRM assessment and their review of available safety (i.e., DLT and nonDLT data). PK, PD, and efficacy information.

After the first dose is administered in any cohort during dose escalation, subjects in each cohort are observed for 28 days before the next dose cohort can begin. No more than one subject per day is enrolled in a given dose escalation cohort. Subjects non-evaluable for DLT are replaced.

Regarding Part B-Cohort Expansion, following completion of dose escalation (Part A), selected tumor cohorts are enrolled into an expansion phase (Part B) with up to approximately twenty evaluable subjects each. Expansion may occur at the MTD and schedule established in the dose escalation phase, or at an alternative tolerable dose and schedule, based on review of available safety, PK, PD, and efficacy data from Part A combination therapy. One or more dosing regimens may be selected for cohort expansion. The SRC continues reviewing safety data regularly throughout the study, and recommends study continuation and dose modification, as appropriate.

For example, Compound A can be formulated as tablets for oral administration; and temozolomide can be formulated as capsules for oral administration. Alternatively, Compound A and temozolomide are co-formulated as a single tablet or capsule for oral administration. In another alternative example, Compound A is formulated as tablets for oral administration and temozolomide is formulated for infusion. As another example, because albumin-linked paclitaxel is formulated for infusion, Compound A may be formulated for oral administration. Alternatively. Compound A may be adapted to be infused with the protein-linked paclitaxel. Labeling is appropriate, e.g., for investigational use as per the regulations of the relevant country health authority.

For key efficacy assessments, subjects are evaluated for efficacy after every two cycles through Cycle 6, and thereafter every three cycles. All subjects who discontinue treatment are followed until progression or initiation of new systemic anticancer therapies. In the follow-up period, all subjects are followed for safety after the last dose of any component of the combined therapy. After the safety follow-up visit, all subjects are followed every subsequent three months for survival follow-up for up to two years or until death, lost to follow-up, or the end of trial.

Tumor response is determined. For solid tumors, assessment is based on Response Evaluation Criteria in Solid Tumors (RECIST 1.1). Eisenhauer et al., 45 Eur. J. Cancer 228 (2009). For NHLs, assessment is based on the International Working Group Revised Response Criteria for Malignant Lymphoma. Cheson et al., 25 J. Clin. Oncol. 579 (2007). [$^{18}$F]luorodeoxyglucose (FDG) positron emission tomography (PET) or FDG PET/CT imaging is required to confirm a complete response in subjects with FDG-avid tumors.

During the Part A dose escalation, approximately thirty to forty subjects are enrolled. During the Part B dose expansion, at least fourteen efficacy evaluable subjects for each tumor cohort are accrued initially. If the response rate is 20% or more, there is more than a 95% chance that one or more responders would be observed in the first fourteen subjects, to be updated by statistics based on change to DCR as a primary efficacy endpoint. Gehan, 13 J. Chronic Dis. 346 (1961). If no responder is observed out of fourteen subjects, the enrollment for this tumor cohort is stopped for futility. Otherwise, the tumor cohort is expanded to up to approximately twenty subjects if a responder is observed.

At all decision time points, the BLRM permits alterations in the dose increments based on the observed DLTs; however, the dose for the next cohort will not exceed a 100% increase from the prior dose. The MTD is the highest dose that is unlikely (<25% posterior probability) to cause DLT in ≥33% of the treated subjects in the first cycle of active agent.

Regarding Part B, Cohort Expansion, following completion of dose escalation (Part A), selected tumor cohorts are enrolled into an expansion phase (Part B) with up to approximately twenty evaluable subjects each. Expansion may occur at the MTD and schedule established in the dose escalation phase, or at an alternative tolerable dose and schedule, based on review of available safety, PK, PD, and efficacy data from Part A. One or more dosing regimens may be selected for cohort expansion.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

EXAMPLES

Example 1. Synthesis of 4-[2-(cyclopropyl-methoxy)-5-methylsulfonylphenyl]-2methylisoquinolin-1-one (Compound A)

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (□) and coupling constants (J) are reported in Hertz. For $^1$H NMR spectra, the solvent peak was used as the reference peak.

Step 1: 2-methyl-4-(4,4,5,5-tetramethyl-1,3,2-dioxaborolan-2-yl)isoquinolin-1-one

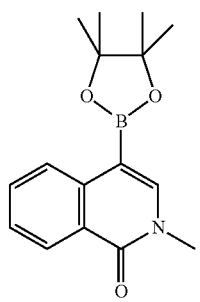 [SMILES: Cn1cc(B2OC(C)(C)C(C)(C)O2)c2ccccc2c1=O]

A suspension of 4-bromo-2-methylisoquinolin-1-one (100 mg, 0.42 mmol), bis(pinacolato)diboron (214 mg, 0.84 mmol). Pd(dppf)Cl2 (31 mg, 0.04 mmol) and potassium acetate (104 mg, 1.05 mmol) in dioxane (2 mL) under N2 was warmed to 90° C. for 135 min. It was then cooled to room temp and diluted with EtOAc (8 mL). The mixture was washed with an aq satd soln of NaHCO$_3$ (8 mL) and brine (8 mL). The organic phase was separated, dried over Na$_2$SO$_4$, filtered and concentrated under reduced pressure. The residue was purified by normal phase CC (10%-90% EtOAc/Hexanes) to give the title compound (44 mg, 37%). $^1$H NMR (CDCl$_3$, 400 MHz): δ 8.43 (d, J=7.9 Hz, 1H), 8.40 (dd, J=8.2 Hz, 0.9 Hz, 1H), 7.68 (s, 1H), 7.65 (ddd, J=8.2, 8.2, 1.1 Hz, 1H), 7.46 (t, J=7.5 Hz, 1H), 3.63 (s, 3H), 1.38 (s, 12H). LCMS (M+H)$^+$: 286.

Step 2: 4-[2-(cyclopropylmethoxy)-5-methylsulfonylphenyl]-2-methylisoquinolin-1-one

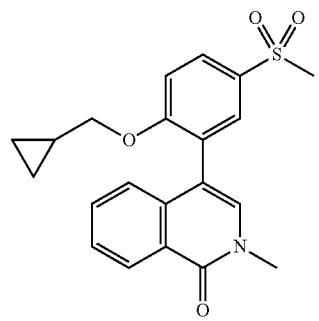 [SMILES: Cn1cc(-c2cc(S(C)(=O)=O)ccc2OCC2CC2)c2ccccc2c1=O]

(cyclopropylmethoxy)-4-methylsulfonylbenzene for 4-bromo-2-methylisoquinolin-1(2H)-one and 2-methyl-4-(4,4,5,5-tetramethyl-1,3,2-dioxaborolan-2-yl)isoquinolin-1-one for N-benzyl-2methoxy-5-(tetramethyl-1,3,2-dioxaborolan-2-yl)benzamide, 1H NMR (DMSO-d6, 400 MHz): δ 0.09 (m, 2H), 0.29 (m, 1H), 0.35 (m, 1H), 0.94 (m, 1H), 3.22 (s, 3H), 3.57 (s, 3H), 3.95 (m, 2H), 7.16 (d, J=7.9 Hz, 1H), 7.37 (d, J=8.8 Hz, 1H), 7.53 (m, 2H), 7.65 (t, J=7.6 Hz, 1H), 7.81 (d, J=2.4 Hz, 1H), 7.97 (dd, J=8.8, 2.4 Hz, 1H), 8.30 (d, J=8.1 Hz, 1H), LCMS (M+H)$^+$: 384.

Alternatively, 4-[2-(cyclopropylmethoxy)-5-methylsulfonylphenyl]-2-methylisoquinolin-1-one can be prepared as described below.

Step 1: 2-methyl-4-(4,4,5,5-tetramethyl-1,3,2-dioxaborolan-2-yl)isoquinolin-1-one

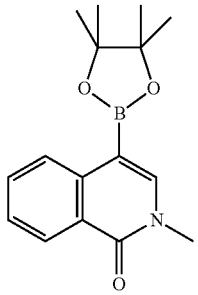 [SMILES: Cn1cc(B2OC(C)(C)C(C)(C)O2)c2ccccc2c1=O]

A mixture of 4-bromo-2-methylisoquinolin-1-one (8.0 g, 33.6 mmol), bis(pinacolato)diboron (17.1 g, 67.2 mmol), KOAc (6.6 g, 67.2 mmol), Pd$_2$(dba)$_3$ (3.1 g, 3.36 mmol) and X-Phos (1.6 g, 3.36 mmol) in anhydrous dioxane (200 mL) was stirred at 60° C. for 12 hr. The reaction mixture was concentrated and the residue was purified by column chromatography on silica gel (PE:EA=15:1) to give the title compound (6.0 g, 62%) as a solid.

Step 2: 4-[2-(cyclopropylmethoxy)-5-methylsulfonylphenyl]-2-methylisoquinolin-1-one

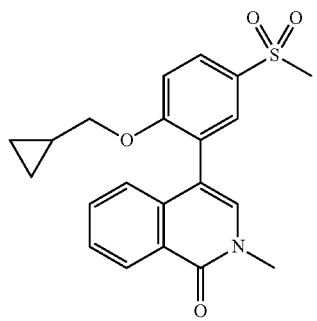 [SMILES: Cn1cc(-c2cc(S(C)(=O)=O)ccc2OCC2CC2)c2ccccc2c1=O]

The title compound from Step 1 (5.0 g, 17.5 mmol), 2-bromo-1-(cyclopropyl-methoxy)-4-methylsulfonylbenzene (0.6.4 g, 21 mmol), K3PO4 (9.3 g, 43.9 mmol) and Pd(dppf)Cl$_2$ (1.4 g, 1.75 mmol) in a dioxane/water (100 mL/10 mL) mixture were stirred at 60° C. for 12 hr. The reaction mixture was concentrated under reduced pressure and the residue was purified by column chromatography on silica gel (EA:DCM=1:4). Appropriate fractions were combined and concentrated under reduce pressure. The resultant solid was recrystallized from DCM:MTBE (1:1) (50 mL) to give the title compound (4.0 g, 60%) as a white solid. $^1$H NMR: (CDCl3, 400 MHz) δ 8.51 (dd, J1=8.0 Hz, J2=0.8 Hz, 1H), 7.98 (dd, J1=8.4 Hz, J2=2.4 Hz, 1H), 7.86 (d, J=2.4 Hz, 1H), 7.53 (m, 2H), 7.16 (d, J=7.6 Hz, 1H), 7.10 (m, 2H), 3.88 (m, 2H), 3.66 (s, 3H), 3.09 (s, 3H), 1.02-0.98 (m, 1H), 0.44-0.38 (m, 2H), 0.11-0.09 (m, 2H), LCMS: 384.1 (M+H)$^+$.

Example 2. In Vitro Inhibition Assay and In Vitro Cell-Based Assay

The IC$_{50}$ for the heterocyclic derivative BRD4 inhibitors described herein (see U.S. Pat. No. 9,034,900), including Compound A, was determined. His-tagged BRD4 was cloned, expressed and purified to homogeneity. Filipakopoulos et al., 468 Nature 1067 (2010). BRD4 binding and inhibition was assessed by monitoring the interaction of biotinylated H4-tetraacetyl peptide (AnaSpec, H4K5/8/12/16(Ac), biotin-labeled) with the target using the AlphaScreen technology (Life Technologies). In a 384-well ProxiPlate BRD4(BD1) (2 nM final) was combined with peptide (15 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20 min incubation at room temp. Alpha streptavidin donor beads and Nickel Chelate acceptor beads were added to a final concentration of 5 μg/mL. After 2 hr of equilibration, plates were read on an Envision instrument and the IC$_{50}$ was calculated using a 4-parameter non-linear curve fit. The ability of Compound A to inhibit BRD4 activity was quantified, and the respective IC$_{50}$ value was determined.

A colorimetric cellular proliferation assay (Cell-MTS assay) was performed to assess the ability of the heterocyclic derivative BRD4 inhibitors disclosed herein (see U.S. Pat. No. 9,034,900), including Compound A, to effect the proliferation of established cancer cell lines. The Cell-MTS assay is a 7-day plate-based colorimetric assay which quantifies the amount of newly generated NADH in the presence or absence of test compound. The NADH level is used for the quantification of cancer cell proliferation. Established cancer cell lines with a variety of driving mutations were obtained from American Type Culture Collection (ATCC) and routinely passaged according to ATCC protocols. For routine assay, these cells were seeded at densities which enabled about 90% confluence after 7 days of culture. Raji, human Burkitts lymphoma cells, (cMYC) were seeded at 15,000 cells per 96-well. HL-60, human proleukemia cells, (NRAS, p16, p53, c-Myc amplified) were seeded at 5,000 cells per 96-well. NCI-H460, human non-small cell lung cancer cells, (KRAS, PIK3CA, STLK11, p16) were seeded at 3.000 cells per 96-well.

Then, 24 hr after plating, cells received an 11-point dilution of test compound with final concentration ranges from 100 μM to 2.0 nM. Cells were incubated in the presence of compound for 168 hr at 37° C., and 5% CO$_2$. At the end of this incubation period, 80 μL of media was removed and 20 μL of CellTiter 96® AQueous Non-Radioactive Cell Proliferation Assay solution (Promega) was added. The cells were incubated until the OD$_{490}$ was >0.6. IC$_{50}$ values were calculated using the IDBS XLfit software package and include background subtracted OD490 values and normalization to DMSO controls. Cellular proliferation IC$_{50}$ values were uploaded and archived using the Chem Biography Platform.

The IC$_{50}$ data for 4-[2-(cyclopropylmethoxy)-5-methylsulfonylphenyl]-2methylisoquinolin-1-one in these in vitro assays is as follows:

| BRD4 IC$_{50}$ (μM) | Raji IC$_{50}$ (μM) | HL-60 IC$_{50}$ (μM) | H460 IC$_{50}$ (μM) |
|---|---|---|---|
| ≤ 5 μM | ≤ 5 μM | ≤ 5 μM | > 5 μM |

Example 3. In Vitro Pharmacology

Regulation of MYC gene expression by BRD4 has been shown in models of Burkitt's lymphoma with inhibition of BRD4, leading to growth arrest (Mertz, 2011). Similarly, in a model of lung adenocarcinoma. BRD4 inhibition was also found to be antiproliferative; however, this effect was ascribed to FOSL1 down-regulation (Lockwood, 2012). BRD4 has also been shown to regulate GLI1 gene expression, thereby modulating the Hh signaling pathway, which is known to be dysregulated in several cancer types. (Tang, 2014). The effect of Compound A treatment on MYC FOSL1, and GLI1 gene expression was evaluated by quantitative reverse transcription polymerase chain reaction (qRT PCR). Treatment with Compound A inhibited MYC gene expression in Raji Burkitt's lymphoma cells with a mean half-maximal inhibitory concentration (IC$_{50}$) value of 0.06 μM; FOSL1 gene expression in U 87 glioblastoma cells with an IC$_{50}$ value of 0.03 μM; and GLI1 gene expression in MIA-PaCa-2 pancreatic adenocarcinoma cells with an IC$_{50}$ value of 0.24 μM.

Compound A demonstrated in vitro inhibition of tumor cell growth using antiproliferative two-dimensional (2-D) cultures with cell lines and inhibition of colony formation using three-dimensional (3-D) organoid cultures with cells from PDX GBM tumor models and PDX breast cancer models.

The effect of Compound A on colony formation in fourteen PDX-derived GBM tumor models was assessed using an in vitro neurosphere assay. Compound A was tested at concentrations ranging from 0.0003 µM to 20 µM, in 3-fold increments. Colony formation was assessed after seven days of treatment by quantifying colony numbers by microscopy. Compound A inhibited colony formation in a dose-dependent manner, yielding mean half maximal inhibitory concentration ($IC_{50}$) values±standard error of the mean (SEM) ranging from 0.11±0.04 µM to 2.00±0.40 µM and spanning an 18-fold activity range. The overall mean for the GBM models was 0.62±0.13 µM.

The effect of Compound A on colony formation in four PDX-derived breast cancer models was assessed using a 3-D Matrigel-based in vitro culture system. Compound A was tested at concentrations ranging from either 0.008 µM to 5 µM or 0.0016 µM to 1 µM in 5-fold increments. Colony formation was assessed after 7 days or 14 days of treatment by quantifying colony numbers by microscopy. Compound A inhibited colony formation in a dose-dependent manner yielding a mean $IC_{50}$ value for the BR0869f estrogen receptor (ER) negative, progesterone receptor (PR) negative, and HER2/neu positive (ER-PR-Her2+) tumor model of 0.12±0.01 µM and IC50 values for the COH69, COH71, and TNBR3 triple negative breast cancer (TNBC) models of 0.07 µM, 0.18±0.02 µM, and 0.08±0.00 µM, respectively. The overall mean for the three TNBC models was 0.11±0.04 µM.

Example 4. In Vivo Pharmacology

In mouse studies, Compound A has demonstrated dose-dependent tumor growth inhibition (TGI) in patient-derived xenografts (PDX) of TNBC and GBM tumors. Additionally, using limiting dilution assays, a decrease in tumor initiating cell (TIC) frequency has been shown following treatment with Compound A (performed with a daily dosing schedule and not included in the Clinical Trial Application.

Different doses and schedules of Compound A were evaluated pre-clinically. Compound A dosed on a 3-days-on/4-days-off schedule showed TGI efficacy equivalent to that seen in the continuous dosing schedules as well as improved tolerability relative to continuous dosing schedules. Body weight, gastrointestinal (GI), and bone marrow (BM) toxicities appeared fully reversible by less frequent dosing schedules, and recovery was suitable for weekly repeat dosing.

Treatment of mice bearing COH70, a TN BC PDX tumor, with Compound A at 2 mg/kg or 10 mg/kg resulted in down-regulation of MYC. Compound A at 2 mg/kg maximally suppressed MYC expression by 51.3% at 2 hr. with MYC expression rebounding to control levels by 8 hr post-dose. Compound A at 10 mg/kg maximally suppressed MYC expression by 63.4% at 4 hr; however. MYC expression did not rebound to control levels by 24 hr post-dose. Corresponding tumor concentrations of Compound A were determined in the COH70 model at 2, 4, and 8 hrs post-dose. Maximally-measured tumor levels of Compound A were at 2 hr post-dose and were 1.3±0.3 M and 6.7±1.7 µM at 2 mg/kg and 10 mg/kg, respectively. Modulation of MYC expression levels correlated with intra-tumor concentrations of Compound A.

The TNBC PDX subcutaneous model was noted to have significant TGI in NOD/SCID gamma (NSG) mice at Compound A doses of 12.5 mg/kg, 16 mg/kg, and 20 mg/kg. Dosing was orally by gavage once daily (QD) for 3 consecutive days followed by 4 days off (designated as 3×/week in FIG. 1) (3×/week=3 consecutive days of once daily Compound A dosing followed by 4 days off; PO=by mouth; SEM=standard error of the mean) each week for 6 weeks.

Compound A was well tolerated up to a daily dose of 25 mg/kg. When tumor vols, were measured on Day 38, compared to vehicle control, the mean percent TGI of treated tumors was 64% for 12.5 mg/kg/dose group, 68% for the 16 mg/kg/dose group, and 72% for the 20 mg/kg/dose group. Mean body weights increased in all groups. Steady state pharmacokinetic parameters were determined following the final doses for the 12.5 mg/kg and 16 mg/kg dose levels. The area under the plasma concentration-time curve between 0 hr and 24 hr ($AUC_{0-24\ hr}$) of Compound A at 12.5 mg/kg was 12.003 ng·hr/mL; and at 16 mg/kg was 15,174 ng·hr/mL.

In a GBM PDX subcutaneous model. GBM15, efficacy of Compound A was shown on several schedules ranging from dosing 5-times QD weekly to twice weekly for 4 weeks (FIG. 2) (PO=by mouth; SEM=standard error of the mean). Mice bearing tumors were dosed orally QD on several schedules with the cumulative weekly Compound A dose on each schedule equal to 75 mg/kg. Dosing schedules were:

15 mg/kg Compound A for 5 consecutive days on and 2 days off (5/2), 25 mg/kg Compound A for 3 consecutive days on and 4 days off (3/4), and 37.5 mg/kg Compound A for 2 consecutive days on and 5 days off (2/5).

When tumor volumes were measured on Day 29 and compared with control vehicle, the mean percent TGI of treated tumors were 65% for the 15 mg/kg/dose (5/2) group, 65% for the 25 mg/kg/dose (3/4) group, and 70% for the 37.5 mg/kg/dose (2/5) group. Minimal weight loss was seen in all groups (vehicle group=−1.2%; 15 mg/kg/dose group=−6.6%; 25 mg/kg/dose group=−3.7%; and 37.5 mg/kg/dose group=−3.1%).

Xenograft models of NUT Midline Carcinoma (NMC) in mice are studied. Matched cohorts of mice with established tumors are randomized to treatment with a test compound (either Compound A, or temozolomide, or a formulation comprising both Compound A and temozolomide) or vehicle, administered by daily intraperitoneal injection. Before randomization and after 4 days of therapy, mice are evaluated by $^{18}$F-fluorodeoxyglucose (FDG)-PET imaging. Tumor-volume, toxicity, or weight loss are measured. Tumors are obtained and sectioned and examined immunohistochemically for the BRD4-NUT oncoprotein, cell spreading, keratin expression, nuclear Ki67, and TUNEL staining. Paired samples from treated and untreated mice are prepared and analyzed using standardized protocols and commercially available software (i.e., ImageScopt; Aperio Technologies).

Example 5. Antitumor Efficacy in Xenograft Model of MCF-7 Breast Cancer

Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 µL/animal) on the right flank 2-3 days post-pellet implantation and tumor vol. (length× width 2/2) is monitored biweekly. When tumors reach an average volume of ~200 mm³, animals are randomized and treatment is started. Animals are treated with a test compound or vehicle daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 6. Antitumor Efficacy in Raji Human Burkitts Lymphoma Model

Procedure: Female SCID CB17 mice (6-8 weeks old, Charles River Lab) were inoculated subcutaneously in the right flank region with Raji cells (at $3.5 \times 10^6$ cells/mouse) and the tumor was allowed to grow to approximately 150 mm$^3$. Mice were then randomized into treatment cohorts (N=8) and treated orally once daily with vehicle control or test compound for 21 days. Test compound was administered as a suspension in 1% Tween 80, 40% PEG400, and either 59% of 0.5% HPMC, or 9% DMSO+50% of 0.5% HPMC, at doses ranging from 5 mg/kg to 50 mg/kg. Tumor length and width were measured in millimeters three times per week. Tumor volumes were calculated by the formula V=(L×W×W)/2. Tumor growth inhibition (TGI) was calculated with the formula: TGI=100−(median tumor volume of treatment group/median tumor volume of vehicle control group)×100. TGI measurements were performed until the volume of a tumor in the control group reached 3.000 mm$^3$. Statistical analysis was performed using 2-tailed T-test. P values <0.05 were considered as statistically significant. TGI was determined to range from 42% to 80%.

Example 7. Synergistic Effects of Compound A and Temozolomide in a Temozolomide-Resistant Xenograft GBM Model O-6-methylguanylmethyltransferase (MGMT) has been implicated in GBM resistance to the alkylating DNA damage of temozolomide (TMZ). GBM3 is a GBM PDX subcutaneous model with high MGMT expression by PCR, a non-methylated MGMT promoter, and has the phenotype of being resistant to TMZ. In previous studies of neurospheres cultured from GBM3, RT-PCR analysis showed that Compound A, in a dose-responsive manner, downregulated expression of MGMT. When mice bearing GBM3 were given a single dose of Compound A at 20 mg/kg, qRT-PCR revealed down-regulation of MGMT in the harvested tumor. This led to an efficacy experiment to understand whether Compound A could sensitize TMZ-resistant GBM to TMZ, and exhibit synergistic effects compared with either compound administered alone.

Figure 3:
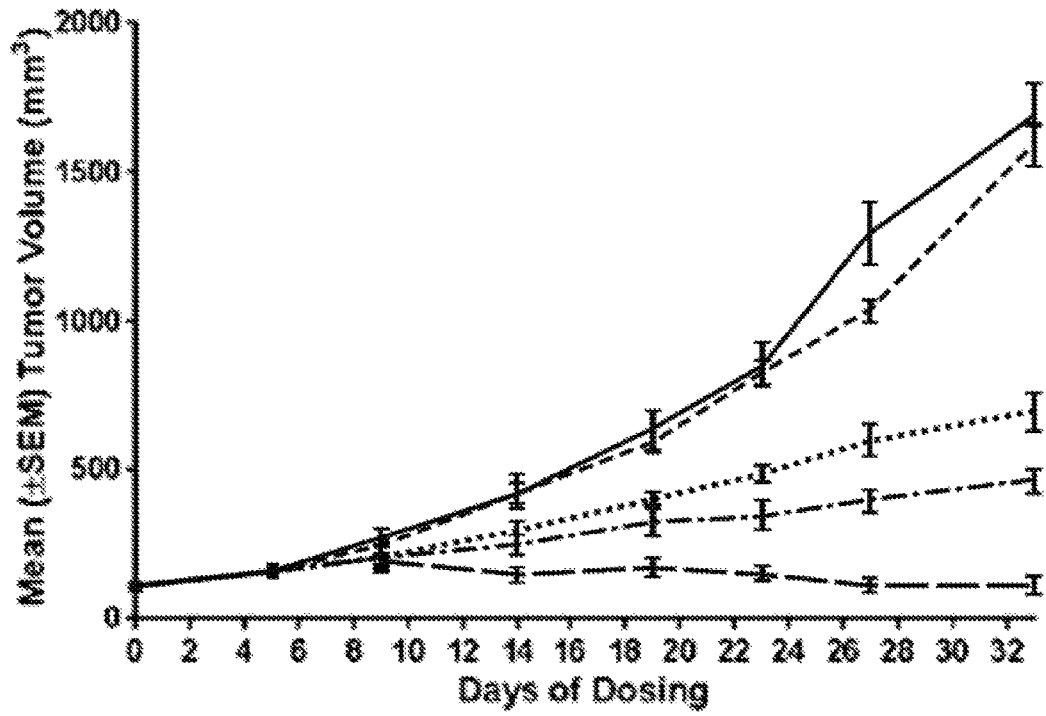
FIG. 3 is a graph showing tumor growth inhibition of GBM3 (GBM PDX) xenografts by administration of either Compound A, temozolomide (TMZ), or a combination of Compound A and TMZ. —— Vehicle; - - - - Compound A 12 mg/kg PO once daily; - —— - —— Compound A 6 mg/kg PO twice daily; —— —— Compound A 6 mg/kg PO twice daily combined with TMZ 50 mg/kg IP (intraperitoneal injection) given on days 7-9 and 22-24; - - - TMZ 50 mg/kg IP given on days 7-9, 22-24; SEM is the standard error of the mean.

Cohorts of NSG mice bearing GBM3 were treated with TMZ 50 mg/kg intraperitoneal (IP)×3 Q2 weeks; Compound A 6 mg/kg orally twice daily (BID) or 12 mg/kg orally once daily; or with a combination of Compound A 6 mg/kg orally BID and TMZ 50 mg/kg IP×3 Q2 weeks. Significant tumor growth inhibitions, as measured by tumor volumes, were observed following dosing with Compound A alone or in combination with TMZ (FIG. 3). TMZ alone did not induce significant TGI when given alone (3%). Compound A alone induced significant TGIs of 63% (12 mg/kg QD) and 76% (6 mg/kg BID). The combination of Compound A and TMZ demonstrated synergy, however, and was significantly superior to all other regimens in terms of TGI. Moderate weight loss was observed during part of the study course (nadir −5.1%) in the combination group; but body weight loss recovered, and all treatment groups exhibited net gain in mean body weight at study end.

Example 8. Oral Dosage Form

A tablet is prepared by mixing 48% by weight of Compound A. or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 9. Nonclinical Pharmacokinetics and Drug Metabolism

As described herein, a battery of in vitro and in vivo studies have been conducted to characterize the absorption. PK, distribution, metabolism and elimination of Compound A. Robust and reproducible bioanalytical methods for the quantitation of Compound A levels were developed and used in PK and toxicokinetic studies. Human PK parameters and exposures were predicted using allometric scaling.

Pharmacokinetics and oral bioavailability of Compound A were evaluated in Sprague-Dawley rats and Beagle dogs. The systemic clearance was low (~5%-13% of liver blood flow) in both male and female rats, but males showed approximately 2-fold higher clearance than females. The volume of distribution ranged from about 1- to 3-fold the total body water volume, suggesting distribution of Compound A into tissues. The mean oral bioavailability of Compound A was 40% in rats and 76% in dogs. Due to differences in systemic clearance between male and female rats and in order to obtain comparable systemic exposure in toxicology studies, Compound A doses administered to male rats were 3-fold higher than to female rats. Toxicokinetics of Compound A in rats and dogs showed no sex differences in systemic exposure, dose-proportional increase in systemic exposure, no accumulation in rats, and up to 3-fold accumulation in dogs after repeat dosing. Compound A showed limited brain distribution with brain to plasma ratios of 0.14 to 0.16 in tumor-bearing NSG mice.

Using the allometry-derived PK parameters and an assumption of 62% oral bioavailability (the average observed in pre-clinical species), the predicted steady state systemic exposure (AUC0 24 hr) of Compound A in humans following weekly (3 days on/4 days off) administration of a 15 mg oral dose can range from 731 to 2263 ng·h/mL. No notable differences in plasma protein binding of Compound A were observed in plasmas derived from preclinical species (89.9% to 93.3%) and human sources (90.2%).

Metabolism of Compound A was evaluated in vitro using human hepatocytes and a single metabolite, namely the N-desmethyl derivative was identified. This metabolite was observed in rat, dog and monkey hepatocytes. No unique human metabolites were identified. Studies using recombinant cytochrome P450 (CYP) enzymes suggest that multiple CYP enzymes (CYP2C9, CYP2C19 and CYP3A4) are capable of metabolizing Compound A; yet the relative contribution of the individual enzymes is unknown.

29 In vitro, Compound A does not inhibit CYP1A2 and CYP3A4. Compound A caused inhibition of CYP2C9, CYP2C19, and CYP2D6 with IC50 values of 13.9 µM, 26.7 µM, and 54.3 µM, respectively. In hepatocytes, Compound A (up to 10 µM) is not an inducer of CYP1A2, CYP2B6, or CYP3A4. Hence, at clinically relevant concentrations. Compound A has minimal potential to cause drug-drug interactions with co-administered drugs that are CYP substrates.

In rats, following intravenous (IV) administration of non-radiolabeled Compound A, an average of 0.9% of the dose was excreted intact either in bile or urine, indicating that excretion of intact drug is not the primary mode of elimination and that metabolism may play a major role in disposition of Compound A.

Example 10. Nonclinical Toxicology

Compound A was evaluated in non-GLP exploratory toxicology and genetic toxicology studies, and in GLP repeat-dose (≤4-week nonclinical toxicology) studies. GLP 4-week oral toxicity studies (with a 4-week recovery period) were conducted in rats (0, 5, 10, or 20 mg base/kg/dose for females, and 0, 15, 30, or 60 mg base/kg/dose for males), and Beagle dogs (0, 1.75, 3.75, or 7.5 mg base/kg/dose). The dosing schedule was once daily administration for 3 consecutive days followed by 4 consecutive days off drug each week for a total of 4 weeks.

In rats, the primary target tissues of toxicity are those that make up the gastrointestinal (GI) tract, bone marrow, lymphoid organs, testes, and bone. In dogs, the primary target tissues of toxicity are those that make up the GI tract, bone marrow, lymphoid organs, and testes.

In the 4-week rat study, the ≥20 mg base/kg/dose was severely toxic. This dose resulted in the death or moribund sacrifice of animals as early as Day 6, ultimately leading to termination of dosing and sacrifice of the surviving 60 mg base/kg/dose group animals (males) on Day 11; and the termination of dosing and sacrifice on Day 11 of the surviving 20 mg base/kg/dose group animals (females) (N=9) or start of recovery phase for (N=4). There were no Compound A-related mortalities at doses below 20 mg base/kg/ dose. There were no adverse findings at the low dose level (5 mg base/kg/dose [females], 15 mg base/kg/dose [males]).

Regarding toxicity, based upon the constellation of clinical, laboratory, gross pathologic, and histopathologic findings, the severely toxic dose in 10% of the rats (STD10) was 20 mg base/kg/dose in females and 30 mg base/kg/dose in males. For any clinical trial, the overarching STD10 should be considered 20 mg base/kg/dose. Due to the lack of adverse findings, the no-observed-adverse-effect level (NOAEL) in females was 5 mg/kg/dose and in males was 15 mg/kg/dose. For any clinical trial, the overarching NOAEL should be considered 5 mg base/kg/dose. These values apply to the three-days-on/four-days-off Compound A dose schedule. Evaluation of recovery animals demonstrated that all test article related findings were reversible after a period of 4 weeks from the cessation of dosing (with the exception of the testis-related findings which could not be evaluated due to the moribund sacrifice of the 60 mg base/kg/dose group males originally designated to evaluate reversibility).

Safety pharmacology evaluations, i.e., functional observational battery (FOB), were also performed to determine the potential central nervous system effects of Compound A as part of the GLP 4-week repeat-dose toxicity rat study. There were no Compound A-related FOB effects.

In the 4-week Beagle dog study, the severely toxic dose was 7.50 mg base/kg/dose. This dose resulted in the moribund sacrifice of animals (4 males and 1 female) as early as Day 11, ultimately leading to termination of dosing of the surviving 7.50 mg base/kg/dose group males, and the start of recovery phase for the surviving 7.50 mg base/kg/dose group males. There were no Compound A-related mortalities at doses below 7.50 mg base/kg/dose, but there were Compound A-related findings at all doses evaluated.

Based upon the constellation of clinical, laboratory, gross pathologic, and histopathologic findings, 3.75 mg base/kg/ dose was established as the highest non-severely toxic dose (HNSTD); no NOAEL was identified. These values apply to the 3-days-on/4-days-off dose schedule. At the lowest dose (1.75 mg base/kg/dose), adverse findings were limited to decreased thymus weights and testicular/epididymal toxicity. Evaluation of recovery animals demonstrated that all test article-related findings were reversible after a period of four weeks from the cessation of dosing with the exception of the testis- and epididymis-related findings.

Safety pharmacology evaluations were performed to determine the potential cardiovascular and respiratory effects of Compound A in conscious Beagle dogs as part of the GLP 4-week repeat-dose toxicity study. There were no Compound A-related effects on electrocardiograms, heart rate, or respiratory rate.

An in vitro human ether-A-go-go-related gene (hERG) study identified an $IC_{50}$ of 24.3 μM. In a non-GLP bacterial reverse mutation assay (Ames), Compound A was determined to be non-mutagenic.

Overall, Compound A exhibits an acceptable safety profile in preclinical species for an oncology clinical candidate, and the toxicology program for Compound A adequately supports the conduct of clinical trials in cancer patients.

Example 12. Safety and Tolerability of Compound A in Humans

Compound A is a new investigational product that has a strong biological rationale for the treatment of subjects with solid tumors and NHLs. The safety and tolerability of Compound A in humans, as well as the biologic and clinical activity, are evaluated in a clinical study.

Because no clinical studies have been conducted with Compound A, the efficacy and safety profiles of Compound A in humans are unknown. Potential toxicities for Compound A are identified based on nonclinical studies with Compound A. The safety profiles of two BET inhibitors tested in Phase I first-in-human (FIH) studies reveal good tolerability with continuous daily dosing for 14 days in each 21-day cycle with thrombocytopenia as major DLT (Abramson, 2015; Herait, 2015) or GI tract toxicity (mainly diarrhea) as DLT (Dombret, 2014; Herait, 2015).

The frequency and caliber of safety assessments proposed for Compound A-ST001 are typical of those expected for a FIH study and consistent with findings on toxicological studies of Compound A in rats and dogs. In rats and dogs, the primary target tissues of toxicity were the GI tract, bone marrow, lymphoid organs, and testes. The overall preclinical and the histopathology data suggest that the GI system may be the key target of Compound A mediated toxicity.

Frequent early monitoring of subjects' weight, hydration status, serum electrolytes, the incidence and severity of diarrhea and emesis, as well as episodes of abdominal pain (gastric, intestinal) are critical components of the safety monitoring plan and implementation of aggressive supportive care measures for the early onset (i.e., Grade 1) of nausea, vomiting or diarrhea are highly recommended. Based on the morphologic changes, flattening of the intestinal villi, and the mucosal erosions observed in the GI tract of rats and dogs, subjects with malabsorption syndromes, active ulcer/gastritis, or recurring episodes of GI bleeding will be excluded from enrollment. Mucosa coating agents for protection of esophageal/gastric mucosa will be recommended at the discretion of the Investigator as well as monitoring subjects for GI bleeding. Subjects will be encouraged to report episodes of GI discomfort or pain, appetite loss, or blood in stool.

Bone marrow hypocellularity and lymphoid tissue (thymus, spleen, lymph nodes) depletion findings emphasize the importance of frequent blood count monitoring, with platelets and white blood cell (WBC) differential. Subjects are monitored for possible toxicity through standard and specialized laboratory tests including complete blood counts, prothrombin time (PT)/activated partial thromboplastin time (APTT)/international normalized ratio (INR), and serum chemistries.

Figure 7:
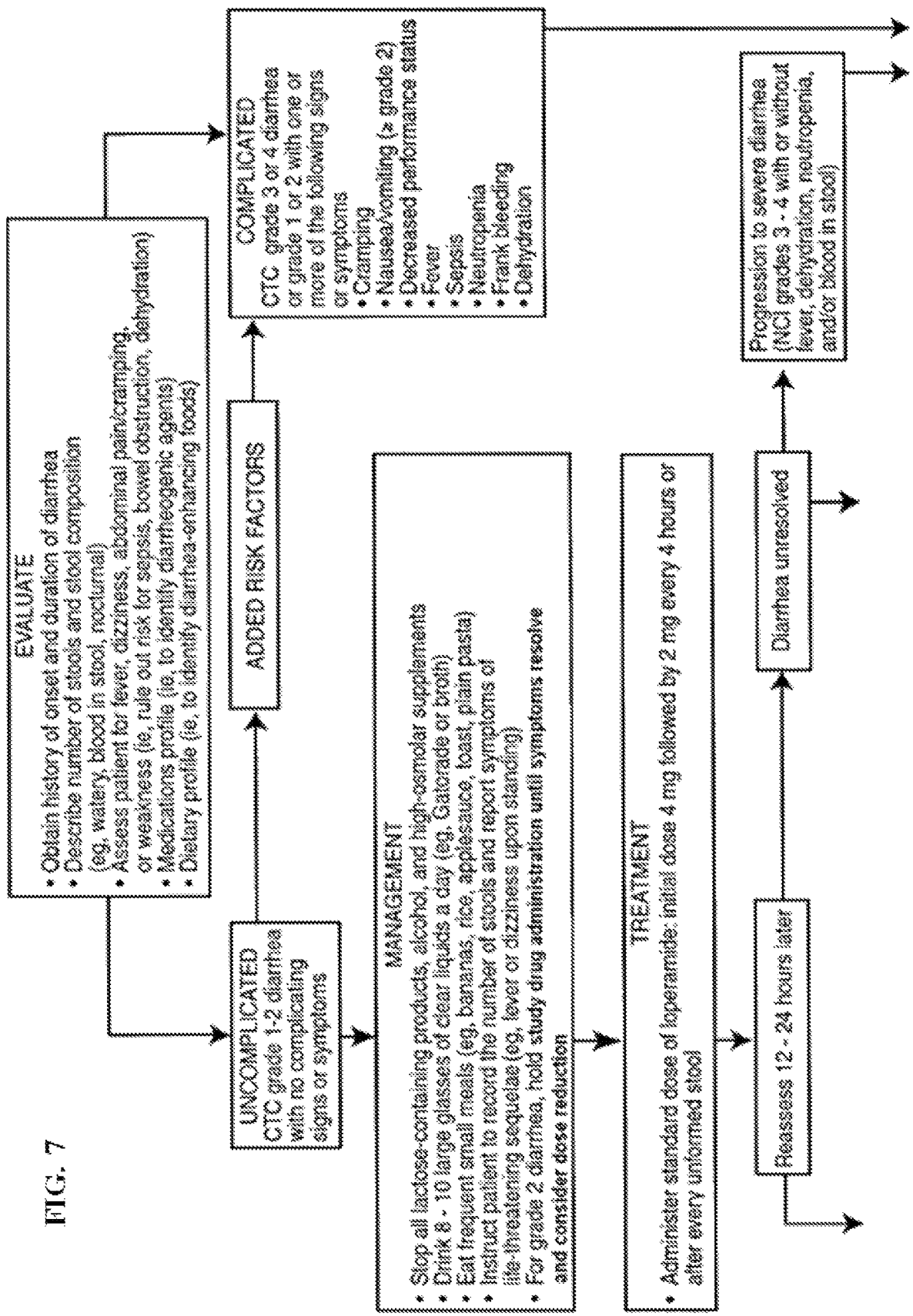
FIG. 7 is a scheme showing published recommendations for management of treatment-induced diarrhea (Benson et al., 22 J. Clin. Oncol. 2918 (2004)), modified for consistency with a study protocol.
Figure 7:
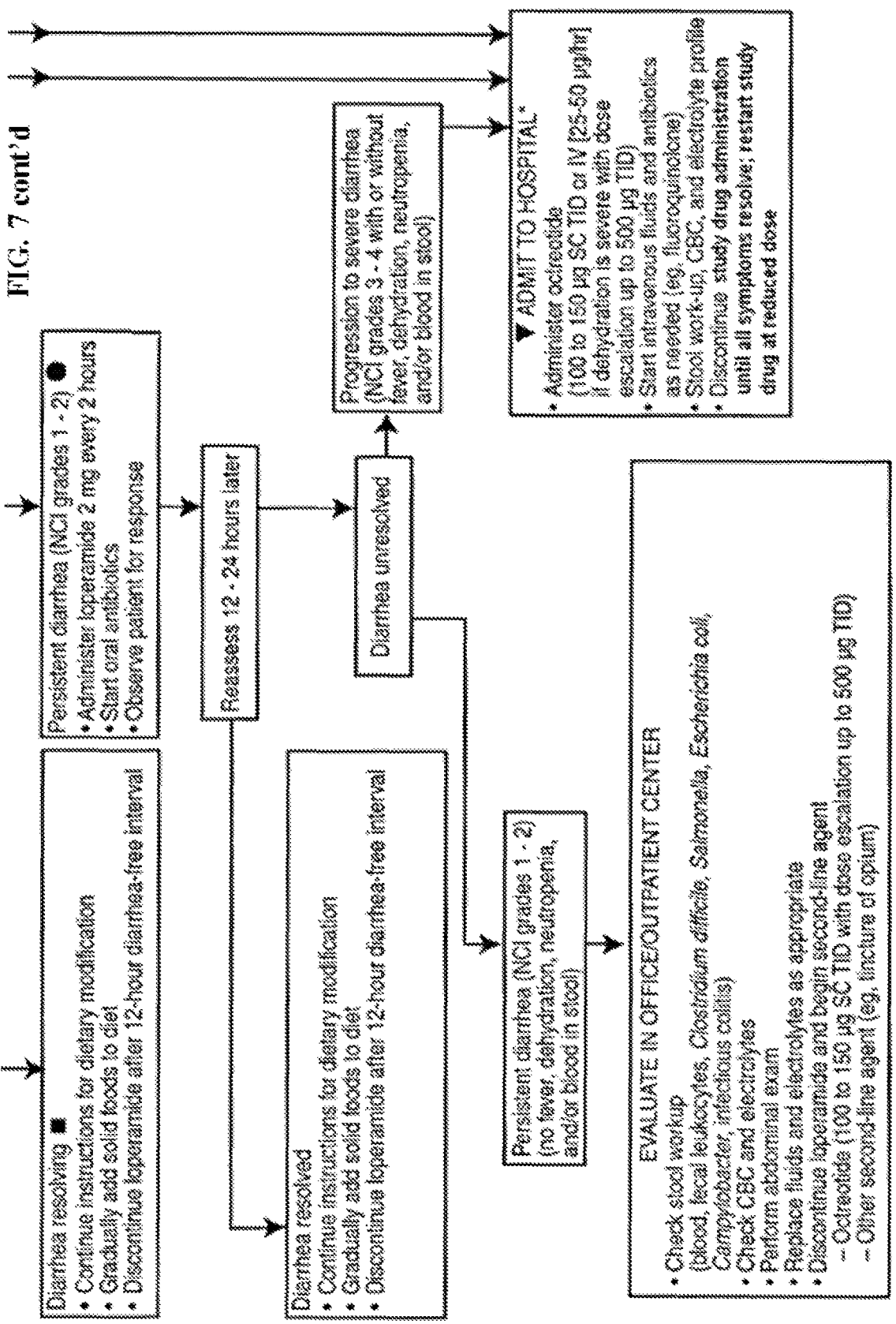

Transient changes in blood glucose were observed in only a few occasions in the nonclinical toxicology studies with Compound A. Furthermore, preliminary clinical data of a new investigational BETi, OTX015, reported 7 of 37 patients with non-leukemic hematologic malignancies experienced Grade 1-2 hyperglycemia and 1 patient experienced Grade 3 hyperglycemia (Thieblemont, 2014). It is unknown whether hyperglycemia might be observed with Compound A in humans and the standard laboratory panel includes fasting glucose measurements. General guidelines for the management of possible hyperglycemia are provided in FIG. 7.

The histopathological findings in testis- and epididymis of male rats and dogs will warrant prohibition of semen donation and fathering children for the duration of the clinical study as well as for at least 3 mos after the last study dose. There were no histologic lesions in reproductive organs of female animals in the nonclinical studies. The significance of this preclinical finding and the potential and relative clinical risk is unknown at this time. Developmental and reproductive toxicology studies have not been conducted with Compound A. Subjects are required to follow the pregnancy prevention guidelines as described herein.

As this is a FIH study, subjects with a history of heart failure, ischemic heart disease, uncontrolled hypertension, serious cardiac arrhythmias, or long QT interval on ECG are excluded from enrollment. All study subjects require documentation of adequate left ventricular ejection fracture (>45%) at baseline As detailed herein, the study is conducted in two parts: dose escalation (Part A) and dose expansion (Part B).

In Part A, a Bayesian logistic regression model (BLRM) utilizing escalation with overdose control (EWOC) guides dose escalations to an estimated MTD for Compound A. Babb 1998. Neuenschwander 2008. Traditional escalation designs (e.g., 3+3, rolling six, accelerated titration) were designed for cytotoxic agents and doses escalation decisions were based on toxicity rates with the underlying assumption that efficacy and toxicity increase with dose. Newer molecular targeting agents may have differing dose-toxicity and dose-efficacy curves and a design based on utilizing more than just toxicity data may be more effective in determining the recommended dose. Tourneau et al., 101 J. Natl. Cancer Inst. 708 (2009); Ivy et al., 16 Clin. Cancer Res. 1726 (2010).

The statistical model based approach (BLRM with EWOC) allows for nonclinical data to be utilized in combination with observed clinical data (e.g., toxicities, pharmacodynamic, pharmacokinetic, efficacy, etc.) in the assignment of each subject to a dose level and can potentially decrease the number of subjects treated at subtherapeutic or intolerable doses. Tourneau et al., 7 PLoS ONE e51039 (2012). The use of EWOC provides rules or restrictions to avoid dosing beyond the MTD. Additional details of the design are presented below. One or more dosing regimens and/or disease subsets may be selected for cohort expansion in Part B to obtain additional safety and efficacy information for larger cohorts of subjects (up to about 20 in each cohort).

Based on the doses and exposures at which the principal treatment-related effects occurred in the GLP-compliant, 4-week rat and dog studies, both species are considered of similar sensitivity to the toxicities associated with Compound A administration. The proposed human starting dose is 15 mg Compound A base, once daily for 3 consecutive days followed by 4 consecutive days off drug every week (3/7 day dose schedule). This Compound A dose was calculated using the approach described in the ICH Harmonised Tripartite Guideline S9, *Nonclinical evaluation for anticancer pharmaceuticals* (2009), and is summarized in Table 3:

TABLE 3

Proposed Clinical Starting Dose of Compound A Based on the Severely Toxic Dose in 10% of the Rats and the Highest Non-severely Toxic Dose in the One-Month Toxicity Study in Dogs

| Species | Rat STD10 or Dog HNSTD (mg base/kg) | HED (mg base/kg) | HED (mg base/kg) | Safety Factor | HED/Safety Factor (mg base)[a] | Proposed Clinical Starting Dose (mg base)[b] |
|---|---|---|---|---|---|---|
| Rat | 20 | 3.2 | 194 | 10 | 19 | 15 |
| Dog | 3.75 | 2.1 | 125 | 6 | 21 | |

HED = human equivalent dose; HNSTD = highest non-severely toxic dose; STD10 = severely toxic dose in 10% of the animals.
[a]Based on HED conversion factor for a 60-kg person from the FDA Guidance for Industry, *Estimating the Maximum Safe Starting Dose in Initial Clinical Trials for Therapeutics in Adult Healthy Volunteers* (FDA, 2005) and the ICH S9 Guideline, *Nonclinical Evaluation for Anticancer Pharmaceuticals* (ICH, 2009).
[b]Using allometry derived plasma clearance (mL/h/kg) and volume of distribution (L/kg) estimates and assuming X % oral bioavailability (based on the average from preclinical species), the predicted $C_{max}$ and $AUC_{24\,h}$ at the intended human starting dose of 15 mg are approximated.
See also CDER, *Guidance for Industry: Estimating the maximum safe starting dose in initial clinical trials for therapeutics in adult healthy volunteers* (July 2005).

The proposed starting dose in humans is lower than 1/10th the STD10 in rats, less than 1/6th the HNSTD in dogs, and is considered safe based on multiples of exposure (as measured by AUC) in rats and dogs relative to the predicted human exposure at a dose of 15 mg Compound A base. As noted in Table 1, the human exposure at 15 mg base is predicted to range from 736 to 2263 ng·hr/mL; these values are approximately 23-fold to 72-fold lower than the mean exposure corresponding to the rat STD10 (52800 ng·hr/mL) and approximately 4-fold to 14-fold lower than the mean exposure corresponding to the dog HNSTD (10000 ng·hr/mL). Based on these toxicokinetic data, the proposed human starting dose of 15 mg Compound A base is expected to be safe.

A key exploratory objective of this study is to identify a dose of Compound A that is not only safe but that exhibits pharmacologic activity. A set of genes has been identified whose expression is decreased upon ex vivo treatment with Compound A in peripheral blood mononuclear cells (PBMCs) and in whole blood. In the present study, changes in the expression of these genes in whole blood or other genes in tumor biopsy may provide confirmation that a dose is pharmacologically active and could help distinguish which dose shows the most compelling pharmacologic activity.

Predictive biomarkers allow prospective identification of patients who are likely to benefit clinically from Compound A as a single agent or combined with other agents. Although the predictive diagnostic analyses in the current trial are exploratory in nature, they reveal associations between biomarkers and responses that could provide a basis for future diagnostically driven studies.

Different tumor types are selected for the Compound A dose expansion cohorts in Part B depending on the results from Part A of the study, pre-clinical efficacy, and supportive literature. As a reversible inhibitor of BET family members, an expansion cohort of subjects with locally advanced basal cell carcinoma (BCC) is enrolled in Part B.

BRD4 and other BET bromodomain proteins regulate GLI1 transcription downstream of SMO, with BRD4 directly occupying GLI1 and GLI2 promoters. Tang, 2014. This occupancy can be inhibited by BET inhibitors, and the BET inhibitor, JQ1, decreases tumor cell proliferation in vitro and in vivo in Hh-driven tumors, even those resistant to SMO inhibition. Tang, 2014. Hence clinical investigation of a BET inhibitor in locally advanced or metastatic BCC subjects with de novo or acquired resistance is warranted. Similarly, the clinical investigation of the BET inhibitor Compound A for antineoplastic activity in a variety of malignancies is warranted. This Example provides a study of Compound A in humans, designed to evaluate drug safety and pharmacokinetic profiles with various dose levels/regimens, and also detects initial signals of drug efficacy in order to advance development of Phase 2 clinical trials.

More specifically, a study of Compound A includes an open-label, Phase 1a, dose escalation and expansion, First-In-Human (FIH) clinical study of Compound A in subjects with advanced solid tumors, or relapsed or refractory NHLs. The dose escalation part of the study (Part A) explores escalating oral doses of Compound A to estimate the MTD and/or RPTD of Compound A. A BLRM utilizing EWOC (see Babb, 1998; Neuenschwander 2008) helps guide Compound A dose escalation decisions with the final decisions made by a scientific review committee (SRC). The expansion part of the study (Part B) further evaluates the safety and efficacy of Compound A administered at or below the MTD in a selected expansion cohorts of up to approximately twenty evaluable subjects, each in order to further define the RP2D. One or more dosing regimens or disease subsets may be selected for cohort expansion. Parts A and B consist of three periods: Screening, Treatment, and Follow-up periods (see FIG. 4). Study Objectives are summarized in Table 1, and Study Endpoints are summarized in Table 2, above.

Typically, the screening period starts 28 days prior to first dose of Compound A. The informed consent document (ICD) is signed and dated by the subject and the administering staff prior to the start of any other study procedures. All screening tests and procedures are completed within the 28 days prior to the first dose of Compound A.

During the treatment period, formulations comprising Compound A is initially administered orally once daily for 3 consecutive days followed by 4 consecutive days off drug every week (3/7-day dose schedule) in each four-week cycle. Alternate dosing schedules (e.g., 2-days-on/5-days-off, each week) are examined based on the SRC review of available safety, PK, pharmacodynamic (PD), and efficacy data. In Part A, the window for evaluation of dose-limiting toxicity (DLT) is 28 days (4 weeks) during Cycle 1.

In the follow-up period, all subjects are followed for 28 days (±2 days) for safety, after the last dose of Compound A. Subjects who discontinue treatment for reasons other than disease progression (or relapse), start of a new anticancer therapy, or withdrawal of consent from the entire study, have disease assessments performed according to the specified tumor assessment schedule until progression or initiation of new systemic anticancer therapies. After the safety follow-up visit, all subjects are followed every subsequent 3 mos (±2 wks) for survival follow-up for up until 2 yrs or until death, lost to follow-up, or the end of trial, whichever occurs first.

For Part A, Dose Escalation, a minimum of 3 subjects are enrolled at each dose level. The initial Compound A dose is 15 mg. The BLRM with EWOC incorporates available prior safety information and updates the model parameters after each new cohort of subjects completes Cycle 1. The decision for the next dose is made by the SRC based on a calculation of risk assessment using the BLRM, and available safety (i.e., DLT and non-DLT safety data), PK, PD, and efficacy information. In addition, relevant non-clinical data (e.g., GLP toxicity studies, in vivo pharmacology from xenograft models, etc.) may be utilized in the assessment. Details of the statistical methodology are provided below.

At all decision time points, the BLRM permits alterations in the dose increments based on the observed DLTs. The dose for the next cohort, however, does not exceed a 100% increase from the prior dose. The MTD is the highest dose that is unlikely (<25% posterior probability) to cause DLT in ≥33% of the treated subjects in the first cycle of Compound A treatment. The SRC makes the final decision regarding the Compound A dose for each cohort.

During dose escalation, a Compound A dose can be declared the MTD and/or RP2D after meeting the following conditions: at least six evaluable subjects have been treated at the dose; the posterior probability of targeted toxicity at the dose exceeds 60% and is the highest among the escalation doses or a minimum of 21 subjects have been treated on the study; and the dose is recommended according to the BLRM and the SRC approves it.

The SRC includes Investigators (or designated representatives), the Sponsor's study physician, safety physician, study statistician, and the study manager. Ad hoc attendees may include the study pharmacokineticist and additional study clinical scientists. Other internal and external experts are consulted by the SRC, as necessary.

The decision to evaluate additional subjects within a dose cohort, a higher dose cohort, intermediate dose cohorts, smaller dose increments, alternate dosing schedules (e.g., 2-days-on/5-days-off, each week), or declare an MTD, is also determined by the SRC based on the BLRM assessment and their review of available safety (i.e., DLT and non-DLT data), PK, PD, and efficacy information. The final decision is made by the SRC.

After the first dose is administered in any cohort during dose escalation, subjects in each cohort are observed for 28 days (Cycle 1, DLT window) before the next dose cohort can begin. No more than one subject per day is enrolled in a given dose escalation cohort. Subjects non-evaluable for DLT are replaced. A subject evaluable for DLT is defined as one that: Has received at least 10 of 12 doses (or ≥80% of the total planned dose intensity) of Compound A during Cycle 1 without experiencing a DLT; or Experienced a DLT after receiving at least one dose of Compound A.

Intra-subject dose escalation is not allowed during the DLT assessment period. In Cycles ≥3, however, subjects without evidence of disease progression who are tolerating their assigned dose of Compound A may (at the Investigator's discretion and in consultation with the study's medical monitor) escalate to the highest dose level shown to be adequately tolerated by at least one cohort of subjects in this study (i.e., when overdose risk is less than 25% based on the BLRM assessment).

Regarding Part B-Cohort Expansion, following completion of dose escalation (Part A), selected tumor cohorts are enrolled into an expansion phase (Part B) with up to approximately 20 evaluable subjects each. Expansion may occur at the MTD and schedule established in the dose escalation phase, or at an alternative tolerable dose and schedule, based on review of available safety, PK, PD, and efficacy data from Part A. The SRC selects the doses and schedules of interest for cohort expansion. One or more dosing regimens may be selected for cohort expansion. The SRC continues reviewing safety data regularly throughout the study, and recommends study continuation and dose modification, as appropriate.

Regarding enrollment of the study population, men and women, 18-years or older, with advanced or unresectable solid tumors and relapsed or refractory NHLs (DLBCL and iNHL) are enrolled in the study. Enrollment is expected to take ~30 mo to complete (12-18 mo for dose escalation and 9-12 mo for expansion). Completion of active treatment and post-treatment follow-up is expected to take an additional 4-28 mo. The entire study is expected to last approximately 4 years. The End-of-Trial is defined as either the later date of the last visit of the last subject to complete the post-treatment follow-up, or the date of receipt of the last data point from the last subject that is required for primary, secondary or exploratory analysis, as pre-specified.

Study treatment may be discontinued if there is evidence of clinically significant disease progression, unacceptable toxicity or subject/physician decision to withdraw. Subjects may continue to receive study drug beyond disease progression at the discretion of the Investigator in consultation with the Medical Monitor.

In at least one embodiment, Compound A is formulated tablets for oral administration. Labeling is appropriate. e.g., for investigational use as per the regulations of the relevant country health authority.

For key efficacy assessments, subjects are evaluated for efficacy after every two cycles through Cycle 6, and thereafter every three cycles. All subjects who discontinue treatment for reasons other than disease progression, start of a new anticancer therapy, or withdrawal of consent from the entire study are followed until progression or initiation of new systemic anticancer therapies.

Tumor response is determined by the Investigator. For solid tumors, assessment is based on Response Evaluation Criteria in Solid Tumors (RECIST 1.1). Eisenhauer et al., 45 Eur. J. Cancer 228 (2009). For NHLs, assessment is based on the International Working Group Revised Response Criteria for Malignant Lymphoma. Cheson et al., 25 J. Clin. Oncol. 579 (2007). [18F]-fluorodeoxyglucose (FDG) positron emission tomography (PET) or FDG PET/CT imaging is required to confirm a complete response in subjects with FDG-avid tumors.

The safety variables for this study include adverse events, safety clinical laboratory variables, 12-lead electrocardiograms. Eastern Cooperative Oncology Group Performance Status, left ventricular ejection fraction assessments, physical examinations, vital signs, exposure to study treatment, assessment of concomitant medications, and pregnancy testing for females of child bearing potential. The PK profiles of Compound A are determined from serial blood collections.

No clinical studies have been conducted with Compound A and therefore the efficacy and safety profiles of Compound A in humans are unknown. Potential toxicities for Compound A are being identified based on nonclinical studies with Compound A. The frequency and caliber of safety assessments proposed for Compound A-ST-001 are typical of those expected for a FIH study and consistent with findings on toxicologic studies of Compound A in rats and dogs. In rats and dogs, the primary target tissues of toxicity were the GI tract, bone marrow, lymphoid organs, and testes. The overall pre-clinical and the histopathology data suggest that the gastrointestinal system may be the key target of Compound A-mediated toxicity.

Frequent early monitoring of subjects' weight, hydration status, serum electrolytes, the incidence and severity of diarrhea and emesis, as well as episodes of abdominal pain (gastric, intestinal) are components of the safety monitoring plan and implementation of aggressive supportive care measures for the early onset (i.e., Grade 1) of nausea, vomiting or diarrhea are recommended. Based on the morphologic changes, flattening of the intestinal villi, and the mucosal erosions observed in the GI tract of rats and dogs, subjects with malabsorption syndromes, active ulcer/gastritis, or recurring episodes of GI bleeding may be excluded from the study. Mucosa coating agents for protection of esophageal/gastric mucosa are recommended at the discretion of the Investigator, as well as monitoring subjects for GI bleeding. Subjects are encouraged to report episodes of GI discomfort or pain, appetite loss, or blood in stool.

In a FIH study, subjects with a history of heart failure, ischemic heart disease, uncontrolled hypertension, serious cardiac arrhythmias, or long QT interval on ECG may be excluded from enrollment. All study subjects require documentation of adequate left ventricular ejection fracture (>45%) at baseline. Waivers to the protocol are not granted during the conduct of this trial, under any circumstances.

Bone marrow hypocellularity and lymphoid tissue (thymus, spleen, lymph nodes) depletion findings emphasize the importance of frequent blood count monitoring, with platelets and WBC differential. Subjects should be monitored for possible toxicity through standard and specialized laboratory tests including complete blood counts, prothrombin time (PT)/partial thromboplastin time (PTT)/international normalized ratio (INR), and serum chemistries.

The histopathological findings in testis- and epididymis of male rats and dogs warrant the prohibition of semen donation and fathering children for the duration of the clinical study as well as for at least 3 months after the last study dose. There were no histologic lesions in reproductive organs of female animals in the nonclinical studies, although the significance of this was unknown. Developmental and reproductive toxicology studies have not been conducted with Compound A. Subjects will be required to follow the pregnancy prevention guidelines.

Pharmacodynamic (PD) assessments are described below. A primary objective of this study evaluates the safety and tolerability of treatment with pharmaceutical formulations comprising Compound A, including the determination of the MTD or RP2D. The analysis method for estimating the MTD is the BLRM guided by the EWOC principle (Babb, 1998; Neuenschwander, 2008).

Statistical analyses are performed by dose level (Part A) and tumor cohort (Part B) as needed or applicable. Analyses are descriptive in nature. Summaries of safety data are conducted using subjects receiving any Compound A (the Treated Population). Study data is summarized for disposition, demographic and baseline characteristics, exposure, efficacy, safety, PK, and PD. Categorical data is summarized by frequency distributions (number and percentages of subjects) and continuous data is summarized by descriptive statistics (mean, standard deviation, median, minimum, and maximum).

Treatment-emergent adverse events (TEAEs) are summarized by National Cancer Institute Common Terminology Criteria for Adverse Event grades. The frequency of TEAEs is tabulated by Medical Dictionary for Regulatory Activities system organ class and preferred term. Grade 3 or 4 TEAEs, TEAEs leading to discontinuation of Compound A, study drug related TEAEs, and SAEs are tabulated separately. Changes from baseline in selected laboratory analytes, vital signs, 12-lead ECGs, and ECHO/MUGA scans are summarized. All data is presented in by-subject listings.

The primary efficacy variable is DCR. Because the compound MoA may result in SDs and Disease control, however, PFS and OS may serve as additional efficacy assessments. Although OS and PFS are not usually assessed in FIH, Compound A administration may result in SDs and Responses (e.g., in NHL pts). Disease control is defined as tumor responses of CR. PR and SD (assessed by the Investigators). Point estimates and 95% confidence intervals of DCR are reported. The objective response rate (defined as the percentage of subjects whose best response is complete response or partial response), duration of response/stable disease, progression-free survival, and overall survival, is summarized using frequency tabulations for categorical variables or descriptive statistics for continuous variables. Efficacy analysis is repeated for the Treated Population and Efficacy Evaluable Population (subjects who received a baseline disease assessment evaluation, at least one cycle of study treatment, and one on-study disease assessment evaluation), with the result using the Treated Population considered primary.

During the Part A dose escalation, approximately 30 to 40 subjects are enrolled. During the Part B dose expansion, at least 14 efficacy evaluable subjects for each tumor cohort are accrued initially. If the response rate is 20% or more, there is more than a 95% chance that one or more responders would be observed in the first 14 subjects, to be updated by statistics based on change to DCR as a primary efficacy endpoint. Gehan, 1961. If no responder is observed out of 14 subjects, the enrollment for this tumor cohort is stopped for futility. Otherwise, the tumor cohort is expanded to up to ~20 subjects if a responder is observed.

More specifically, Compound A is assessed in an open-label, Phase 1a, dose escalation and expansion, FIH clinical study in subjects with advanced solid tumors and relapsed or refractory NHLs. The dose escalation part (Part A) of the study explores escalating oral doses of Compound A to estimate the MTD or RPTD of Compound A. A BLRM utilizing EWOC (Babb, 1998; Neuenschwander 2008) helps guide Compound A dose escalation decisions with the final decisions made by a scientific review committee (SRC). The expansion part (Part B) further evaluates the safety and efficacy of Compound A, administered at or below the MTD in selected expansion cohorts of up to ~20 evaluable subjects each, in order to further define the RP2D. One or more dosing regimens and/or disease subsets may be selected for cohort expansion. Parts A and B will consist of 3 periods: Screening, Treatment, and Follow-up periods (see FIG. 4).

As noted, the screening period starts 28 days prior to first dose of Compound A. The informed consent document (ICD) is signed and dated by the subject and the administering staff prior to the start of any other study procedures. All screening tests and procedures must be completed within the 28 days prior to the first dose of Compound A. During the treatment period, Compound A is initially administered orally once daily for three consecutive days followed by four consecutive days off drug every week (3/7 day dose schedule) in each 4-week cycle. Alternate dosing schedules (e.g., 2-days-on/5-days-off, each week) may be examined based on the review of available safety, PK, PD, and efficacy data by the SRC. In Part A, the window for evaluation of dose-limiting toxicity (DLT) is 28 days (4 weeks) during Cycle 1. In the follow-up period, all subjects are followed for 28 days (±2 days) after the last dose of Compound A for safety. Subjects who discontinue treatment for reasons other than disease progression (or relapse), start of a new anti-cancer therapy, or withdrawal of consent from the entire study will have disease assessments performed according to the specified tumor assessment schedule until progression and/or initiation of new systemic anticancer therapies. After the safety follow-up visit, all subjects are followed every subsequent 3 months (±2 weeks) for survival follow-up for up until 2 years or until death, lost to follow-up, or the end of trial, whichever occurs first.

Regarding Part A. Dose Escalation, a minimum of 3 subjects are enrolled at each dose level. The initial Compound A dose is 15 mg. The BLRM with EWOC incorporates available prior safety information and update the model parameters after each new cohort of subjects completes Cycle 1. The decision for the next dose is made by the SRC based on a calculation of risk assessment using the BLRM, and available safety (i.e., DLT and non-DLT safety data), PK, PD, and efficacy information. In addition, relevant non-clinical data (e.g., GLP toxicity studies, in vivo pharmacology from xenograft models, etc.) may be utilized in the assessment. Details of the statistical methodology are provided in Appendix H.

At all decision time points, the BLRM permits alterations in the dose increments based on the observed DLTs; however, the dose for the next cohort does not exceed a 100% increase from the prior dose. The MTD is the highest dose that is unlikely (<5% posterior probability) to cause DLT in ≥33% of the treated subjects in the first cycle of Compound A. The SRC makes the final decision regarding the Compound A dose for each cohort.

During dose escalation, a Compound A dose can be declared the MTD and/or RP2D after meeting the following conditions: at least six evaluable subjects have been treated at the dose; the posterior probability of targeted toxicity at the dose exceeds 60% and is the highest among the escalation doses or a minimum of 21 subjects have been treated on the study; the dose is recommended according to the BLRM and the SRC approves it.

The SRC includes Investigators (and/or designated representatives), the Sponsor's study physician, safety physician, study statistician, and the study manager. Ad hoc attendees may include the study pharmacokineticist and additional study clinical scientists. Other internal and external experts may be consulted by the SRC, as necessary.

The decision to evaluate additional subjects within a dose cohort, a higher dose cohort, intermediate dose cohorts, smaller dose increments, alternate dosing schedules (e.g., 2 days on/5 days off each week), or declare an MTD will also be determined by the SRC, based on the BLRM assessment and their review of available safety (i.e., DLT and non-DLT data), PK, PD, and efficacy information.

After the first dose is administered in any cohort during dose escalation, subjects in each cohort are observed for 28 days (Cycle 1, DLT window) before the next dose cohort can begin. No more than one subject per day is enrolled in a given dose escalation cohort. Those subjects non-evaluable for DLT are replaced. A subject evaluable for DLT is defined as one that has received at least 10 of 12 doses (or ≥80% of the total planned dose intensity) of Compound A during Cycle 1 without experiencing a DLT; or Experienced a DLT after receiving at least one dose of Compound A.

Intra-subject dose escalation is not allowed during the DLT assessment period. In Cycles ≥3, however, subjects without evidence of disease progression who are tolerating their assigned dose of Compound A may (at the Investigator's discretion and in consultation with the study's medical monitor) escalate to the highest dose level shown to be adequately tolerated by at least one cohort of subjects in this study (i.e., overdose risk is less than 25% based on the BLRM assessment).

Regarding Part B. Cohort Expansion, following completion of dose escalation (Part A), selected tumor cohorts are enrolled into an expansion phase (Part B) with up to approximately twenty evaluable subjects each. Expansion may occur at the MTD and schedule established in the dose escalation phase, or at an alternative tolerable dose and schedule, based on review of available safety, PK, PD, and efficacy data from Part A. The SRC selects the doses and schedules of interest for cohort expansion. One or more dosing regimens may be selected for cohort expansion. The SRC continues to review safety data regularly throughout the study and make recommendations about study continuation and dose modification, as appropriate.

A schedule of assessments is shown in Table 4 and assessments are described below. The safety variables for this study include adverse events, safety clinical laboratory variables, 12-lead electrocardiograms, Eastern Cooperative Oncology Group Performance Status, left ventricular ejection fraction assessments, physical examinations, vital signs, exposure to study treatment, assessment of concomitant medications, and pregnancy testing for females of child bearing potential. Subjects are evaluated for efficacy after every 2 cycles through Cycle 6, and thereafter every 3 cycles. All subjects who discontinue treatment for reasons other than disease progression, start of a new anticancer therapy, or withdrawal of consent from the entire study will be followed until progression and/or initiation of new systemic anticancer therapies.

Blood is collected at specified time-points for determining the PK profiles of Compound A and for exploratory PD assessments. Paired tumor biopsies for analysis of biomarkers of treatment activity are optional in the dose escalation phase but mandatory during the dose expansion phase.

The study is conducted in compliance with the International Council on Harmonisation (ICH) of Technical Requirements for Registration of Pharmaceuticals for Human Use/Good Clinical Practice (GCP) and applicable regulatory requirements.

Enrollment may take ~30 mo to complete (12-18 mo dose escalation and 9-12 mo expansion). Completion of active treatment and post-treatment follow-up is expected to take an additional 4-28 mo. The entire study is expected to last ~4 yr.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

This Example proposes a multicenter, open-label study in which approximately 30 to 40 subjects are enrolled during Part A (dose escalation). During the Part B (dose expansion), up to 20 evaluable subjects are enrolled in each of the selected dose expansion cohorts. Enrollment occurs at approximately 4-6 sites in Europe for Part A. Enrollment in Part B may include additional sites in the United States and Europe.

Regarding inclusion criteria, subjects must satisfy the criteria below to be enrolled in dose escalation (Part A) of this study:
1. Men and women ≥18 years of age, the time of signing the informed consent document (ICD);
2. Subject must understand and voluntarily sign an ICD prior to any study-related assessments/procedures being conducted;
3. Subject is willing and able to adhere to the study visit schedule and other protocol requirements;
4. Subjects with histological or cytological confirmation of advanced unresectable solid tumors or iNHL (DLBCL and iNHL) including those who have progressed on (or not been able to tolerate due to medical comorbidities or unacceptable toxicity) standard anticancer therapy or for whom no other approved conventional therapy exists;
5. At least one site of measurable disease (>1.5 cm in the long axis or >1.0 cm in both the long and short axis) must be present in subjects with solid tumors and iNHL;
6. Subject consents to mandatory tumor biopsies (Screening and Cycle 1) in Part B. Tumor biopsies are optional in Part A;
7. ECOG Performance Status of 0 to 1;
8. Subjects must have the following laboratory values at screening: (a) Absolute neutrophil count (ANC)≥1.5× $10^9$/L without growth factor support for 7 days (14 days if subject received pegfilgrastim); (b) Hemoglobin (Hgb)≥9 g/dL (≥8 g/dL for NHL subjects); (c) Platelet count (plt)≥75×$10^9$/L (≥50×$10^9$/L without transfusion for 7 days for NHL subjects); (d) Serum potassium concentration within normal range, or correctable with supplements; (e) Serum AST/SGOT and ALT/SGPT ≤3.0×Upper Limit of Normal (ULN) or ≤5.0×ULN if liver metastases are present; (f) Serum total bilirubin ≤1.5×ULN or ≤2×ULN if liver metastases are present; (g) Serum creatinine ≤1.5×ULN, or 24-hour measured creatinine clearance ≥50 mL/min using the Cockcroft-Gault equation; (h) Subjects with documented liver metastases must have serum albumin ≥3 g/dL; and (i) INR<1.5×ULN and PTT<1.5×ULN;
9. Females of childbearing potential (FCBP) must: (A) Either commit to true abstinence from heterosexual contact (which must be reviewed on a monthly basis and source documented) or agree to use, and be able to comply with, at least two effective contraceptive methods (oral, injectable, or implantable hormonal contraceptive; tubal ligation; intra-uterine device; barrier contraceptive with spermicide; or vasectomized partner), one of which must be barrier, from signing the ICD, throughout the study, and for up to 28 days or up to 3 months following the last dose of Compound A; and (B) Have two negative pregnancy tests as verified by the Investigator prior to starting Compound A: a negative serum pregnancy test (sensitivity of at least 25 mIU/mL) at Screening; a negative serum or urine pregnancy test (Investigator's discretion) within 72 hr prior to Cycle 1 Day −1 of study treatment; (C) Avoid conceiving for 3 mo after the last dose of Compound A; (D) Agree to ongoing pregnancy testing during the course of the study, and after the end of study treatment. This applies even if the subject practices true abstinence from heterosexual contact; and 10. Males must practice true abstinence (which must be reviewed on a monthly basis) or agree to use a condom (a latex condom is recommended) during sexual contact with a pregnant female or a FCBP and will avoid conceiving from signing the ICD, while participating in the study, during dose interruptions, and for at least 3 month following Compound A discontinuation, even if he has undergone a successful vasectomy.

A female of childbearing potential is a sexually mature woman who (1) has not undergone a hysterectomy (the surgical removal of the uterus) or bilateral oophorectomy (the surgical removal of both ovaries) or (2) has not been naturally postmenopausal for at least 24 consecutive mo (e.g., has had menses at any time during the preceding 24 consecutive mo). True abstinence is acceptable when this is in line with the preferred and usual lifestyle of the subject. Periodic abstinence (e.g., calendar, ovulation, symptothermal, post-ovulation methods) and withdrawal are not acceptable methods of contraception.

The presence of any of the following excludes a subject from enrollment:

(1) Subject has received anti-cancer therapy (either approved or investigational) within ≤4 weeks or 5 half-lives, whichever is shorter, prior to signing the ICD;
(2) Toxicities resulting from prior systemic cancer therapies must have resolved to ≤NCI CTCAE Grade 1 prior to starting Compound A treatment. Peripheral neuropathy ≥NCI CTCAE Grade 2;
(3) Subject has received autologous hematologic stem cell transplant (HSCT) ≤3 mo or allogenic HSCT ≤6 mo prior to starting Compound A treatment: the 6-mo exclusionary period for recovery from HSCT-associated toxicity, applies regardless of whether an autologous or allogeneic transplant was performed;
(4) Subject has undergone major surgery ≤4 wk or minor surgery ≤2 wk prior to signing the ICD or who have not recovered from surgery;
(5) Subject has completed any radiation treatment <4 wk prior to signing the ICD;
(6) Subject has persistent diarrhea due to a malabsorptive syndrome (such as celiac sprue or inflammatory bowel disease) ≥NCI CTCAE Grade 2, despite medical management, or any other significant GI disorder that could affect the absorption of Compound A;
(7) Subjects with symptomatic or uncontrolled ulcers (gastric or duodenal), particularly those with a history of and/or risk of perforation and GI tract hemorrhages;
(8) Symptomatic or unstable central nervous system metastases: Subjects recently treated with whole brain radiation or stereotactic radiosurgery for CNS metastases must have completed therapy at least 4 wk prior to Cycle 1, Day 1 and have a follow-up brain CT or MRI demonstrating either stable or improving metastases 4 or more wk after completion of radiotherapy (the latter to be obtained as part of the Screening Assessments);
(9) High grade, rapidly proliferative solid tumors (e.g., small cell lung cancer, germ cell tumors, neuroblastoma) with extensive tumor burden (>10 cm in sum of diameters of measurable lesions) and LDH>ULN;
(10) Known symptomatic acute or chronic pancreatitis;
(11) Impaired cardiac function or clinically significant cardiac diseases, including any of the following: LVEF <45% as determined by multiple gated acquisition scan (MUGA) or echocardiogram (ECHO); Complete left bundle branch or bifascicular block; Congenital long QT syndrome; Persistent or clinically meaningful ventricular arrhythmias or atrial fibrillation; QTcF ≥470 msec on Screening ECG (mean of triplicate recordings); Unstable angina pectoris or myocardial infarction ≤6 mo prior to starting Compound A; Other clinically significant heart disease such as congestive heart failure requiring treatment or uncontrolled hypertension (blood pressure ≥160/95 mm Hg);
(12) Pregnant or nursing females;
(13) Known HIV infection;
(14) Known chronic active hepatitis B or C virus (HBV, HCV) infection: Subjects who are seropositive due to HBV vaccination are eligible; Subjects who have no active viral infection and are under adequate prophylactics against HBV reactivation are eligible; Allowance for HCC with respect to HCV may be considered;
(15) Ongoing treatment with chronic, therapeutic dosing of anti-coagulants (e.g., warfarin, low molecular weight heparin. Factor Xa inhibitors). Low dose low molecular weight heparin for catheter maintenance are permitted;
(16) History of concurrent second cancers requiring active, ongoing systemic treatment;
(17) Subjects with a history of clinically significant cognitive disorder(s) or active cognitive disorder(s);
(18) Subject has any significant medical condition (e.g., active or uncontrolled infection or renal disease), laboratory abnormality, or psychiatric illness that would prevent the subject from participating (or compromise compliance) in the study or would place the subject at unacceptable risk if he/she were to participate in the study;
(19) Subjects with a history of clinically significant cognitive disorder(s) or active cognitive disorder(s); and
(20) Subject has any condition that confounds the ability to interpret data from the study.

Regarding procedures, questions regarding the protocol should be directed to the Medical Monitor or designee. The procedures conducted for each subject enrolled in the study are outlined in Table 4:

TABLE 4

| | Screening | Treatment Period | | | | | | | |
| --- | --- | --- | --- | --- | --- | --- | --- | --- | --- |
| | | Cycle 1 | | | | | | Cycles 2-4 | |
| | D −28 | WK 1 | | | WK 2 | WK 3 | WK 4 | WK 1 | WK 2 |
| Event[a] | to −1 | D 1 | D 2 | D 3 | D 8 | D 15 | D 22 | D 1 | D 8 |
| Study Entry | | | | | | | | | |
| Informed consent and contraceptive counseling | X | | | | | | | | |
| Informed consent for optional exploratory analyses/PK sampling | X | | | | | | | | |
| Inclusion/exclusion criteria | X | | | | | | | | |
| Medical/oncologic history and therapies | X | | | | | | | | |
| Demographics | X | | | | | | | | |
| IRT registration | X | X | | | | | | | |
| Prior/concomitant medications, procedures | X | X | X | X | X | X | X | X | X |
| Study Drug | | | | | | | | | |
| Administer oral Compound A per assigned dosing schedule[d] | | X | X | X | X | X | X | X | X |
| Provide/review diary card | | X | X | X | X | X | X | X | X |
| Safety Assessment | | | | | | | | | |
| Adverse Event Evaluation | X | X | X | X | X | X | X | X | X |
| Height | X | | | | | | | | |
| Weight | X | X | | | X | X | X | X | X |
| Vital Signs | X | X | | | X | X | X | X | X |
| Physical Examination | X | X | | | | | | X | |
| ECOG PS | X | X | | | | | | X | |
| 12-lead ECG (single or triplicate)[e] | X ≥72 hours prior to D 1 | X | | | | X D 17 only | | X | |
| LVEF (ECHO/MUGA) | X | | | | | | | X C2 only ±7 d | |
| Pregnancy Testing (FCBP only) | X | X | | | | | | X | |
| Hematology laboratory | X D −14 to −1 | X | | | X | X | X | X | X C2 only |
| Chemistry laboratory with LDH, uric acid tests | X D −14 to −1 | X | | | X | X | X | X | X C2 only |
| PT, INR, PTT | X D −14 to −1 | X | | | X | X | X | X | X C2 only |
| Amylase, lipase, T-cell subsets (CD4+ and CD8+), TSH | | X | | | | | | | X C2 only |
| Urinalysis | X D −14 to −1 | X | | | | | | X | |

TABLE 4-continued

Events

PK and PD Assessments

| | | | | |
|---|---|---|---|---|
| Blood, PK | | X | X | X D 17-18 |
| CSF, PKf | | | | X D 17 |
| Blood (whole), parmacogenomics | | X | | |
| Blood (whole), PAX gene for RNA | | X | X | |
| Tumor Biopsy[g] | X D −7 to −1 | | | X D 16 or D 17 |
| Archival tumor tissue (FFPE) | | X | | |

Efficacy

| | |
|---|---|
| Solid tumor/NHL assessments: CT/MRI imaging[b] | X |
| NHL-specific: bone marrow evaluation if known or suspected bone marrow involvement | X |
| NHL-specific: FDG PET or PET/CT scan (not required if tumor is FDG-negative) | X |

Additional Follow-up

Follow-up anticancer therapies
SAE follow-up
Survival follow-up

| | Treatment Period | | | | Follow-up Period | |
|---|---|---|---|---|---|---|
| | Cycles 2-4 | | Cycles 5+ | | Safety[b] | Long Term |
| Event[a] | WK 3 D 15 | WK 4 D 22 | WK 1 D 1 | WK 3 D 15 | EOT ≤28 D | 28 D ± 2 D | q3 mo (±2 wk) |

Study Entry

| | | | | | | |
|---|---|---|---|---|---|---|
| Informed consent and contraceptive counseling | | | | | | |
| Informed consent for optional exploratory analyses/PK sampling | | | | | | |
| Inclusion/exclusion criteria | | | | | | |
| Medical/oncologic history and therapies | | | | | | |
| Demographics | | | | | | |
| IRT registration | | | | | X | |
| Prior/concomitant medications, procedures | X | X | X | X | X | X |

TABLE 4-continued

| Events | | | | | | |
|---|---|---|---|---|---|---|
| Study Drug | | | | | | |
| Administer oral Compound A per assigned dosing schedule[d] | X | X | | | | |
| Provide/review diary card | X | X | X | X | X | |
| Safety Assessment | | | | | | |
| Adverse Event Evaluation | X | X | X | X | X | X |
| Heigh | | | | | | |
| Weight | X | X | X | X | X | |
| Vital Signs | X | X | X | X | | |
| Physical Examination | | | X | | | |
| ECOG PS | | | X | | | |
| 12-lead ECG (single or triplicate)[e] | | | X | | X | |
| LVEF (ECHO/MUGA) | | | X C5 only ±7 d | | X ±7 d | |
| Pregnancy Testing (FCBP only) | | | X | | X | |
| Hematology laboratory | X | X C2 only | X | | X | |
| Chemistry laboratory with LDH, uric acid tests | X | X C2 only | X | | X | |
| PT, INR, PTT | X | X C2 only | X | | X | |
| Amylase, lipase, T-cell subsets (CD4+ and CD8+), TSH | | | X q3 cycle C5, C8, C11 | | X | |
| Urinalysis | | | X | | X | |
| PK and PD Assessments | | | | | | |
| Blood, PK | | | | | | |
| CSF, PKf | | | | | | |
| Blood (whole), parmacogenomics | | | | | | |
| Blood (whole), PAX gene for RNA | | | | | | |
| Tumor Biopsy[g] | | | | | | |
| Archival tumor tissue (FFPE) | | | | | | |
| Efficacy | | | | | | |
| Solid tumor/NHL assessments: CT/MRI imaging[b] | | X D28 ±7 d; C2, C4 | X D28 ±7 d in C6, then q3 cycles: end of C9, C12, etc | X | | |
| NHL-specific: bone marrow evaluation if known or suspected bone marrow involvement | | X D 28 ± 7 d in C2 | X only then confirming CR | X | | |
| NHL-specific: FDG PET or PET/CT scan (not required if tumor is FDG-negative) | | | X when confirming CR | | | |

TABLE 4-continued

| Events | | |
|---|---|---|
| Additional Follow-up | | |
| Follow-up anticancer therapies | X | X |
| SAE follow-up | X | |
| Survival follow-up | | X |

Table 4. Key

β-hCG = beta human chorionic gonadotropin; BMMC = bone marrow mononuclear cells; C = cycle; CK = creatine kinase; CSF = cerebrospinal fluid; CT = computed tomography; D = day(s); ECHO = echocardiogram; ECOG Eastern Cooperative Oncology Group; FCBP = females of child bearing potential; FFPE = formalin-fixed, paraffin embedded; fT4 = free T4; INR = international normalized ratio; IRT = integrated response technology; LVEF = left ventricular ejection fraction; mo = months; MUGA = multi-gated acquisition scan; PK = pharmacokinetic; PT = prothrombin time; PTH = parathyroid hormone; PTT = partial thromboplastin time; q = every; TSH = thyroid-stimulating hormone; WK(s) = week.
$^a$All study visits/procedures have a ±2 day window and all laboratory blood samples are drawn predose unless otherwise specified.
$^b$This safety follow-up assessment may be by telephone.
$^c$Survival follow-up for up to 2 yr or until death, lost to follow-up, or End of Trial, whichever occurs first. May be conducted by record review (including public records) or telephone contact with the subject, family, or treating physician.
$^d$Not all Compound A dosing days are shown. Dose schedule is initially 3/7 day schedule. Alternate dosing schedules may be implemented based on SRC decisions.
$^e$Screening triplicate ECG performed ≥72 hours prior to dosing on Day 1 so that the central read results are available for review.
$^f$Optional for subjects with a primary or metastatic CNS lesion and a shunt or reservoir in place. Recommended time for CSF collections is 4 hr (±1 hr) after dosing on Day 17 (or on day of last dose of Compound A in Cycle 1). Other times for CSF collection allowed if CSF collection is on a PK day and is consistent with one of the scheduled blood PK collection times: 1-8 hr post-dose.
$^g$Paired tumor biopsies mandatory for Part B and highly recommended for Part A. Screening biopsy obtained after all inclusion/exclusion criteria are fulfilled. The Cycle 1 biopsy obtained on Day 16 or 17 if two consecutive Compound A doses have been administered.
$^h$All subjects who discontinue treatment for reasons other than disease progression, start of new anticancer therapy, or withdrawal of consent from the entire study are followed according to the specified tumor assessment schedule until progression or initiation of new systemic anticancer therapies.
$^i$May be omitted if results are normal on subject's most recent historical bone marrow biopsy. Additionally, analysis omitted if a prior analysis performed within 90 days before Cycle 1 Day 1.

All study visits have a ±2 day window unless otherwise specified below or in the Table of Events (see Table 4). All laboratory blood samples are drawn pre-dose unless otherwise specified (e.g., PK samples). The study procedures are recorded in the source document and the electronic case report forms (eCRF). In the event subjects fail Screening, minimal information is documented on the eCRFs, per database instructions.

Safety laboratory analyses may be performed locally. Screening laboratory values must demonstrate subject eligibility, but may be repeated within the screening window, if necessary. The ICD is administered at the Screening visit to all subjects by qualified study staff. It must be signed and dated by the subject and the administering staff prior to the start of any other study procedures and its completion documented in source documents and in the eCRF. All screening tests and procedures must be completed within 28 days prior to the first dose of Compound A according to the schedule shown in Table 4.

The following are performed at Screening, after informed consent has been obtained: Inclusion and exclusion criteria are assessed at Screening and recorded in the source documents and the eCRF; Contraceptive counseling; Medical, oncologic, and surgical history, and demographic data (including each subject's date of birth, sex, race, and ethnicity) are collected during Screening as consistent with local regulations. Oncologic history includes a detailed history of the primary diagnosis and date, therapies, and responses: Information on prior and concomitant medications and procedures is collected; Registration in the integrated response technology system (IRT); Adverse event monitoring; Height and weight measured; Vital signs assessed; Physical examination (source documented only) and ECOG performance status; A 12 lead ECG in triplicate are performed ≥72 hours prior to the first dose of Compound A with results received from the central read prior to dosing to fulfil eligibility criteria; Left Ventricular Ejection Fraction (LVEF) assessment; Pregnancy testing for all females of childbearing potential. Appropriate methods of contraception and potential risks of fetal exposure will be discussed with subjects during Screening. Double contraceptive methods (one of which must be a barrier method) for females of childbearing potential (e.g., oral, injectable, or implantable hormonal contraceptive; intra-uterine device; barrier contraceptive with spermicide; or vasectomized partner) and a single contraceptive method for males (a condom) must be used from the time the ICD is signed, throughout the study by subjects, and for 28 days after the last dose of the Compound A. This is documented in source documents; Clinical laboratory tests are to be completed within the timeframe (see Table 2); Efficacy/tumor assessments.

Qualified healthcare professionals are trained in the requirements specific to contraceptive counseling of subjects. Once trained these healthcare staff will counsel subjects prior to the administration of Compound A to ensure that the subject has complied with all requirements including use of birth control and that the subject understands the risks associated with Compound A.

During the treatment period, all concomitant medications and procedures taken or conducted beginning when the subject signs the ICD, throughout the study, and until 28 days after the last dose of Compound A are recorded in the source documents and eCRF.

Adverse events and serious adverse events (SAEs) are recorded from the time a subject signs the ICD until 28 days after the last dose of Compound A. Subjects experiencing AEs are monitored with relevant clinical assessments and laboratory tests, as determined by the Investigator. Every attempt is made to document resolution dates for ongoing AEs. The AEs are recorded on the AE page of the eCRF and in the subject's source documents. Photographs of skin rashes are obtained whenever possible, anonymized, and stored appropriately for future retrieval.

The subject's weight is recorded in the source document and eCRF at the visits listed in Table 4. Vital signs include body temperature, blood pressure, pulse rate, and respiration rate and will be recorded at Screening and during the study at various time points for safety monitoring as described in Table 4. Recorded measurements are captured in the source document and eCRF. Complete physical examination and Eastern Cooperative Oncology Group Performance Status (ECOG PS; refer to Appendix D) will be performed at the visits listed in Table 4. Results for both are recorded in the source document. Results for the ECOG PS are also be collected on the eCRF. Physical examination findings are classified as either normal or abnormal. If abnormal, a description of the abnormality and clinical importance is provided in the source documents. Clinically significant changes from baseline are recorded in the AE section of the eCRF. Triplicate standard 12-lead electrocardiograms (ECGs) will be recorded at the visits listed in Table 4. The 12-lead ECGs (12-lead at 25 mm/sec reporting rhythm, ventricular rate, PR interval. QRS complex, QT interval, and QTc interval) is performed after the subject has been in the supine position for at least 5 minutes. Triplicate ECGs (three recordings within 2±1 minute intervals) are performed at: (a) Screening (b) Cycle 1 (c) Day 1: pre-dose (within 30 min prior to dosing) and 2 hr (±10 min) post-dose (d) Day 17: pre-dose (within 30 min prior to dosing) and 2 hr (±10 min) post-dose (e) Cycles 2 and higher: Day 1: pre-dose (within 30 min prior to dosing)

A single ECG will be performed at the EOT visit. For alternate dosing schedules, the Cycle 1 Day 17 ECGs will be performed on the last day of Compound A dosing in Cycle 1. Investigators make immediate clinical decisions based on their interpretation of the ECG results and provide their overall assessment of the ECG in the eCRF. Clinically significant changes from baseline will be recorded in the AE section of the eCRF. The ECG outputs are also uploaded to the central ECG laboratory for definitive analysis and interpretation. Left ventricular ejection fraction (LVEF). (multiple gated acquisition scan [MUGA], or echocardiogram [ECHO]) are conducted at Screening in all subjects. Follow-up assessments are required as indicated in Table 4. Follow-up assessments should use the same procedure used at the screening assessment. A clinically significant reduction is defined as either a ≥20% absolute reduction in LVEF or drop to below 45%.

A female of childbearing potential (FCBP) is defined as a sexually mature woman who has: (a) Not undergone a hysterectomy or bilateral oophorectomy, and (b) Not been naturally postmenopausal (amenorrhea following cancer therapy does not rule out childbearing potential) for at least 24 consecutive mo (e.g., has had menses at any time in the preceding 24 consecutive mo).

The Investigator classifies a female subject as a FCBP according to this definition. Pregnancy testing is not required for non-FCBP subjects but justification must be recorded in the eCRF and the source document. Pregnancy testing is conducted by the local laboratory.

Results for pregnancy tests are recorded in the source document and eCRF. For a FCBP, pregnancy testing is conducted at the visits (see also Table 4): (a) A serum pregnancy test with sensitivity of at least 25 mIU/mL is obtained at Screening and serum or urine pregnancy test (based on Investigator's discretion) within 72 hr prior to Cycle 1 Day −1 of study treatment. The subject may not receive Compound A until the Investigator has verified the 2 screening pregnancy tests are negative. (b) A serum or urine pregnancy test (based on Investigator's discretion and minimum test sensitivity [25 mIU/mL]) are done within 72 hr prior to Day 1 of every cycle and at the end of treatment (EOT) visit. The subject may not receive Compound A until the Investigator has verified the pregnancy test is negative. (c) A FCBP or a male subject whose partner is an FCBP must avoid activities that could lead to conception for 3 mo after the last dose of Compound A.

The following laboratory assessments are performed at the Screening visit and during the study at the time points as described in Table 4. All samples are drawn pre-dose unless otherwise specified. Laboratory assessments are recorded in the source document and eCRF and are the following: (a) Hematology: complete blood counts (CBC) including hemoglobin, hematocrit. WBC count with absolute differential (including blast count) and platelet count. (b) Serum chemistry: albumin, total protein, bicarbonate or $CO_2$, magnesium, phosphorus, calcium, creatinine, urea/BUN, glucose (fasting ≥4 hr), potassium, sodium, chloride, total bilirubin (fractionate if outside normal range), alkaline phosphatase. AST or serum glutamic oxaloacetic transaminase (SGOT), ALT or serum glutamate pyruvic transaminase (SGPT), LDH, and uric acid; baseline hemoglobin A1c in case hyperglycemia is significant based on other BETi's in the clinic. (c) Special chemistry: amylase, lipase. T-cell subsets (CD4+ and CD8+), thyroid-stimulating hormone (TSH; if abnormal reflex to free T4). (d) Coagulation: PT, INR, and PTT (e) Urinalysis: dipstick: microscopy in the event of a positive (1+ or greater) blood or protein; 24-hr collection for creatinine clearance and protein quantification in the event of 2+ or greater protein (e) Creatinine clearance determination required at Screening to fulfill inclusion criteria.

An EOT evaluation (refer to Table 4 for procedures) is performed for subjects who are withdrawn from treatment for any reason as soon as possible (≤28 days) after the decision to permanently discontinue treatment has been made. All subjects are followed for 28 days after the last dose of Compound A for AE reporting and concomitant medication information. The 28-day (±2 days) safety follow-up contact may be by telephone. In addition, any SAEs made known to the Investigator at any time thereafter that are suspected of being related to Compound A are reported. After the Safety Follow-up visit, all subjects are followed every subsequent 3 mo (±2 wk) for survival follow-up for up to 2 yr or until death, lost to follow-up, or the End of Trial, whichever occurs first. New disease therapies should be collected at the same time schedule. Survival follow-up may be conducted by record review (including public records) and/or telephone contact with the subject, family, or the subject's treating physician.

Regarding efficacy assessment, tumor assessments are performed at screening and include CTs of the chest, abdomen and pelvis, and a brain scan (CT or MRI) for subjects with known or suspected cerebral involvement. After screening, radiologic tumor assessments are performed at the end (Day 28±7 days) of Cycles 2, 4, and 6, and then every three cycles thereafter, using the same CT/MRI scanning modalities used at Screening. An EOT scan does not need to be obtained if the prior scan was within 28 days. Additionally, for NHL subjects, a Screening FDG PET or FDG PET/CT scan is performed unless the tumors are known to be FDG-avid negative. A subsequent scan will be obtained to confirm a CR. For NHL subjects with known or suspected bone marrow involvement, a bone marrow evaluation with flow immunophenotyping will be performed at Screening, after two cycles (end of Cycle 2), and to confirm a complete response (CR).

All subjects who discontinue treatment for reasons other than disease progression, start of a new anticancer therapy, or withdrawal of consent from the entire study are followed according to the specified tumor assessment schedule until progression or initiation of new systemic anticancer therapies. Tumor response at each post-screening assessment is determined by Investigator, based on Response Evaluation Criteria in Solid Tumors (RECIST) v 1.1 as described in Appendix B for solid tumors and the Revised Response Criteria for Malignant Lymphoma as described in Appendix C for NHL.

The PK assessments are described below. For evaluation of PK of Compound A in plasma, blood samples are collected from all subjects at the time points listed in Table 5. The actual time of each sample collection is recorded in the source documents and on the electronic case report forms (eCRFs). A baseline PK sample may include a collection in on Day 1 in Part B.

TABLE 5

Blood Pharmacokinetic Sampling Schedule for Cycle 1

| Time in Hours Relative to Compound A Dose | Collection Window | Part A, Cycle 1 Days 1 and 17[a] | Part B, Cycle 1 Day 17[a] |
|---|---|---|---|
| 0 | Within 30 min prior | X | X |
| 0.5 | ±5 min | X | X |
| 1 | ±5 min | X | X |
| 1.5 | ±5 min | X | X |
| 2 | ±5 min | X | X |
| 3 | ±10 min | X | X |
| 4 | ±10 min | X | X |
| 6 | ±10 min | X | X |
| 8 | ±10 min | X | X |
| 24 | ±1 hour | X (pre Day 2 dosing) | X (Day 18) |

[a]For alternate dosing schedules, Day 17 blood collections for PK samples are performed on the last day of dosing in Cycle 1 at the same time points shown.

An exploratory analysis of Compound A concentrations in CSF may be performed for subjects who have a primary or metastatic CNS lesion with a shunt or reservoir in place and who provide consent for the optional collection. The recommended time for CSF collections may include a sample prior to exposure, then 4 hr (±1 hr) after dosing on Day 17 (or the last day of Compound A dosing in Cycle 1 if alternate dosing schedules are implemented). Other times for CSF collection are allowed as long as the time for CSF collections is on a PK day and is consistent with one of the scheduled blood PK collection times between 1-8 hr post-dose (see Table 4). The Sponsor may conduct additional analyses on the PK samples in order to follow up the safety of the study treatment or to better understand the progression of the disease or the disease's response to the study treatment. Sample collection, handling, and processing follow the standard instructions of good laboratory practices.

Regarding biomarkers, pharmacodynamics, and pharmacogenomics, archival tumor, as formalin-fixed, paraffin-embedded (FFPE) blocks or mounted sections (15 slides recommended), are retrieved after eligible subjects are enrolled in the IRT system unless single case exemption is granted by the Sponsor. For pharmacogenomic blood samples, a whole blood sample is collected at after eligible subjects are enrolled in the IRT system for assessment of potential pharmacogenomic markers of Compound A safety, activity or exposure. See the Laboratory Manual and Appendix G for sample collection, handling, and processing instruction.

The schedules for pharmacodynamic and predictive biomarkers are provided: (a) Whole blood for PD biomarker studies: Cycle 1 Day 1: pre-dose (≤3 hr), and 2, 4, 8, (each ±15 min) and 24 hr (±1 hr) after the Compound A dose (b) Tumor tissue for PD biomarker studies: Screening: Day −7 to −1 (after all inclusion and exclusion criteria are fulfilled); Cycle 1 Day 16 or 17: 2 hr (±1 hr) after the Compound A dose; and Optional, any other time until EOT visit.

The Sponsor may conduct additional analyses on the PD samples in order to follow up the safety of the study treatment or to better understand the progression of the disease or the disease's response to the study treatment.

Tumor biopsies are mandatory in Part B and optional (but encouraged) in Part A. The biopsy is collected either tumor excision (preferred) or by core needle (four passages recommended) at Screening and in Cycle 1 on Day 16 or 17. Fine needle aspiration is not sufficient as a source of tumor biopsy material. Samples may be processed as fresh frozen paraffin-embedded (FFPE). Optimally, the tumor tissue samples are obtained from the same tumor site. If Compound A has been interrupted prior to completing the Cycle 1 Day 16 or 17 dose, it is recommended that the tumor biopsy be deferred until after at least two consecutive doses have been administered. Additionally, an optional tumor biopsy may be obtained in both Part A and Part B, during later treatment cycles or following treatment discontinuation (any time during the 28-day follow-up period) to elucidate effects of long-term treatment or resistance mechanisms, respectively. See the Laboratory Manual and Appendix G for sample collection, handling, and processing instruction.

The Investigational Product(s) is Compound A, which has a molecular weight of 464 g/mole. Compound A clinical drug product is provided as a formulation. Compound A clinical drug product should be stored as indicated on the package label.

Compound A is administered once daily in the morning on an empty stomach (i.e., ≥1 hr before breakfast) with at least 240 mL of water after an overnight fast lasting ≥6 hr in both Parts A and B. Subjects should abstain from food or other medication intake for ≥1 hr after each dose. Subjects will administer Compound A starting on Day 1 for 3 consecutive days followed by four consecutive days off drug every week (3/7-day dose schedule) in each 4-week cycle. Alternate dosing schedules may be implemented based on the review of clinical safety and laboratory data by the SRC.

On study days that require PK assessments. Compound A is administered in the clinic after any pre-dose assessments are completed. On all other study days, subjects will self-administer their assigned doses at home and record dosing times on the study diary card.

Study treatment may be discontinued if there is evidence of clinically significant disease progression, unacceptable toxicity or subject/physician decision to withdraw. Subjects may continue to receive study drug beyond disease progression at the discretion of the Investigator in consultation with the Sponsor Medical Monitor.

For the purposes of dose escalation decisions, at least three subjects are enrolled in successive cohorts. The first cohort is treated with the starting dose of 15 mg. Subjects must complete a minimum of one cycle of treatment with the minimum safety evaluation and drug exposure or have had a DLT within the first cycle of treatment to be considered evaluable for dose escalation decisions. Dose escalation decisions will occur when the cohort of subjects has met these criteria. Dose escalation decisions will be made by the SRC. Decisions will be based on a synthesis of all relevant data available from all dose levels evaluated in the ongoing study including safety information, DLTs, all treatment related CTCAE grade ≥2 toxicity data during Cycle 1, and PK, data from evaluable subjects. PK data from subjects are made available on an on-going basis throughout the study and dosing will be adapted accordingly. The recommended dose for the next cohort of subjects will be guided by the BLRM with EWOC principle.

The adaptive Bayesian methodology provides an estimate of the dose levels of Compound A that do not exceed the MTD and incorporates all DLT information at all dose levels for this estimation. In general, the next recommended dose will have the highest chance that the DLT rate will fall in the target interval (16%-33%) and will always satisfy the EWOC principle. In all cases, the recommended dose for the next cohort will not exceed a 100% increase from the previous dose. Smaller increases in dose may be recommended by the SRC upon consideration of all of the available clinical data.

The procedure for subject accrual in each dose cohort and provisions for dose escalation/de-escalation decisions for the study is as follows: (1) In order to limit the number of subjects being treated at a sub-therapeutic dose, this study will begin by evaluating Compound A in cohorts of at least 3 evaluable subject at each dose level. Initially, the dosing increments between cohorts will be 100%. When 2 subjects (who may be in different cohorts) have experienced a treatment-related toxicity of NCI CTCAE Grade 2 or a single subject experiences a DLT or grade ≥3 toxicity, the cohort size may be increased to at least 6 evaluable subjects for the current and subsequent cohorts. The increase in Compound A dose will be ≤50% for each subsequent dose escalation cohort; (2) Following completion of Cycle 1 for all evaluable subjects in a cohort, the two-parameter BLRM with EWOC principle will be used to make recommendations to the SRC for the next dose level with the following exceptions: If the first 2 subjects in a cohort experience DLTs, no additional subjects will be enrolled into that cohort until the Bayesian model has been updated with this new information. Likewise, the model will be re-evaluated if 2 subjects in a cohort experience DLTs before the enrollment of any additional subject; If a decision has been made to escalate to a higher dose level, but one or more additional subjects treated at preceding dose levels (see number 4 below) experiences a DLT in Cycle 1, then the BLRM will be updated before any additional subject is enrolled to the current (higher) dose level; and (3) After each cohort, the SRC will meet and review data from the BLRM assessment and available safety (i.e., DLT and non-DLT data), PK, PD, and efficacy information. The final dose escalation decisions will be made by the SRC.

After repeating the above steps, a Compound A dose can be declared the MTD and/or RP2D after meeting the following conditions: at least six evaluable subjects have been treated at the dose; the posterior probability of targeted toxicity at the dose exceeds 60% and is the highest among the escalation doses or a minimum of 21 subjects have been treated on the study; and the dose is recommended according to the BLRM and the SRC approves it.

At the discretion of the SRC to better understand the safety, tolerability and PK of Compound A, additional cohorts of subjects may be enrolled at prior dose levels or to intermediate dose levels before or while proceeding with further dose escalation.

Provisional dose levels to be assigned to separate cohorts of subjects are described herein. Dose decisions during escalation are however not limited to these doses. Based on the recommendation of the BLRM regarding the highest dose that may not be exceeded at any decision point during escalation and the maximum increase in dose allowed by the protocol, intermediate doses may be administered to subsequent new cohorts of subjects. The decision to evaluate additional subjects within a dose cohort, a higher dose cohort, intermediate dose cohorts, smaller dose increments, alternate dosing schedules, or declare an MTD will also be determined by the SRC, based on their review of clinical and laboratory safety data.

All subjects who receive at least one dose of Compound A will be evaluable for safety. After the first dose is administered in any cohort during dose escalation, subjects in each cohort are observed for 28 days (Cycle 1, DLT window) before the next dose cohort can begin. No more than one subject per day will be enrolled in a given dose escalation cohort. A subject evaluable for DLT is defined as one that: Has received at least 10 of 12 doses (or ≥80% of the total planned dose intensity) of Compound A during Cycle 1 without experiencing a DLT; or Experienced a DLT after receiving at least one dose of Compound A.

Subjects non-evaluable for DLT are replaced. Additional subjects within any dose cohort may be enrolled at the discretion of the SRC. Intra-subject dose escalation will not be allowed during the DLT assessment period. The MTD is defined as the highest dose that results in ≤33% of the subjects experiencing DLTs during their first cycle of treatment. The estimation of MTD is described herein. A variable dose cohort (e.g., less frequent dosing) may be evaluated to accurately determine the MTD at the discretion of the SRC.

During dose escalation, the DLT assessment period is Cycle 1 (28 days). National Cancer Institute (NCI) Common Terminology Criteria for Adverse Events (CTCAE), Version 4.03 are used as a guide for the grading of severity of adverse events. A DLT is defined as any of the following toxicities occurring within the DLT assessment unless the event can clearly be determined to be unrelated to Compound A. Dose-limiting toxicities are: (1) Any Grade 4 nonhematologic toxicity of any duration; (2) Any non-hematologic toxicity Grade ≥3 EXCEPT for: (a) Grade 3 diarrhea, nausea, or vomiting of ≤3 days duration (with optimal medical management). (b) Grade 3 rash of the acneiform, pustular or maculopapular type which resolves to Grade ≤2 within 7 days of study drug interruption and does not recur at the same level with resumption of study drug at the same dose (with optimal medical management). (c) Grade 3 fatigue which resolves to Grade ≤2 within 7 days of study drug interruption and does not recur at the same level with resumption of study drug at the same dose (with optimal medical management); (3) Hematological toxicities as follows: Febrile neutropenia; Grade 4 neutropenia lasting >7 days; Grade 4 thrombocytopenia lasting >7 days, Grade ≥3 thrombocytopenia with clinically significant bleeding; (4) Any AE, unless clearly determined to be unrelated to the drug, necessitating dose-level reduction during Cycle 1: and (5) Possibly a sustained grade 3 hyperglycemia (×2 at least 24 hr apart) or symptomatic fasting grade 3 or higher hyperglycemia.

Isolated laboratory changes without associated clinical signs or symptoms (e.g., hypomagnesemia, hypermagnesemia, hypoalbuminemia, hypophosphatemia, lymphocyte count increased or decreased) may not be included in this definition. These findings are discussed and reviewed by the SRC.

Criteria for dose escalation in the next cohort of subjects are assessed as follows. Cohorts consist of at least three evaluable subjects. The SRC makes all final dose escalation decisions. The decision criteria for dose escalation are: (1) If no more than 0 of three or 1 of 6 evaluable subjects experience DLT within the DLT window in a dose cohort, dose escalation to the next higher dose cohort may occur. Additional subjects are enrolled to expand the cohort to 6 evaluable subjects if less than 6 subjects are evaluable when the DLT is observed; (2) If two or more of up to 6 evaluable subjects experience a DLT within the DLT window in a dose cohort, any further recruitment ceases and this dose is defined as the NTD; and (3) SRC determines if additional subjects are enrolled at lower dose cohorts to have 6 evaluable subjects in order to define MTD, or whether an intermediate dose cohort or alternative schedule is explored in up to 6 newly enrolled subjects.

The number of cohorts depends on incidence of DLT. A subject may experience more than one DLT. Dose escalation decisions are based on the number of subjects experiencing DLT events.

During Part A, the dose escalation stopping rules are described herein. Dose reductions are permitted in any cycle, including Cycle 1. Dose reductions that occur in Cycle 1 during dose escalation will constitute DLT as outlined, but subjects are allowed to continue on Compound A at a reduced dose. When a dose reduction is indicated, the next lower dose cohort will be selected or a less frequent dosing schedule. Two dose reductions are allowed. Once the dose has been reduced, it can be escalated when toxicity reaches Grade ≤1. If toxicity recurs at the higher dose, the dose is reduced a second time, but no re-escalation is then permitted. If any subject continues to experience unacceptable toxicity after two dose reductions (one for the starting dose), Compound A is discontinued permanently. Intra-subject dose escalation is not be allowed during the DLT assessment period.

Further regarding dose reduction, any AE meeting the definition of DLT requires dose interruption. Doses should be delayed if any Grade ≥2 toxicities are not resolved to Grade ≤1 by the time of the next dose. Grade ≥3 toxicity or chronic Grade 2 toxicity may warrant dose reduction of Compound A. Such cases should be discussed with the Sponsor (medical monitor and study physician) before dosing changes are made.

Further regarding criteria for dose increase, in Part A (escalation phase), intrasubject dose escalation beyond the doses initially assigned to a subject is not permitted in Cycle 1. Those continuing to take Compound A beyond Cycle 2 may, following approval by the SRC, have the dose increased providing the alternative dose has been shown to be well tolerated by at least one cohort of subjects in this study (i.e., overdose risk is less than 25% based on the BLRM assessment). In the event of intra-subject dose escalation and with (optional) subject consent, blood is withdrawn for PK assessments following the Cycle 1 Day 1 PK schedule for Part A. PK sampling occurs after at least 2 doses of Compound A at the higher dose in order to evaluate intra-subject Compound A PK. In Part B (expansion phase), no dose escalation beyond the MTD is allowed.

Treatment may be interrupted up to four weeks until toxicity (excluding alopecia) reaches either Grade ≤1 or baseline levels. Treatment may restart either at the same, or a reduced dose, at the Investigator's discretion or as described herein. Any such treatment interruptions must be discussed with the Sponsor medical monitor.

In the DLT assessment period of the dose escalation phase, a treatment interruption with >2 missed doses of Compound A for reasons other than DLT will make a subject non-evaluable for DLT and necessitate replacement of that subject in the dosing cohort. Any such treatment interruptions must be discussed with the sponsor study monitor.

Regarding management of select adverse events such as Neutropenia, Thrombocytopenia, and Anemia, hematopoietic growth factors or other hematologic support, such as erythropoietin, darbepoetin, granulocyte-colony stimulating factor (G-CSF), granulocyte-macrophage colony stimulating factor (GM-CSF), RBC- or platelet- transfusions are allowed in the study with therapeutic intent. Therapeutic use of G-CSF is allowed at any time for subjects experiencing Grade 3/4 neutropenia or any grade febrile neutropenia. Prophylactic use of granulocyte (or granulocyte-macrophage) growth factors is not allowed during Cycle 1. Subjects with Grade 3 or 4 neutropenia should be monitored frequently with laboratory tests until resolution to Grade ≤1. Antimicrobial, antifungal, and antiviral prophylaxis should be considered. For pain, tumor pain or treatment-induced pain can be controlled with opioid and opioid-related analgesics, such as codeine, meperidine, propoxyphene or morphine, administered at the clinician's discretion, and as dictated by medical need. The risk of bleeding, especially in the setting of thrombocytopenia, should be considered prior to use of non-steroidal anti-inflammatory drugs (NSAIDs) and aspirin.

For Gastrointestinal Effects, mucosa coating agents for protection of esophageal/gastric mucosa are recommended at the discretion of the Investigator as well as monitoring subjects for GI bleeding. Subjects are encouraged to report all episodes of GI discomfort or pain, appetite loss, or blood in stool. It is recommended that subjects experiencing diarrhea be managed according to the guideline provided in FIG. 7. Antidiarrheal medication, such as loperamide, should be initiated at the earliest onset of Grade 1-2 diarrhea. Antidiarrheal medication may be administered as prophylaxis and for treatment of diarrhea. Dehydration and electrolyte disturbances should be rapidly corrected. General measures to improve diarrhea, such as a low-fiber diet and increase liquid assumption, should be considered.

Changes in blood glucose were not observed in the nonclinical toxicology studies with Compound A. Preliminary clinical data of a new investigational BETi. OTX015, however, reported seven of thirty-seven patients with non-leukemic hematologic malignancies experienced Grade 1-2 hyperglycemia and 1 patient experienced Grade 3 hyperglycemia. Thieblemont, 2014. It is unknown whether hyperglycemia might be observed with Compound A and general guidelines for the management of possible hyperglycemia are provided in Appendix E.

Overdose, as defined for this protocol, refers to Compound A dosing only. On a per dose basis, an overdose is defined as the following amount over the protocol-specified dose of Compound A assigned to a given subject, regardless of any associated adverse events or sequelae: PO any amount over the protocol-specified dose.

On a schedule or frequency basis, an overdose is defined as anything more frequent than the protocol required schedule or frequency. Complete data about drug administration, including any overdose, regardless of whether the overdose was accidental or intentional, should be reported in the case report form.

Regarding method of treatment assignment, eligible subjects will be enrolled sequentially in Part A (dose escalation). Enrollment in Part B (dose expansion) will be stratified by disease cohort and dosing schedule, as applicable. An Interactive Response Technology (IRT) system will be used to track subject assignments to the dose levels in Part A and tumor cohorts in Part B.

The label(s) for Compound A includes the sponsor name, address and telephone number, the protocol number, Compound A, dosage form and strength (where applicable), amount of Compound A per container, lot number, expiry date (where applicable), medication identification/kit number, dosing instructions, storage conditions, and required caution statements and/or regulatory statements as applicable. Additional information may be included on the label as applicable per local regulations.

The investigator and relevant site personnel are trained on procedures for documenting receipt of Compound A, as well as the procedures for counting, reconciling Compound A, disposing of Compound A, and documenting these processes, as is review with the Investigator and relevant site personnel the process for Compound A return, disposal, or destruction including responsibilities for the site or appropriate designee.

Only the pharmacist or the Investigator's designee dispenses the Compound A formulation. A record of the number of capsules/tablets of Compound A dispensed to and taken by each subject must be maintained. The pharmacist or the Investigator's designee will document the doses dispensed/administered in the appropriate study records. Subjects use diary cards to record their daily self-administration of Compound A at home. The person completing the diary card signs/initials and dates the cards in accordance with good documentation practice. These are reviewed by study staff each time the subject visits the clinic. Entries are clarified, as necessary, so that appropriate information can be captured on the eCRFs. Study site personnel perform a Compound A administration compliance check and record this information on the subject's source documentation and on the appropriate eCRF.

All medications (excluding prior cancer therapy for the tumor under evaluation) taken beginning when the subject signs the ICD and all concomitant therapy during the study until 28 days after treatment discontinuation, together with dose, dose frequency and reasons for therapy use will be documented in the source documents and on the concomitant medication eCRF. All prior cancer therapy for the tumor under evaluation, including chemotherapy, biologic, immunologic, irradiation, and surgery, will be documented on dedicated prior cancer treatment eCRFs. The Investigator instructs subjects to notify the study staff about any new medications taken after signing the ICD. All medications and significant non-drug therapies (herbal medicines, physical therapy, etc.) and any changes in dosing with existing medications will be documented on the eCRFs. Subject to precautions, the use of any concomitant medication/therapies deemed necessary for the care of the subject should be used. Repeat PK evaluations may be conducted if changes are made to concomitant medications suspected of affecting drug absorption or metabolism.

The following are permitted concomitant medications and procedures: (1) Subjects with ≥Grade 1 diarrhea should promptly initiate treatment with diphenyoxylate/atropine (Lomotil), or loperamide (Imodium) or an alternative over-the-counter remedy for diarrhea. Premedication with antidiarrheal medication for subsequent doses of Compound A may be appropriate and should be discussed with medical monitor; (2) Anti-emetics will be withheld until subjects have experienced CTCAE ≥Grade 1 nausea or vomiting. Subjects may then receive prophylactic anti-emetics at the discretion of the investigator (3) Subjects may receive prophylactic mucosa protective agents at the discretion of the investigator; (4) Therapeutic use of granulocyte growth factors is allowed at any time for subjects experiencing febrile neutropenia or Grade 3/4 neutropenia. Routine prophylaxis with granulocyte colony stimulating factor or granulocyte-macrophage colony stimulating factor is allowed at Investigator discretion starting with Cycle 2 and beyond; (5) Subjects receiving stable doses of recombinant erythropoietin or darbepoetin alfa for at least 4 weeks prior to starting the Compound A may continue their pretreatment doses throughout the study. Subjects may initiate de novo treatment with erythropoietin stimulating agents (ESAs) beginning in Cycle 2 for hypoproliferative anemias secondary to prior chemotherapy exposure provided there is no clinical suspicion of a concurrent cause for the anemia (e.g., Compound A-induced); (6) Parenteral flu vaccination is permitted; (7) Routine infectious disease prophylaxis is not required. Antibiotic, antiviral, antipneumocystis, antifungal, or other prophylaxis may be implemented during the study at the discretion of the Investigator; (8) Treatment with bisphosphonates (e.g., pamidronate, zolendronate) or other agents (e.g., denosumab) is permitted to prevent or delay progression of bone metastases. Maintenance of a stable dosing regimen throughout the study is recommended; (9) Focal palliative radiotherapy for treatment of cancer-related symptoms (e.g., localized bone pain) is allowed during study treatment at the discretion of the investigator; (10) Subjects may receive physiologic replacement doses of glucocorticoids (up to the equivalent of 10 mg daily prednisone) as maintenance therapy for adrenal insufficiency; and (11) Maintenance hormonal therapies are allowed in subjects with a history of breast or prostate cancer.

Other investigational therapies must not be used while the subject is on the study. Anticancer therapy (chemotherapy, biologic or investigational therapy, and surgery) other than the study treatments must not be given to subjects while the subject is on the study. If such treatment is required, the subject must be discontinued from the study. Treatment with chronic, therapeutic dosing of anti-coagulants (e.g., warfarin, low molecular weight heparin. Factor Xa inhibitors) is not allowed. Short-term, prophylactic dosing of anticoagulants may be considered in subjects if medically indicated (e.g., hospitalized subjects, post-operatively).

Regarding statistical considerations, the primary objectives of this study are to determine the safety, tolerability, and MTD of Compound A when administered orally on a 3/7-day schedule to adult subjects with advanced solid tumors and relapsed/refractory NHL, and to determine its PK characteristics. The secondary objective is to make a preliminary assessment of the antitumor activity of Compound A. Data summaries/statistical analyses are performed by study part (Part A or B), dose level (Part A), and tumor cohort (Part B) as applicable. Study Population Definitions are as follows: (1) Enrolled Population—All subjects who are assigned an enrollment number and meet inclusion/exclusion criteria; (2) Treated.

Population—All subjects who enroll and receive at least one dose of Compound A; (3) Efficacy Evaluable (EE) Population—All subjects who enroll in the study, meet eligibility criteria, complete at least one cycle of Compound A (taking at least 80% of assigned doses), and have baseline and at least one valid post-baseline tumor assessment; (4) Pharmacokinetic (PK) Evaluable Population—all subjects who enroll and receive at least one dose of Compound A and have at least one measurable concentration of Compound A; and (5) Biomarker Evaluable (BE) Population—all subjects who enroll, receive at least one dose of study drug, and have at least one biomarker assessment, excluding disqualified assessments:

During Part A of the study, an adaptive Bayesian logistic regression (BLR) model (with 2 parameters) guided by the escalation with overdose control (EWOC) principle. No formal statistical power calculations to determine sample size were performed for this study. The actual number of subjects will depend on the number of dose levels/cohorts that are tested. The anticipated number of subjects is approximately forty. After the MTD or RPTD is determined from Part A, Part B will enroll approximately 14 to up to 20 additional subjects per pre-specified tumor types.

For Part B, sample sizes are not determined based on power calculation but rather on clinical, empirical and practical considerations traditionally used for exploratory studies of this kind. Enrollment in a tumor-specific cohort will be stopped for futility if there are no objective responses or fewer than 3 subjects with stable disease lasting at least 4 mo (i.e., two or more post-baseline, tumor assessment time points) from among the first 14 subjects within a tumor type. If at least one objective response or 3 subjects with stable disease lasting ≥4 mo is observed from among the first 14 efficacy-evaluable subjects enrolled, up to 6 more subjects will enroll for a total of 20 evaluable subjects in the cohort. If the response rate is 20%, the probability of seeing no response in the first 14 subjects will be 4.4%. If the rate of stable disease lasting for at least 4 mo is 40%, the probability of seeing fewer than three subjects with stable disease lasting for at least 4 mo will be 4%. If there are more SDs then objective responses, disease control rate rather than ORR may be assessed.

In Part A, the baseline characteristics of subjects will be summarized by dose cohort for the enrolled population. In Part B, the baseline characteristics of subjects is summarized by tumor type. The age, weight, height and other continuous demographic and baseline variables will be summarized using descriptive statistics. Performance status, gender, race and other categorical variables will be summarized with frequency tabulations. Medical history data is summarized using frequency tabulations by system organ class and preferred term.

Subject disposition (analysis population allocation, on-going, discontinued, along with primary reason) from treatment and study is summarized using frequency and percent. A summary of subjects enrolled by site is provided. Protocol violations are summarized using frequency tabulations. Supportive corresponding subject listings are also provided.

Efficacy analyses are based on the treated population and include summaries of disease control rate (DCR), objective response rate (ORR), duration of response or stable disease, progression-free survival (PFS), and OS by dose cohort and dosing schedule (Part A) or tumor type and dosing schedule (Part B). Tumor response (CR, PR, SD, PD, or inevaluable) is assessed by investigators according to Response Evaluation Criteria in Solid Tumors (RECIST), version 1.1 and IWG criteria. The DCR is defined as the percent of subjects whose best response is CR, PR or SD. The ORR is defined as the percent of subjects whose best response is CR or PR. When SD is the best response, it must be documented radiographically at least once after study entry after a minimal interval of 7 weeks (i.e., coincident with the first post baseline response assessment time point minus assessment window). If the minimal time for a best response of SD is not met, the subject's best response will depend on the outcome of subsequent assessments. For example, a subject who exhibits SD at first assessment (where the first assessment does not meet minimal duration criteria for SD) and PD at the second assessment, would be classified as having a best response of PD. A subject lost to follow-up after the first SD assessment would be considered non-evaluable, if the minimal duration criteria for SD are not met.

Two-sided 95% Clopper-Pearson exact confidence intervals are provided for ORR and DCR estimates. Similar analyses will be performed to include those subjects with confirmed responses as well as for the Efficacy Evaluable population. For subjects with best response of CR or PR, duration of response is measured from the time when criteria for CR/PR are first met (whichever is first recorded) until the first date at which progressive disease is objectively documented. For subjects with best response of SD, duration of SD is measured from the first dose date until the criteria for progression are met. If progression is not documented prior to Compound A discontinuation, duration of overall response, and duration of SD will be censored at the date of the last adequate tumor assessment.

Duration of response/SD based on investigators' assessments will be summarized by descriptive statistics (mean, standard deviation, median, minimum and maximum) for the treated population. Except for medians, which will be calculated based on both observed and censored values using the Kaplan-Meier method, all other statistics (mean, standard deviation, minimum and maximum) are calculated based on observed values only.

Progression-Free Survival (PFS) is defined as the time from the first dose of Compound A to the first occurrence of disease progression or death from any cause. Subjects who neither progress nor die at a data cut-off date are censored at the date of their last adequate tumor assessment. The PFS is summarized using descriptive statistics (mean, standard deviation, median, minimum and maximum) for the treated population. Except for the median, which is calculated based on both observed and censored values using the Kaplan-Meier method, all other statistics (mean, standard deviation, minimum and maximum) is calculated based on observed values only.

Overall Survival (OS) is measured as the time from the first dose of Compound A to death due to any cause and is analyzed in a manner similar to that described for PFS.

Adverse events, including treatment-emergent adverse events (TEAEs), laboratory assessments, vital signs. ECG results, ECOG performance status, LVEF assessments, physical examinations, vital signs, exposure to study treatment, assessment of concomitant medications, and pregnancy testing for females of childbearing potential are summarized for the treated population (by dose cohort in Part A and tumor type in Part B).

Adverse events observed are classified using the Medical Dictionary for Regulatory Activities (MedDRA), Version 17.1 or higher, system organ class (SOC) and preferred term (PT). In the by-subject analysis, a subject having the same AE more than once is counted only once. All adverse events are summarized by SOC, PT, and NCI CTCAE grade (Version 4.0 or higher). Adverse events leading to discontinuation of study treatment, those classified as Grade 3 or 4, study drug-related AEs, and SAEs (including deaths) are tabulated separately. By-subject listings of all AEs, TEAEs, SAEs (including deaths), and their attribution are provided.

Clinical laboratory results are summarized descriptively by dose cohort (Part A) or tumor type (Part B) and visit, which also includes a display of change from baseline. Shift tables demonstrating the changes (low/normal/high) from baseline to worst post-baseline laboratory value are displayed in cross-tabulations by dose cohort (Part A) or tumor type (Part B). Similar shift tables demonstrating the change of NCI CTCAE grades from baseline to the worst post-baseline severity grade during the treatment period are presented by dose cohort (Part A) or tumor type (Part B) for applicable analytes. Listings of abnormal clinical laboratory data according to NCI CTCAE severity grades (if applicable), abnormal flags (low or high) and clinical significance of the latter are provided.

Graphical displays (e.g., "spaghetti" plots or box plots) are provided for key laboratory analytes. Descriptive statistics for vital signs, both observed values and changes from baseline, are summarized by dose cohort (Part A) or tumor type (Part B) and visit. Shift tables demonstrating the changes from baseline to the worst post-baseline value is displayed in cross-tabulations by dose cohort (Part A) or tumor type (Part B). Vital sign measurements are listed by subject and by visit. ECG parameters and changes from baseline is summarized by dose cohort (Part A) or tumor type (Part B) and visit using descriptive statistics. Post-baseline abnormal QTc (both QTcF and QTcB) values are summarized using frequency tabulations for the following five categories:

(1) QTc >450 msec; (2) QTc >480 msec; (3) QTc >500 msec; (4) QTc increase from baseline >30 msec; (5) QTc increase from baseline >60 msec.

Shift from baseline to worst post-baseline qualitative assessment of abnormality (i.e., 'Normal', 'Abnormal, not clinically significant', and 'Abnormal, clinically significant' or 'Normal' and 'Abnormal') are displayed in cross-tabulations by dose cohort (Part A) or tumor type (Part B). A listing of ECG parameters by subject, by visit will be provided.

No formal interim analysis is planned. Data is reviewed on an ongoing basis.

Figure 5:
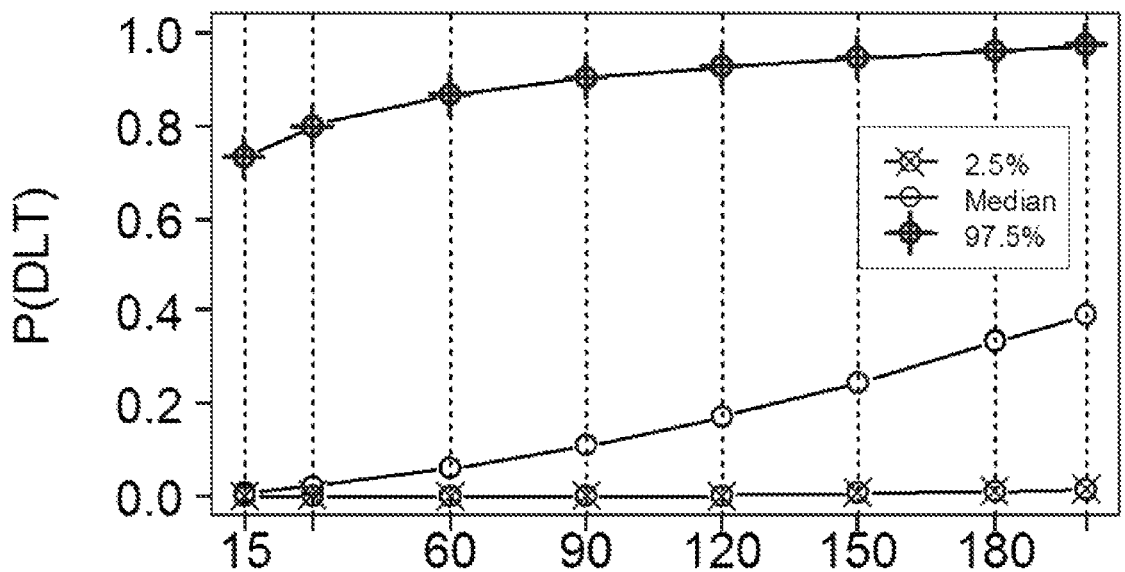
FIG. 5 relates the probability of dose-limiting toxicity (DLT) according to prior distribution. □ SE; ○ SM; Δ SL; +FM; x FL.

Regarding statistical method for dose escalation, an adaptive BLRM guided by the escalation with EWOC principle will be used to make dose recommendations and estimate the MTD during the escalation phase of the study (refer to Appendix H). The DLT relationship in the escalation part of the study will be described by the following Bayesian logistic regression model:

$$\log(p_j/1-p_j)=\log\alpha+\beta\cdot\log(d_j/d^*), \alpha>0, \beta>0$$

in which each $p_j$ is the DLT rate at each dose; each $d_j$ is dose levels; $d^*$=90 mg is reference dose; $\alpha$ is odds of DLT at $d^*$. Regarding prior specifications, prior for ($\log(\alpha)$, $\log(\beta)$): A vague bivariate normal prior for the model parameters ($\log(\alpha)$, $\log(\beta)$) is elicited based on prior guesses (medians) from preclinical data and wide confidence intervals for the probabilities of a DLT at each dose. Prior MTD is assumed to be 180 mg based on preclinical data. The probability of DLT for the first dose is assumed to be low. The parameters of the prior distributions of model parameters are selected based on the method to construct weakly informative prior as described in Neuenschwander et al. (2015), and are provided in Table 6. FIG. 5 illustrates the resulting prior distribution of DLT rate derived from the prior given in Table 6:

TABLE 6

Prior Parameters for Bivariate Normal Distribution of Model Parameters

| Parameters | Means | Standard Deviation | Correlation |
|---|---|---|---|
| log(α), log(β) | (−0.693, 0.3936) | (2, 1) | 0 |

The provisional dose levels are: 15 mg, 30 mg, 60 mg, 90 mg, 120 mg, 150 mg, 180 mg, and 200 mg. It is possible for some doses to be skipped or additional dose levels to be added during the course of the study, based on emerging safety information. After each cohort of subjects the posterior distributions for the probabilities of a DLT rates at different dose levels are obtained. The results of this analysis are summarized in terms of the estimated probabilities that the true rate of DLT at each dose-level will have of lying in each of the following intervals: [0, 0.16] under-dosing; [0.16, 0.33] targeted toxicity: [0.33, 1.00] excessive toxicity.

Following the principle of escalation with EWOC, after each cohort of subjects the recommended dose is the one with the highest posterior probability of the DLT rate falling in the target interval (16%, 33%) among the doses fulfilling EWOC, i.e., it is unlikely (<25% posterior probability) that the DLT rate at the dose falls in the excessive toxicity interval.

Note that the dose that maximizes the posterior probability of targeted toxicity is the best estimate of the MTD, but it may not be an admissible dose according to the overdose criterion if the amount of data is insufficient. If vague prior information is used for the probabilities of DLT, in the early stages of the study this escalation procedure will reflect a conservative strategy.

The dose recommended by the adaptive Bayesian logistic model may be regarded as guidance and information to be integrated with a clinical assessment of the toxicity profiles observed at the time of the analysis in determining the next dose level to be investigated.

Regarding the assessment of pharmacokinetics, plasma PK parameters such as $AUC_{24h}$, $C_{max}$, $T_{max}$, $t_{1/2}$, CL/F, and Vz/F of Compound A are calculated by the noncompartmental analysis method from the plasma concentration-time profiles of Compound A. Additional PK parameters may be calculated, if data permits. Summary statistics including number of subjects (N), mean, standard deviation (SD), coefficient of variation (CV %), geometric mean, geometric CV %, median, minimum, and maximum are provided for Compound A concentration by nominal time point, study day, and dose cohort. Mean and individual plots of plasma concentrations are presented in both original and semi-logarithmic scales. Summary statistics are provided for Compound A PK parameters by study day and dose cohort and be presented in tabular form. The relationship between Compound A dose, plasma exposures, and selected clinical endpoints (e.g., measures of toxicities, effectiveness, and/or biomarkers) may be explored.

For assessment of pharmacodynamics, descriptive statistics (N, mean, SD, median, min, and max) will be provided for baseline, post-baseline values, and changes from baseline or percent change from baseline of each biomarker by dose cohort (Part A) or tumor type (Part B) and visit. Subjects' biomarker results over time will be plotted. Comparison of biomarker levels before and during treatment will be performed by Wilcoxon signed rank test. If sufficient and valid results from biomarker assays can be obtained, the relationship between percent changes in biomarker levels and clinical endpoints including ORR and DCR are explored.

Further regarding adverse events, in particular the monitoring, recording and reporting of adverse events, an AE is any noxious, unintended, or untoward medical occurrence that may appear or worsen in a subject during the course of a study. It may be a new intercurrent illness, a worsening concomitant illness, an injury, or any concomitant impairment of the subject's health, including laboratory test values, regardless of etiology. Any worsening (i.e., any clinically significant adverse change in the frequency or intensity of a pre-existing condition) should be considered an AE. A diagnosis or syndrome should be recorded on the AE page of the CRF rather than the individual signs or symptoms of the diagnosis or syndrome. Abuse, withdrawal, sensitivity or toxicity to an investigational product (IP) should be reported as an AE. Overdose, accidental or intentional, whether or not it is associated with an AE should be reported on the overdose CRF. Any sequela of an accidental or intentional overdose of an investigational product should be reported as an AE on the AE CRF. If the sequela of an overdose is an SAE, then the sequela must be reported on an SAE report form and on the AE CRF. The overdose resulting in the SAE should be identified as the cause of the event on the SAE report form and CRF but should not be reported as an SAE itself.

In the event of overdose, the subject should be monitored as appropriate and should receive supportive measures as necessary. There is no known specific antidote for Compound A overdose. Actual treatment should depend on the severity of the clinical situation and the judgment and experience of the treating physician.

All subjects will be monitored for AEs during the study. Assessments may include monitoring of any or all of the following parameters: the subject's clinical symptoms, laboratory, pathological, radiological or surgical findings, physical examination findings, or findings from other tests and/or procedures.

All AEs are recorded by the Investigator from the time the subject signs informed consent until 28 days after the last dose of Compound A as well as those SAEs made known to the Investigator at any time thereafter that are suspected of being related to Compound A. AEs and SAEs are recorded on the AE page of the CRF and in the subject's source documents. All SAEs must be reported to Drug Safety within 24 hours of the Investigator's knowledge of the event by facsimile, or other appropriate method, using the SAE Report Form, or approved equivalent form.

A qualified Investigator evaluates all adverse events as to Seriousness. A SAE is any AE occurring at any dose that: Results in death; Is life-threatening (i.e., in the opinion of the Investigator, the subject is at immediate risk of death from the AE); Requires inpatient hospitalization or prolongation of existing hospitalization (hospitalization is defined as an inpatient admission, regardless of length of stay); Results in persistent or significant disability/incapacity (a substantial disruption of the subject's ability to conduct normal life functions): Is a congenital anomaly/birth defect; or Constitutes an important medical event.

Important medical events are defined as those occurrences that may not be immediately life-threatening or result in death, hospitalization, or disability, but may jeopardize the subject or require medical or surgical intervention to prevent one of the other outcomes listed above. Medical and scientific judgment should be exercised in deciding whether such an AE should be considered serious.

Events not considered to be SAEs are hospitalizations for: a standard procedure for protocol therapy administration. Hospitalization or prolonged hospitalization for a complication of therapy administration is reported as an SAE; routine treatment or monitoring of the studied indication not associated with any deterioration in condition; the administration of blood or platelet transfusion as routine treatment of studied indication (hospitalization or prolonged hospitalization for a complication of such transfusion remains a reportable SAE); a procedure for protocol/disease-related investigations (e.g., surgery, scans, endoscopy, sampling for laboratory tests, bone marrow sampling) (hospitalization or prolonged hospitalization for a complication of such procedures remains a reportable SAE); hospitalization or prolongation of hospitalization for technical, practical, or social reasons, in absence of an AE; a procedure that is planned (i.e., planned prior to start of treatment on study) must be documented in the source document and the CRF (hospitalization or prolonged hospitalization for a complication remains a reportable SAE); an elective treatment of or an elective procedure for a pre-existing condition, unrelated to the studied indication, that has not worsened from baseline: or emergency outpatient treatment or observation that does not result in admission, unless fulfilling other seriousness criteria described above.

If an AE is considered serious, both the AE page/screen of the CRF and the SAE Report Form must be completed. For each SAE, the Investigator will provide information on severity, start and stop dates, relationship to the IP, action taken regarding the IP, and outcome.

For both AEs and SAEs, the Investigator must assess the severity/intensity of the event. The severity/intensity of AEs will be graded based upon the subject's symptoms according to the current active minor version of the Common Terminology Criteria for Adverse Events (CTCAE, Version 4.03), available at the CTEP cancer website, under protocol Development.

AEs that are not defined in the CTCAE should be evaluated for severity/intensity according to the following scale: Grade 1=Mild—transient or mild discomfort; no limitation in activity; no medical intervention/therapy required; Grade 2=Moderate—mild to moderate limitation in activity, some assistance may be needed; no or minimal medical intervention/therapy required; Grade 3=Severe—marked limitation in activity, some assistance usually required; medical intervention/therapy required, hospitalization is possible: Grade 4=Life-threatening—extreme limitation in activity, significant assistance required; significant medical intervention/therapy required, hospitalization or hospice care probable; and Grade 5=Death—the event results in death.

The term "severe" is often used to describe the intensity of a specific event (as in mild, moderate or severe myocardial infarction); the event itself, however, may be of relatively minor medical significance (such as severe headache). This criterion is not the same as "serious" which is based on subject/event outcome or action criteria associated with events that pose a threat to a subject's life or functioning. Seriousness, not severity, serves as a guide for defining regulatory obligations.

Causality is assessed. The Investigator must determine the relationship between the administration of the Compound A and the occurrence of an AE/SAE as Not Suspected or Suspected as defined below:

Not suspected: a causal relationship of the adverse event to Compound A administration is unlikely or remote, or other medications, therapeutic interventions, or underlying conditions provide a sufficient explanation for the observed event.

Suspected: there is a reasonable possibility that the administration of Compound A caused the adverse event. 'Reasonable possibility' means there is evidence to suggest a causal relationship between the IP and the adverse event.

Causality should be assessed and provided for every AE/SAE based on currently available information. Causality is to be reassessed and provided as additional information becomes available. If an event is assessed as suspected of being related to a comparator, ancillary or additional Compound A that has not been manufactured or provided by the Sponsor, please provide the name of the manufacturer when reporting the event.

Regarding duration, for both AEs and SAEs, the Investigator provides a record of the start and stop dates of the event. The Investigator reports the action taken with IP as a result of an AE or SAE, as applicable (e.g., discontinuation, interruption, or dose reduction of IP, as appropriate) and report if concomitant and/or additional treatments were given for the event. The Investigator reports the outcome of the event for both AEs and SAEs. All SAEs that have not resolved upon discontinuation of the subject's participation in the study must be followed until recovered (returned to baseline), recovered with sequelae, or death (due to the SAE).

Regarding Abnormal Laboratory Values, an abnormal laboratory value is considered to be an AE if the abnormality: (a) results in discontinuation from the study; (b) requires treatment, modification/interruption of Compound A dose, or any other therapeutic intervention; or (c) is judged to be of significant clinical importance, e.g., one that indicates a new disease process and/or organ toxicity, or is an exacerbation or worsening of an existing condition.

Regardless of severity grade, only laboratory abnormalities that fulfill a seriousness criterion need to be documented as a serious adverse event. If a laboratory abnormality is one component of a diagnosis or syndrome, then only the diagnosis or syndrome should be recorded on the AE page/screen of the CRF. If the abnormality was not a part of a diagnosis or syndrome, then the laboratory abnormality should be recorded as the AE. If possible, the laboratory abnormality should be recorded as a medical term and not simply as an abnormal laboratory result (e.g., record thrombocytopenia rather than decreased platelets).

All pregnancies or suspected pregnancies occurring in either a female subject of childbearing potential or partner of childbearing potential of a male subject are immediately reportable events. The exposure of any pregnant female (e.g., caregiver, pharmacist, study coordinator or monitor) to Compound A is also an immediately reportable event. Pregnancies and suspected pregnancies (including elevated β-hCG or positive pregnancy test in a female subject of childbearing potential regardless of disease state) occurring while the subject is on Compound A, or within three months (to be determined) of the subject's last dose of Compound A are considered immediately reportable events. Investigational product is to be discontinued immediately. The pregnancy, suspected pregnancy, or positive pregnancy test must be reported to Sponsor Drug Safety immediately by email, phone or facsimile, or other appropriate method, using the Pregnancy Initial Report Form, or approved equivalent form.

The female subject should be referred to an obstetrician-gynecologist, preferably one experienced in reproductive toxicity for further evaluation and counseling. The Investigator follows the female subject until completion of the pregnancy, and must notify Sponsor Drug Safety immediately about the outcome of the pregnancy (either normal or abnormal outcome) using the Pregnancy Follow-up Report Form, or approved equivalent form. If the outcome of the pregnancy was abnormal (e.g., spontaneous abortion), the Investigator will report the abnormal outcome as an AE. If the abnormal outcome meets any of the serious criteria, it must be reported as an SAE to Sponsor Drug Safety by facsimile, or other appropriate method, within 24 hr of the Investigator's knowledge of the event using the SAE Report Form. or approved equivalent form. All neonatal deaths that occur within 28 days of birth are reported, without regard to causality, as SAEs. In addition, any infant death after 28 days that the Investigator suspects is related to the in utero exposure to the Compound A should also be reported to Sponsor Drug Safety by facsimile, or other appropriate method, within 24 hours of the Investigator's knowledge of the event using the SAE Report Form, or approved equivalent form.

For male subjects, if a female partner of a male subject taking Compound A becomes pregnant, the male subject taking Compound A should notify the Investigator, and the pregnant female partner should be advised to call their healthcare provider immediately. Where applicable, the Compound A may need to be discontinued in the male subject, but may be resumed later at the discretion of the Investigator and medical monitor.

Any AE that meets any criterion for an SAE requires the completion of an SAE Report Form in addition to being recorded on the AE page/screen of the CRF. All SAEs are reported to Sponsor Drug Safety within 24 hr of the Investigator's knowledge of the event by facsimile, or other appropriate method (e.g., via email) using the SAE Report Form, or approved equivalent form. This instruction pertains to initial SAE reports as well as any follow-up reports. The Investigator is required to ensure that the data on these forms is accurate and consistent. This requirement applies to all SAEs (regardless of relationship to Compound A) that occur during the study (from the time the subject signs informed consent until 28 days after the last dose of Compound A) or any SAE made known to the Investigator at any time thereafter that are suspected of being related to Compound A. Serious adverse events occurring prior to treatment (after signing the ICD) will be captured. The SAE report should provide a detailed description of the SAE and include a concise summary of hospital records and other relevant documents. If a subject died and an autopsy has been performed, copies of the autopsy report and death certificate are to be sent to Sponsor Drug Safety as soon as these become available. Any follow-up data should be detailed in a subsequent SAE Report Form, or approved equivalent form, and sent to Sponsor Drug Safety. Where required by local legislation, the Investigator is responsible for informing the Institutional Review Board/Ethics Committee (IRB/EC) of the SAE and providing them with all relevant initial and follow-up information about the event. The Investigator must keep copies of all SAE information on file including correspondence with Sponsor and the IRB/EC.

Queries pertaining to SAEs are communicated from Drug Safety to the site via facsimile or electronic mail. The response time is expected to be no more than five (5) business days. Urgent queries (e.g., missing causality assessment) may be handled by phone.

For the purpose of regulatory reporting. Drug Safety determines the expectedness of events suspected of being related to Compound A based on an Investigator Brochure. In the United States, all suspected unexpected serious adverse reactions (SUSARs) are reported in an expedited manner in accordance with 21 CFR 312.32. For countries within the European Economic Area (EEA), an authorized representative reports in an expedited manner to Regulatory Authorities and Ethics Committees concerned, suspected unexpected serious adverse reactions (SUSARs) in accordance with Directive 2001/20/EC and the Detailed Guidance on collection, verification and presentation of adverse reaction reports arising from clinical trials on investigational products for human use (ENTR/CT3) and also in accordance with country specific requirements. Adverse events such as disease progression, death related to disease progression (in the absence of serious Compound A-related events) and serious events due to the relapse of the studied indication will not be subject to expedited reporting by the Sponsor to regulatory authorities.

An authorized representative shall notify the Investigator of the following information: (1) Any AE suspected of being related to the use of Compound A in this study or in other studies that is both serious and unexpected (e.g., SUSAR); (2) Any finding from tests in laboratory animals that suggests a significant risk for human subjects including reports of mutagenicity, teratogenicity, or carcinogenicity.

Where required by local legislation, the Investigator shall notify his/her IRB/EC promptly of these new serious and unexpected AE(s) or significant risks to subjects. The Investigator must keep copies of all pertinent safety information on file including correspondence with the Compound A drug product supplier, responsible party, and the IRB/EC.

The following events are considered sufficient reasons for discontinuing a subject from the study treatment: Adverse Event; Withdrawal by subject; Lack of efficacy; Physician decision; Protocol violation; Progressive disease; Death; Lost to follow-up; Other (to be specified on the CRF).

The reason for discontinuation of treatment should be recorded in the CRF and in the source documents. The decision to discontinue a subject from treatment remains the responsibility of the treating physician, which will not be delayed or refused by the Sponsor. Prior to discontinuing a subject, however, the Investigator may contact the Medical Monitor and forward appropriate supporting documents for review and discussion.

The following events are considered sufficient reasons for discontinuing a subject from the study: Screen failure; Adverse event: Withdrawal by subject; Lack of efficacy; Physician decision; Protocol violation; Progressive disease; Death; Lost to follow-up; Other (to be specified on the CRF). The reason for study discontinuation should be recorded in the CRF and in the source documents.

This is an open-label study; therefore, Compound A is identified on the package labeling.

Subjects enrolled in the study are issued an identification card showing the name of this study and an emergency contact number. This can be used by health care professionals seeking emergency information about a subject's participation in the study.

The procedures set out in this study protocol pertaining to the conduct, evaluation, and documentation of this study are designed to ensure that Sponsor, its authorized representative, and Investigator abide by Good Clinical Practice (GCP), as described in International Conference on Harmonisation (ICH) Guideline E6 and in accordance with the general ethical principles outlined in the Declaration of Helsinki. The study will receive approval from an IRB/EC prior to commencement. The Investigator conducts all aspects of the study in accordance with applicable national, state, and local laws of the pertinent regulatory authorities.

Investigator responsibilities are set out in the ICH Guideline for Good Clinical Practice and in the local regulations. Staff or an authorized representative evaluate and approve all Investigators who in turn selects their staff. The Investigator should ensure that all persons assisting with the study are adequately informed about the protocol, amendments, study treatments, as well as study-related duties and functions, including obligations of confidentiality of Sponsor information. The Investigator should maintain a list of Sub-investigators and other appropriately qualified persons to whom he or she has delegated significant study-related duties. The Investigator is responsible for keeping a record of all subjects who sign an informed consent form (ICF) and are screened for entry into the study. Subjects who fail screening must have the reason(s) recorded in the subject's source documents. The Investigator, or a designated member of the Investigator's staff, must be available during monitoring visits to review data, resolve queries and allow direct access to subject records (e.g., medical records, office charts, hospital charts, and study-related charts) for source data verification. The Investigator must ensure timely and accurate completion of CRFs and queries.

The Investigator obtains informed consent of a subject and/or a subject's legal representative prior to any study related procedures. Documentation that informed consent occurred prior to the study subject's entry into the study and of the informed consent process should be recorded in the study subject's source documents including the date. The original ICF signed and dated by the study subject and by the person consenting the study subject prior to the study subject's entry into the study, must be maintained in the Investigator's study files and a copy given to the study subject. In addition, if a protocol is amended and it impacts on the content of the informed consent, the ICF must be revised. Study subjects participating in the study when the amended protocol is implemented must be re-consented with the revised version of the ICF. The revised ICF is signed and dated by the study subject and must be maintained in the Investigator's study files with a copy given to the study subject.

Any amendment to a study protocol must be approved by the Clinical Research Physician/Medical Monitor. Amendments are submitted to the IRB/EC for written approval. Written approval must be obtained before implementation of the amended version occurs. The written signed approval from the IRB/EC should specifically reference the Investigator name, protocol number, study title and amendment number(s) that is applicable. Amendments that are administrative in nature do not require IRB/IEC approval but will be submitted to the IRB/IEC for information purposes.

Before the start of the study, the study protocol, ICF, and any other appropriate documents is submitted to the IRB/EC with a cover letter or a form listing the documents submitted, their dates of issue, and the site (or region or area of jurisdiction, as applicable) for which approval is sought. If applicable, the documents will also be submitted to the authorities in accordance with local legal requirements. Investigational product can only be supplied to an Investigator by Sponsor or its authorized representative after documentation on all ethical and legal requirements for starting the study has been received by Sponsor or its authorized representative. This documentation must also include a list of the members of the IRB/EC and their occupation and qualifications. If the IRB/EC will not disclose the names, occupations and qualifications of the committee members, it should be asked to issue a statement confirming that the composition of the committee is in accordance with GCP. For example, the IRB General Assurance Number may be accepted as a substitute for this list. Formal approval by the IRB/EC should mention the protocol title, number, amendment number (if applicable), study site (or region or area of jurisdiction, as applicable), and any other documents reviewed. It must mention the date on which the decision was made and must be officially signed by a committee member. Before the first subject is enrolled in the study, all ethical and legal requirements must be met. The IRB/EC and, if applicable, the authorities, must be informed of all subsequent protocol amendments in accordance with local legal requirements. Amendments must be evaluated to determine whether formal approval must be sought and whether the ICF should also be revised. The Investigator must keep a record of all communication with the IRB/EC and, if applicable, between a Coordinating Investigator and the IRB/EC. This statement also applies to any communication between the Investigator (or Coordinating Investigator, if applicable) and regulatory authorities.

If required by legislation or the IRB/EC, the Investigator must submit to the IRB/EC: Information on serious or unexpected adverse events as soon as possible; Periodic reports on the progress of the study; and Deviations from the protocol or anything that may involve added risk to subjects.

The Sponsor reserves the right to terminate this study prematurely at any time for reasonable medical or administrative reasons. Any premature discontinuation is appropriately documented according to local requirements (e.g., IRB/EC, regulatory authorities, etc.). In addition, the Investigator or Sponsor has the right to discontinue a single site at any time during the study for medical or administrative reasons such as: Unsatisfactory enrollment; GCP noncompliance; Inaccurate or incomplete data collection: Falsification of records; or Failure to adhere to the study protocol.

Regarding data handling and recording, the Investigator must ensure that the records and documents pertaining to the conduct of the study and the distribution of the investigational product are complete, accurate, filed and retained. Examples of source documents include: hospital records; clinic and office charts; laboratory notes; memoranda; subject's diaries or evaluation checklists; dispensing records; recorded data from automated instruments; copies or transcriptions certified after verification as being accurate copies; microfiche: x-ray film and reports; and records kept at the pharmacy, and the laboratories, as well as copies of CRFs or CD-ROM.

Data is collected via CRF and entered into the clinical database per Sponsor SOPs. This data is verified electronically through use of programmed edit checks specified by the clinical team. Discrepancies in the data are brought to the attention of the clinical team, and investigational site personnel, if necessary. Resolutions to these issues are reflected in the database. An audit trail within the system tracks all changes made to the data.

Essential documents must be retained by the Investigator according to the period of time outlined in the clinical trial agreement. The Investigator must retain these documents for the time period described above or according to local laws or requirements, whichever is longer. Essential documents include, but are not limited to, the following: Signed ICFs for all subjects; Subject identification code list, screening log (if applicable), and enrollment log; Record of all communications between the Investigator and the IRB/EC; Composition of the IRB/EC; Record of all communications between the Investigator, Sponsor, and their authorized representative(s); List of Sub-investigators and other appropriately qualified persons to whom the Investigator has delegated significant study-related duties, together with their roles in the study, curriculum vitae, and their signatures; Copies of CRFs (if paper) and of documentation of corrections for all subjects; Compound A accountability records; Record of any body fluids or tissue samples retained: All other source documents (subject records, hospital records, laboratory records, etc.); All other documents as listed in Section 8 of the ICH consolidated guideline on GCP (Essential Documents for the Conduct of a Clinical Trial).

The Investigator must notify the Sponsor if he/she wishes to assign the essential documents to someone else, remove them to another location or is unable to retain them for a specified period. The Investigator must obtain approval in writing from the Sponsor prior to destruction of any records. If the Investigator is unable to meet this obligation, the Investigator must ask the Sponsor for permission to make alternative arrangements. Details of these arrangements should be documented. All study documents should be made available if required by relevant health authorities. Investigator or institution should take measures to prevent accidental or premature destruction of these documents.

All aspects of the study are monitored carefully by the Sponsor or its authorized representative for compliance with applicable government regulations with respect to current GCP and SOPs. Sponsor ensures that appropriate monitoring procedures are performed before, during and after the study. All aspects of the study are reviewed with the Investigator and the staff at a study initiation visit and/or at an Investigators' Meeting. Prior to enrolling subjects into the study, a representative reviews the protocol. CRFs, procedures for obtaining informed consent, record keeping, and reporting of AEs/SAEs with the Investigator. Monitoring includes on-site visits with the Investigator and his/her staff as well as any appropriate communications by mail, email, fax, or telephone. During monitoring visits, the facilities, investigational product storage area. CRFs, subject's source documents, and all other study documentation are inspected/reviewed by the Sponsor's representative in accordance with the Study Monitoring Plan.

Accuracy is checked by performing source data verification that is a direct comparison of the entries made onto the CRFs against the appropriate source documentation. Any resulting discrepancies are reviewed with the Investigator and/or his/her staff. Any necessary corrections will be made directly to the CRFs or via queries by the Investigator and/or his/her staff. Monitoring procedures require that informed consents, adherence to inclusion/exclusion criteria and documentation of SAEs and their proper recording be verified.

Additional monitoring activities may be outlined in a study-specific monitoring plan. In addition to the routine monitoring procedures, a Good Clinical Practice Quality Assurance unit exists within the Sponsor. Representatives of this unit will conduct audits of clinical research activities in accordance with Sponsor SOPs to evaluate compliance with Good Clinical Practice guidelines and regulations.

The Investigator is required to permit direct access to the facilities where the study took place, source documents, CRFs and applicable supporting records of study subject participation for audits and inspections by IRB/ECs, regulatory authorities (e.g., FDA, EMA, Health Canada) and company authorized representatives. The Investigator should make every effort to be available for the audits or inspections. If the Investigator is contacted by any regulatory authority regarding an inspection, he/she should contact the Sponsor immediately.

APPENDIX A

| Abbreviations | |
|---|---|
| Abbreviation or Specialist Term | Explanation |
| ADA | Anti-drug antibodies |
| ADCC | Antibody-dependent cellular cytotoxicity |
| ADL | Activity of daily life |
| AE | Adverse event |
| ALL | Acute lymphoid leukemia |
| ALT | Alanine aminotransferase (SGPT) |
| AML | Acute myeloid leukemia |
| ANC | Absolute neutrophil count |
| Ara-C | Cytarabine |
| AST | Aspartate aminotransferase (SGOT) |
| AUC | Area under the curve |
| β-hCG | β-subunit of human chorionic gonadotropin |
| BID | Twice a day |
| BM | Bone marrow |
| BMI | Body mass index |

APPENDIX A-continued

Abbreviations

| Abbreviation or Specialist Term | Explanation |
|---|---|
| BSA | Body surface area |
| BUN | Blood urea nitrogen |
| C | Cycle |
| CBC | Complete blood count |
| CD | Cluster of differentiation |
| CEBPα | CCAAT/enhancer binding protein alpha |
| CI | Confidence interval |
| c-Kit | Mast/stem cell growth factor receptor |
| CL | Clearance |
| Cmax | Maximum plasma concentration of drug |
| CNS | Central nervous system |
| CR | Complete remission |
| CRc | Cytogenetic complete remission |
| CRi | Complete remission with incomplete neutrophil recovery |
| CRp | Complete remission with incomplete platelet recovery |
| CRP | C-reactive protein |
| CRR | Complete remission rate |
| CRO | Contract research organization |
| CRF | Case report form |
| CRP | Clinical Research Physician |
| CRS | Clinical Research Scientist |
| CRT | Calreticulin |
| CT | Computed tomography |
| CTCAE | Common Terminology Criteria for Adverse Events |
| CV % | Coefficient of variation |
| DAT | Direct antiglobulin test |
| DCR | Disease control rate |
| DIC | Disseminated intravascular coagulation |
| DLT | Dose-limiting toxicity |
| DMC | Data Monitoring Committee |
| DOR | Duration of response |
| EC | Ethics Committee |
| ECG | Electrocardiogram |
| ECHO | Echocardiogram |
| ECOG PS | Eastern Cooperative Oncology Group Performance Status |
| eCRF | Electronic case report form |
| EEA | European Economic Area |
| ELISA | Enzyme-linked immunoassay |
| EOI | End of infusion |
| EOT | End of treatment |
| ESR | Erythrocyte sedimentation rate |
| FACS | Fluorescence-activated ceil sorting |
| FCBP | Females of child bearing potential |
| FCBP | Females of child bearing potential |
| FDA | Food and Drug Administration |
| FISH | Fluorescence in situ hybridization |
| FLT3 | Fms-related tyrosine kinase 3 |
| FLT3-ITD | Fms-related tyrosine kinase 3-internal tandem duplication |
| FOXP3 | Forkhead box P3 |
| GCP | Good Clinical Practice |
| GVHD | Graft-versus-host disease |
| HBV | Hepatitis B virus |
| HCV | Hepatitis C virus |
| HGB | Hemoglobin |
| HIV | Human immunodeficiency virus |
| HLA | Human leukocyte antigen |
| HNSTD | Highest non-severely toxic dose |
| HSCT | Hematopoietic stem cell transplant |
| huCD | Human cluster of differentiation |
| ICD | Informed consent document |
| ICF | Informed consent form |
| ICH | International Conference on Harmonisation |
| ICSH | International Council for Standardization in Hematology |
| IFN | Interferon |
| IgE | Immunoglobulin E subclass |
| IgG | Immunoglobulin G subclass |
| IL | Interleukin |
| IL-1β | Interleukin-1 beta |
| IND | Investigational New Drug |
| INR | International normalized ratio |
| IP | Investigational Product |
| IPSS-R | Revised International Prognostic Index Scoring System |
| IRB | Institutional Review Board |
| IRR | Infusion related reaction |
| IRT | Integrated Response Technology |
| IV | Intravenous |
| IVIG | Intravenous immunoglobulin |
| IWG | International working group |
| KC-GRO | Keratinocyte-derived cytokine-growth-regulated oncogene |
| LDH | Lactate dehydrogenase |
| LSC | Leukemia stem cell |
| LVEF | Left ventricular ejection fraction |
| mCR | Molecular complete remission |
| MCP-1 | Monocyte chemoattractant protein-1 |
| MDR | Multi-drug resistance |
| MDS | Myelodysplastic syndrome |
| MedDRA | Medical Dictionary for Regulatory Activities |
| MIP-1α | Macrophage inflammatory protein-1 alpha |
| MM | Multiple myeloma |
| MRI | Magnetic resonance imaging |
| MTD | Maximum tolerated dose |
| MUGA | Multi-gated acquisition |
| N | Number |
| NCI | National Cancer Institute |
| NHL | Non-Hodgkin's lymphoma |
| NOD-SCID | Non-obese diabetic, severe-combine immunodeficiency |
| NOAEL | No observed adverse effect level |
| NOEL | No observed effect level |
| NPM1 | Nucleophosmin 1 |
| NSG | Non-obese diabetic, severe-combine immunodeficiency γ |
| NTD | Non-tolerated dose |
| O2 | Oxygen |
| ORR | Objective response rate |
| OS | Overall survival |
| PBMC | Peripheral blood mononuclear cells |
| PCR | Polymerase ch |
| PD | Pharmacodynamic |
| PFS | Progression-free survival |
| PK | Pharmacokinetics |
| PLT | Platelet |
| PR | Partial remission |
| PT | Prothrombin time |
| PTT | Partial thromboplastin time |
| Q2W | Every two weeks |
| QD | Once a day |
| QW | Once weekly |
| QWx2 | Once a week for two weeks |
| QWx4 | Once a week for four weeks |
| RAEB | Refractory anemia with excess blasts |
| RBC | Red blood cell count |
| RFS | Relapse free survival |
| RP2D | Recommended Phase 2 dose |
| SAE | Serious adverse event |
| SAP | Statistical analysis plan |
| SC | Steering committee |
| SD | Standard deviation |
| SE | Standard error |
| SGOT | Serum glutamic oxaloacetic transaminase |
| SGPT | Serum glutamic pyruvic transaminase |
| SIRPα | Signal-regulatory protein alpha |
| SOP | Standard operating procedure |
| SRC | Safety review committee |
| SUSAR | Suspected unexpected serious adverse reaction |
| $t_{1/2}$ | Half-life |
| $t_{max}$ | Time to peak plasma concentration |
| TLS | Tumor lysis syndrome |
| TNBC | Triple-negative breast cancer |
| TNFα | Tumor necrosis factor alpha |
| ULN | Upper limit of normal |
| US | United States |
| USP | United States Pharmacopeia |
| $V_{SS}$ | Volume of distribution |
| WBC | White blood cell count |
| WHO | World Health Organization |
| Wks | Weeks |

Appendix B: RECIST Version 1.1

The following information is extracted/summarized from Eisenhauer, 2009, New Response Evaluation Criteria in Solid Tumors: Revised RECIST Guideline (Version 1.1). Please refer to the primary reference for further information.

Definitions

At screening, tumor lesions/lymph nodes are categorized as measurable or non-measurable.

Measurable Disease

Tumor Lesions. Must be accurately measured in at least one dimension (longest diameter in the plane of measurement is to be recorded) with a minimum size of: (a) 10 mm by CT scan (CT scan slice thickness no greater than 5 mm); (b) 10 mm caliper measurement by clinical exam (lesions which cannot be accurately measured with calipers should be recorded as non-measurable); and (c) 20 mm by chest X-ray.

Malignant Lymph Nodes

To be considered pathologically enlarged and measurable, a lymph node must be ≥15 mm in short axis when assessed by CT scan (CT scan slice thickness recommended to be no greater than 5 mm). At baseline and in follow-up, only the short axis will be measured and followed.

Non-Measurable Disease

All other lesions, including small lesions (longest diameter <10 mm or pathological lymph nodes with ≥10 to <15 mm short axis) as well as truly non-measurable lesions. Lesions considered truly non-measurable include: leptomeningeal disease, ascites, pleural or pericardial effusion, inflammatory breast disease, lymphangitic involvement of skin or lung, abdominal masses/abdominal organomegaly identified by physical exam that is not measurable by reproducible imaging techniques.

Tumor Response Evaluation

Target lesions: When more than one measurable tumor lesion is present at baseline all lesions up to a maximum of five lesions total (and a maximum of 2 lesions per organ) representative of all involved organs should be identified as target lesions and will be recorded and measured at baseline. Target lesions should be selected on the basis of their size (lesions with the longest diameter), be representative of all involved organs, but in addition should be those that lend themselves to reproducible repeated measurements. Note that pathological nodes must meet the measurable criterion of a short axis of ≥15 mm by CT scan and only the short axis of these nodes will contribute to the baseline sum. All other pathological nodes (those with short axis ≥10 mm but <15 mm) should be considered non-target lesions. Nodes that have a short axis <10 mm are considered non-pathological and should not be recorded or followed. At baseline, the sum of the target lesions (longest diameter of tumor lesions plus short axis of lymph nodes: overall maximum of 5) is to be recorded.

After baseline, a value should be provided on the eCRF for all identified target lesions for each assessment, even if very small. If extremely small and faint lesions cannot be accurately measured but are deemed to be present, a default value of 5 mm may be used. If lesions are too small to measure and indeed are believed to be absent, a default value of 0 mm may be used.

Non-target lesions: All non-measurable lesions (or sites of disease) plus any measurable lesions over and above those listed as target lesions are considered non-target lesions. Measurements are not required but these lesions should be noted at baseline and should be followed as "present," "absent." or "unequivocal progression."

Response Criteria: Target and non-target lesions are evaluated for response separately, and then the tumor burden as a whole is evaluated as the overall response:

Target Lesion Response:

Target lesions are assessed as follows: (1) Complete Response (CR). Disappearance of all target lesions. Any pathological lymph nodes (whether target or non-target) must have reduction in short axis to <10 mm; (2) Partial Response (PR). At least a 30% decrease in the sum of diameters of target lesions, taking as reference the baseline sum diameters; (3) Progressive Disease (PD). At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression); and (4) Stable Disease (SD). Neither sufficient shrinkage to qualify for PR nor sufficient increase to qualify for PD, taking as reference the smallest sum of diameters while on study.

Non-Target Lesion Response:

Non-target lesions will be assessed as follows: (1) Complete Response (CR). Disappearance of all non-target lesions and normalization of tumor marker level. All lymph nodes must be non-pathological in size (<10 mm short axis); (2) NonCR/Non-PD. Persistence of one or more non-target lesion(s) and/or maintenance of tumor marker level above the normal limits; and (3) Progressive Disease (PD). Unequivocal progression (see comments below) of existing non-target lesions. (Note: the appearance of one or more new lesions is also considered progression).

When the Subject Also Has Measurable Disease: In this setting, to achieve "unequivocal progression" on the basis of the non-target disease, there must be an overall level of substantial worsening in non-target disease such that, even in presence of SD or PR in target disease, the overall tumor burden has increased sufficiently to merit discontinuation of therapy. A modest "increase" in the size of one or more non-target lesions is usually not sufficient to quality for unequivocal progression status. The designation of overall progression solely on the basis of change in non-target disease in the face of SD or PR of target disease is therefore be extremely rare.

When the Subject Has Only Non-measurable Disease: This circumstance arises in some Phase 3 trials when it is not a criterion of study entry to have measurable disease. The same general concepts apply here as noted above; however, in this instance there is no measurable disease assessment to factor into the interpretation of an increase in non-measurable disease burden. Because worsening in non-target disease cannot be easily quantified (by definition: if all lesions are truly non-measurable) a useful test that can be applied when assessing subjects for unequivocal progression is to consider if the increase in overall disease burden based on the change in non-measurable disease is comparable in magnitude to the increase that would be required to declare PD for measurable disease: i.e., an increase in tumor burden representing an additional 73% increase in "volume" (which is equivalent to a 20% increase diameter in a measurable lesion). Examples include an increase in a pleural effusion from "trace" to "large," an increase in lymphangitic disease from localized to widespread, or may be described in protocols as "sufficient to require a change in therapy." If "unequivocal progression" is seen, the subject should be considered to have had overall PD at that point. Although it is ideal to have objective criteria to apply to non-measurable disease, the very nature of that disease makes it impossible to do so: therefore, the increase must be substantial.

Overall response should be assessed according to Table 7 for subjects with target lesions, and Table 8 for subjects with only non-target lesions:

TABLE 7

Time Point Response: Subjects with Target (±Non-target) Disease

| Target Lesions Response | Non-target Lesion Response | New Lesions | Overall Response |
|---|---|---|---|
| CR | CR | No | CR |
| CR | Non-CR/non-PD | No | PR |
| CR | Not evaluated | No | PR |
| PR | Non-PD or not all evaluated | No | PR |
| SD | Non-PD or not all evaluated | No | SD |
| Not all evaluated | Non-PD | No | NE |
| PD | Any | Yes or No | PD |
| Any | PD | Yes or No | PD |
| Any | Any | Yes | PD |

CR = complete response, PR = partial response, SD = stable disease, PD = progressive disease, NE = inevaluable.

TABLE 8

Time Point Response: Subjects with Non-target Disease Only

| Nontarget Lesions Response | New Lesions | Overall Response |
|---|---|---|
| CR | No | CR |
| Non-CR/non-PD | No | Non-CR/non-PDa |
| Not all evaluated | No | NE |
| Unequivocal PD | Yes or No | PD |
| Any | Yes | PD |

CR = complete response, PR = partial response, SD = stable disease, PD = progressive disease, NE = inevaluable.
aNon-CR/non-PD" is preferred over "stable disease" for nontarget disease since SD is increasingly used as endpoint for assessment of efficacy in some trials so to assign this category when no lesions can be measured is not advised.

Symptomatic Deterioration

Subjects with a global deterioration of health status requiring discontinuation of treatment without objective evidence of disease progression at that time should be reported as "symptomatic deterioration." Every effort should be made to document objective progression even after discontinuation of treatment. Symptomatic deterioration is not a descriptor of an objective response: it is a reason for stopping study therapy. The objective response status of such subjects is to be determined by evaluation of target and non-target disease.

Appendix C: Revised Response Criteria for Malignant Lymphoma

International Working Group Revised Response Criteria for Malignant Lymphoma (Cheson, 2007) can be accessed online at the "jco." "ascopubs" ".org" website using the specific URL "cgi/reprint/25/5/579" (click on "manual download for full text PDF of manuscript).

Appendix D: Performance Status Criteria

TABLE 9

Eastern Cooperative Oncology Group (ECOG) Performance Status (see Oken, 1982)

| Score | Description |
|---|---|
| 0 | Fully active, able to carry on all pre-disease performance without restriction |
| 1 | Restricted in physically strenuous activity but ambulatory and able to carry out work of alight or sedentary nature, e.g., light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

Appendix E: General Guidelines for Managing Hyperglycemia

Fasting glucose is defined as a level monitored ≥4 hr from the last meal for assessment of dose-limiting toxicity and clinical management decisions. Subjects should be instructed on how to recognize hypo- and hyperglycemia. Any subject who experiences hyperglycemia or symptoms associated with hyperglycemia is managed per standard of care with Compound A interruptions/reductions. Additional guidelines are described below: (a) In the event of persistent fasting hyperglycemia (>126 mg/dL or 14 mmol/L), or more or equal to Grade 2 or at any time considered appropriate by the Investigator, it is recommended that treatment with an oral anti-diabetic agent (OAD) be initiated; (b) In the event of Grade ≥3 fasting hyperglycemia, monitoring in the clinic should occur until the hyperglycemia resolves to Grade ≤2; (c) In the event of persistent Grade 3 fasting hyperglycemia (>250 mg/dL or 27.8 mmol/L), insulin therapy is considered either in conjunction with an OAD or alone. Long-acting insulin is used only when the subject is hospitalized. Monitoring of glucose continues for at least 6 hr following administration of insulin (fast- or long-acting) due to possible rebound effects. The medical monitor is notified; (d) In the event of a Grade 4 fasting blood glucose (>50 mg/dL or 27.8 mmol/L), Compound A is withheld while insulin therapy is initiated. The medical monitor is notified. Treatment interruptions of >4 weeks necessitates removal of the subject from this study; and (e) At the discretion of the Investigator, daily home monitoring via finger-stick testing (while fasting in the AM) may be initiated. Subjects are provided a glucometer and trained how to perform finger-stick testing and document results in a diary card which is reviewed during each clinic visit. They are instructed how to contact study staff immediately in the event of a high fasting glucose result (>160 mg/dL or 8.9 mmol/L), in which case prompt assessment in the clinic is necessary; or call clinic and specify in clinic visit if grade 3 or higher. The opinion of an endocrinologist regarding adequate management of the subject may be advisable in such cases.

Glucophage, and other biguanide therapy, should be temporarily suspended when planned radiological tumor assessments (e.g., CT scan) involves iodinated contrast. Goldberg, 2005; and Turina, 2006 are suggested resources for hyperglycemia management.

Appendix G: Management of Biologic Specimens (Addendum to Laboratory Manual)

Sample Handling and Storage: All blood and tissue samples collected for biomarker and genetic research as part of this study that are not depleted following analysis will be stored for use in research for up to 5 yrs after the study is completed. With subject consent, the storage period will be extended to 20 yrs after the study is completed for use in future research to learn more about cancer and other diseases. Samples are stored in a secure laboratory facility designed for long term sample storage, with appropriate access control, monitoring and back-up systems.

Sample Coding: All biomarker and genetic research samples will be identified only by a code (subject identification number). These samples will not have any other personal information on them. The study doctor keeps the code key. The samples and the code key are kept confidential and separate. Researchers who perform tests on samples see only the code and do not see any information that specifically identifies the subject.

Research on Blood & Tissue Samples: Biomarker and genetic research samples are tested by the sponsor or by companies contracted by the sponsor to determine the effects Compound A has on the subject and subject's cancer. This includes determining if biomarkers in blood cells or tumor cells demonstrate that Compound A is biologically active. Additionally, DNA samples from whole blood and tumor tissue are analyzed for genetic changes that may correlate with the subject's response to the drug.

Reporting and Availability of Biomarker and Genetic Results: Biomarker and genetic research sample test results are not shared with the subject, insurance companies, nor any other third parties not involved in the sample analysis described above. The results are not filed in the subject's medical records. Test results are for research purposes only and are not used to make decisions about a subject's routine medical care.

Names of subjects and identifiers will not be mentioned in publications or reports, thereby minimizing the possibility of psychological or social risks that could arise from knowledge of this biomarker and genetic information, such as risk for employability or insurability or the risk of discrimination.

Mechanism to Request Sample Destruction upon Withdrawal of Consent: If subjects withdraw consent to participate in the study, they may additionally request to have their biomarker and genetic research samples destroyed. In such cases, a subject informs the study doctor that consent has been withdrawn and request to have any stored, unused samples destroyed. Any unused samples will then be destroyed by the sponsor. If samples were analyzed before consent was withdrawn, however, then the sponsor may still use data already available.

If subjects agree to allow biomarker and genetic research samples to be kept 20 yrs for future research, they are also free to reverse just that decision at any time. The subject will inform the study doctor that permission has been withdrawn for samples to be used for future research. Any unused samples will then be destroyed by the sponsor. If samples were analyzed before consent was withdrawn, however, then the sponsor may still use data already available.

Appendix H: Characteristics of the Bayesian Logistic Regression Model

An adaptive Bayesian logistic regression model (BLRM. Neuenschwander, et al., 2008) for dose escalation with overdose control (EWOC, Babb et al 1988) may be used to guide dose escalation in this study.

This Appendix presents performance metrics (operating characteristics) that illustrate the precision of the design in estimating the MTD under various dose-toxicity relationships through computer simulation. In addition, recommendations of the next dose level by BLRM with overdose-control principle are provided under various hypothetical outcome scenarios in early cohorts (assuming three evaluable patients in each cohort for simplicity) to show how it facilitates on-study dose-escalation decisions.

Figure 6:
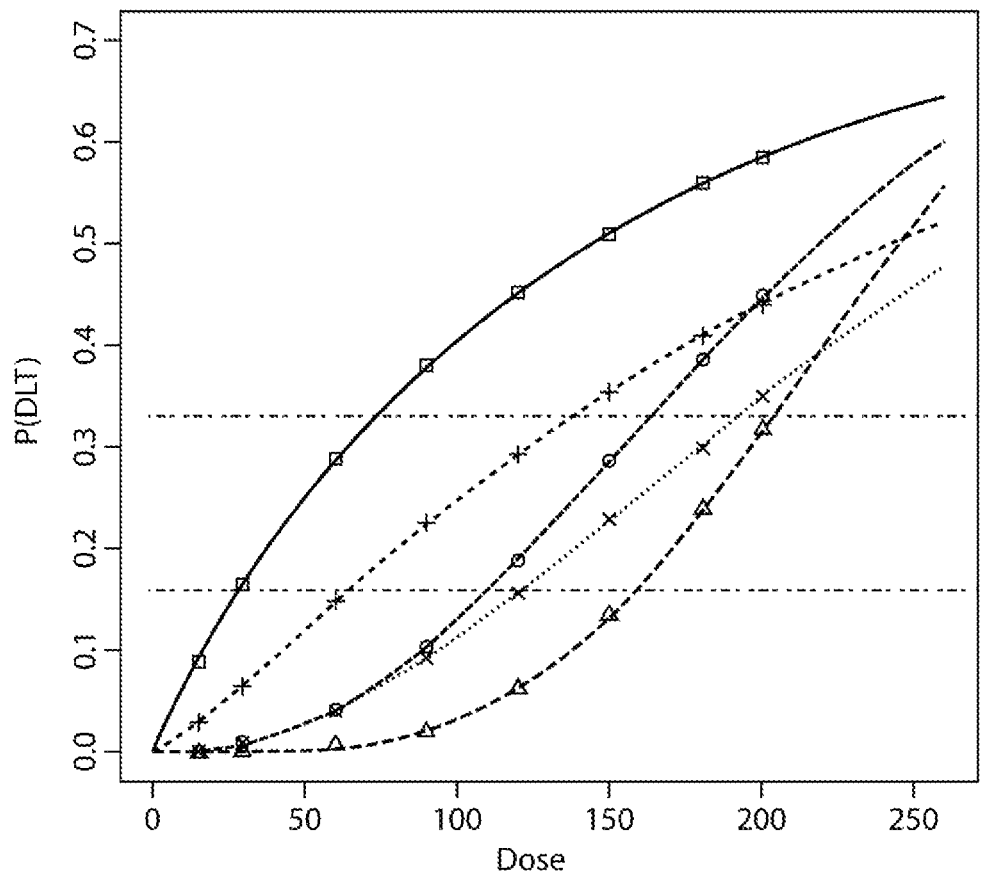
FIG. 6 shows dose toxicity curves useful for simulation.

Regarding specifications and results of simulation study, operating characteristics that illustrate the precision of the design in estimating the MTD under various assumed true dose-toxicity relationships can be envisioned. Simulations (see FIG. 6) are performed for the BLRM under five scenarios of true dose-DLT relationship: (a) Dose-DLT relationship is a steep curve and MTD is reached at early dose level (SE); (b) Dose-DLT relationship is a steep curve and MTD is reached at middle dose level (SM); (c) Dose-DLT relationship is a steep curve and MTD is reached at late dose level (SL); (d) Dose-DLT relationship is a flat curve and MTD is reached at middle dose level (FM); and (e) Dose-DLT relationship is a flat curve and MTD is reached at late dose level (FL)

TABLE 10

P(DLT) for five simulated scenarios

| Scenario | P(DLT) at different dose level (mg) | | | | | | | |
|---|---|---|---|---|---|---|---|---|
| | 15 | 30 | 60 | 90 | 120 | 150 | 180 | 200 |
| SE | 0.0879 | 0.1647 | 0.2874 | 0.3800 | 0.4520 | 0.5094 | 0.5563 | 0.5829 |
| SM | 0.0015 | 0.008 | 0.0418 | 0.1045 | 0.1901 | 0.2874 | 0.3857 | 0.4478 |
| SL | 0.000 | 0.0004 | 0.0049 | 0.0224 | 0.0635 | 0.1362 | 0.2389 | 0.3184 |
| EM | 0.0295 | 0.0677 | 0.1477 | 0.2239 | 0.2928 | 0.3539 | 0.4079 | 0.4402 |
| FL | 0.0026 | 0.0106 | 0.0428 | 0.0935 | 0.1574 | 0.2284 | 0.3013 | 0.3490 |

Operating characteristics are reviewed to investigate overall performance of the BLRM under each true scenario. Table 11 summarizes the results from the simulations performed:

TABLE 11

Summary metrics of simulation for BLRM and comparison with 3 + 3

| Scenario/ Method | Mean # subjects | Proportion of subjects with DLT | Probability of recommending a dose with true P(DLT) | | |
|---|---|---|---|---|---|
| | | | 0.16-0.33 | ≥0.33 | <0.16 |
| SE, N-CRM | 20.14 | 0.23 | 0.73 | 0.13 | 0.15 |
| SE, 3 + 3 | 15.35 | 0.23 | 0.60 | 0.11 | 0.29 |
| SM, N-CRM | 24.20 | 0.13 | 0.68 | 0.10 | 0.22 |
| SM, 3 + 3 | 23.76 | 0.13 | 0.53 | 0.12 | 0.35 |
| SL, N-CRM | 26.33 | 0.10 | 0.53 | 0.00 | 0.47 |
| SL, 3 + 3 | 26.81 | 0.09 | 0.51 | 0.00 | 0.49 |
| FM, N-CRM | 22.90 | 0.16 | 0.51 | 0.11 | 0.38 |
| FM, 3 + 3 | 20.26 | 0.17 | 0.39 | 0.12 | 0.49 |
| FL, N-CRM | 25.13 | 0.12 | 0.48 | 0.14 | 0.47 |
| FL, 3 + 3 | 24.77 | 0.12 | 0.42 | 0.11 | 0.53 |

Overall the BLRM model with specified prior is performing reasonably. With similar or a little more sample size, BLRM model can select MTD in the target range with higher probability, especially for scenarios (a), (b), and (d).

Regarding the hypothetical dose escalation scenarios in early cohorts, aside from the overall operating characteristics studied above, the design should make reasonable decisions during a study based on the observed toxicities. After completion of a given cohort, the decision to dose escalate and actual dose chosen for the subsequent cohort will depend on the recommendation of the BLRM per EWOC principle and medical review of available clinical and laboratory data.

Some scenarios to illustrate the dose escalation up to the third dose cohort are listed in Table 12 using the 2-parameter BLRM. It is assumed that each cohort has at least 3 evaluable patients. If any patient experiences a DLT, the dose increase will be no greater than 50% for any subsequent dose escalation. The BLRM model is performing reasonably for the hypothetical dose escalation scenarios.

TABLE 12

Possible scenarios up to the third cohort with three patients per cohort

| Scenario | Dose History (mg) | #DLT/#Pat | Next dose by N-CRM(mg) |
|---|---|---|---|
| 1 | 15 | 0/3 | 30 |
| 2 | 15 | 0/3 | 30 |
| | 30 | 0/3 | 60 |
| 3 | 15 | 0/3 | 30 |
| | 30 | 1/3 | 30 |
| 4 | 15 | 0/3 | 30 |
| | 30 | 2/3 | 15 |
| 5 | 15 | 0/3 | 30 |
| | 30 | 0/3 | 60 |
| | 60 | 0/3 | 90 |
| 6 | 15 | 0/3 | 30 |
| | 30 | 0/3 | 60 |
| | 60 | 1/3 | 60 |

The Bayesian Logistic Regression Model enables us to incorporate the pre-clinical information, as well as to update the recommended dose based on all safety data in the study. By reviewing the metrics presented in the table, it can be seen that the model is not sensitive to different scenarios of truth. In general, this model is conservative due to the overdose control criteria. In all scenarios, the probabilities of recommending a dose with true P(DLT)≥33% as MTD are much smaller than probabilities of recommending a dose with true P(DLT) between 16%-33% as MTD.

On-study recommendations based on the model are consistent with the clinical decision making process, and should be considered in conjunction with other available clinical information by the Sponsor Clinical Trial Team and Study investigators in deciding the dose levels to be tested in order to determine the MTD.

Example 13. Synergistic Effects of Compound A and Histone Deacetylase (HDAC) Inhibitor Romidepsin in a Pancreatic Xenograft PA0165 Mouse Mode The BET Bromodomain Protein BRD4 has been implicated in the regulation of the metabolic pathways in the pancreas. The expression of BRD4 is significantly upregulated in pancreatic ductal adenocarcinoma cell lines, compared to that in human pancreatic duct epithelial cells. Furthermore, studies show that BRD4 promotes pancreatic ductal adenocarcinoma cell proliferation and enhances resistance to some chemotherapeutic agents, such as gemcitabine. Therefore, BRD4 inhibition has promise for pancreatic cancer treatments. This led to an efficacy in vivo experiment to understand whether Compound A-mediated BRD4 inhibition could sensitize the pancreatic tumor cells to the treatment of HDAC inhibitor Romidepsin.

Figure 8:
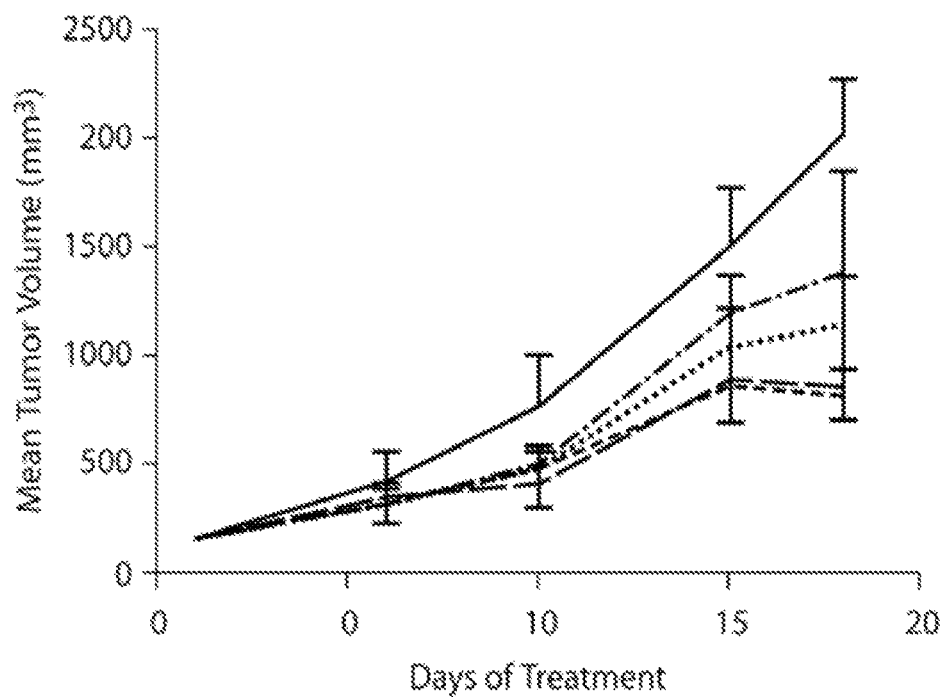
FIG. 8 is a graph showing tumor growth inhibition of PA0165 xenografts by administration of either Compound A. Romidepsin, or a combination of Compound A and Romidepsin. 3/4 is 3 days on and 4 days off; Q4D is once every 4 days; Q7D is once every 7 days; —— Control; - - - - Compound A 25 mg/kg, 3/4; - —— - —— Romidepsin 1.5 mg/kg Q4D×3; —— —— Compound A 25 mg/kg. 3/4 combined with Romidepsin 1.5 mg/kg Q7D; - - - Compound A 25 mg/kg, 3/4 combined with Romidepsin 0.75 mg/kg Q7D. Tumor volumes were plotted as mean±standard error of the mean (SEM).

Cohorts of 4-6 wk-old NSG mice bearing PA0165 were treated with Romidepsin at 1.5 mg/kg intravenous (IV)×3 Q4D; Compound A 25 mg/kg orally QD 3 days on then 4 days off; or with a combination of Compound A 25 mg/kg orally QD 3 days on then 4 days off and Romidepsin at 1.5 or 0.75 mg/kg IV Q7D. The treatment lasted 21 days. Significant tumor growth inhibitions, as measured by tumor volumes, were observed for all treatment groups (FIG. 8). Romidepsin alone induced significant TGI of 45%. Compound A alone induced significant TGI of 38%. The combination of Compound A and Romidepsin demonstrated synergy, and was significantly superior to all other regimens in terms of TGI (68% with Compound A in combination with 1.5 mg/kg Romidepsin; 65% with Compound A in combination with 0.75 mg/kg Romidepsin).

Figure 9:
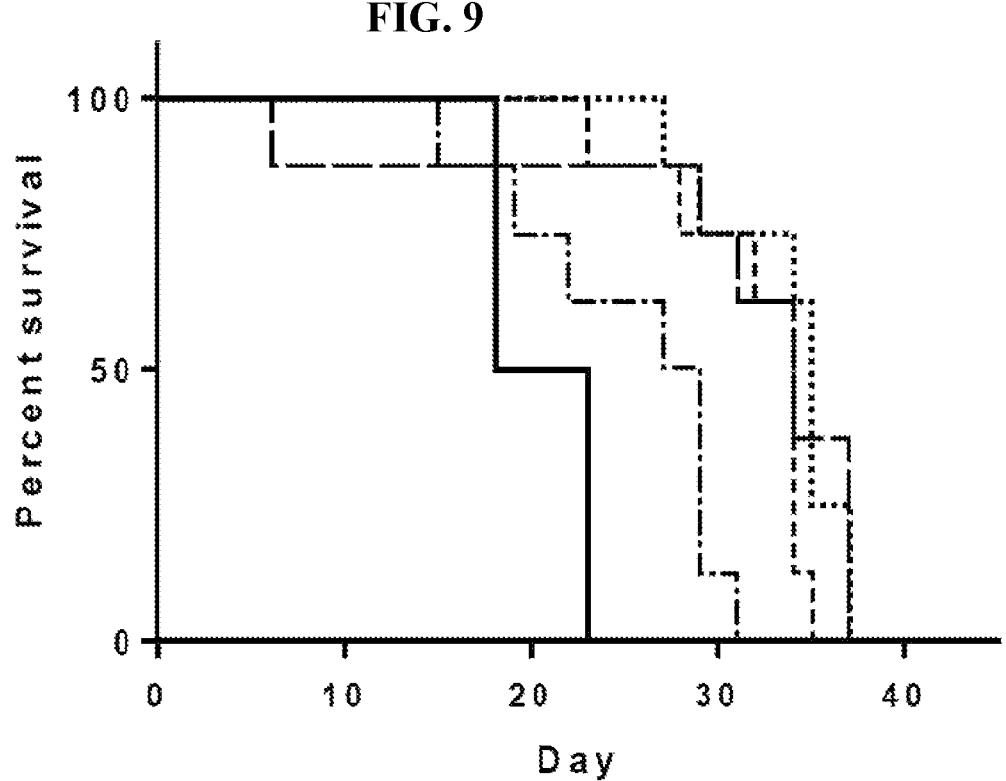
FIG. 9 is a graph showing survival curve of PA0165 xenografts by administration of either Compound A. Romidepsin, or a combination of Compound A and Romidepsin. 3/4 is 3 days on and 4 days off; Q4D is once every 4 days. —— Control; - - - - Compound A at 25 mg/kg, 3/4; - —— - —— Romidepsin 1.5 mg/kg Q4D×3; —— —— Compound A 25 mg/kg, 3/4 combined with Romidepsin 1.5 mg/kg Q7D; - - - Compound A 25 mg/kg, 3/4 combined with Romidepsin 0.75 mg/kg Q7D.

All treatment groups lost substantial weight between day 10 and day 15, and then recovered. Compound A only or combination treatment groups display significantly greater survival rate than the Romidepsin only treatment group (FIG. 9). At day 30 following initial treatment, the survival rate for the Romidepsin only treatment group was about 10%. In contrast, the survival rates for the Compound A only or combination treatment groups were about 70%. There was no significant difference in the survival rate between the Compound A only and combination treatment groups.

Example 14. Synergistic Effects of Compound A and Abraxane (Protein-Bound Paclitaxel) in a Pancreatic Xenograft PA0165 Mouse Model The BET Bromodomain Protein BRD4 has been implicated in the regulation of the metabolic pathways in the pancreas. The expression of BRD4 is significantly upregulated in pancreatic ductal adenocarcinoma cell lines, compared to that in human pancreatic duct epithelial cells. Furthermore, studies show that BRD4 promotes pancreatic ductal adenocarcinoma cell proliferation and enhances resistance to some chemotherapeutic agents, such as gemcitabine. Therefore. BRD4 inhibition has promise for pancreatic cancer treatments. This led to an efficacy in vivo experiment to understand whether Compound A-mediated BRD4 inhibition could sensitize the pancreatic tumor cells to the treatment of protein-bound paclitaxel Abraxane.

Figure 10:
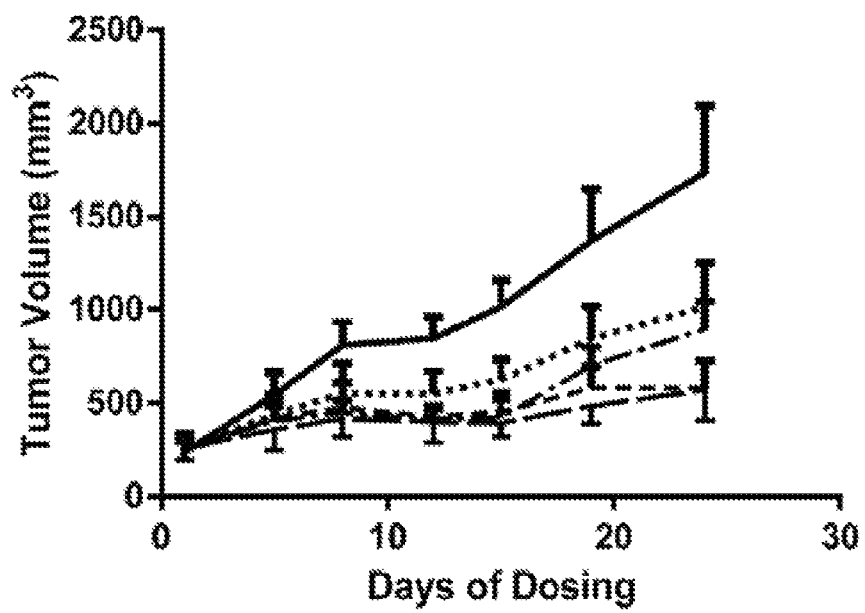
FIG. 10 is a graph showing tumor growth inhibition of PA0165 xenografts by administration of either Compound A. Abraxane, or a combination of Compound A and Abraxane. —— Control; - - - - Compound A 25 mg/kg; - —— - —— Abraxane 10 mg/kg; —— —— Compound A 25 mg/kg combined with Abraxane 10 mg/kg; - - - Compound A 12.5 mg/kg combined with Abraxane 10 mg/kg. Tumor volumes were plotted as mean±standard error of the mean (SEM).
Figure 11:
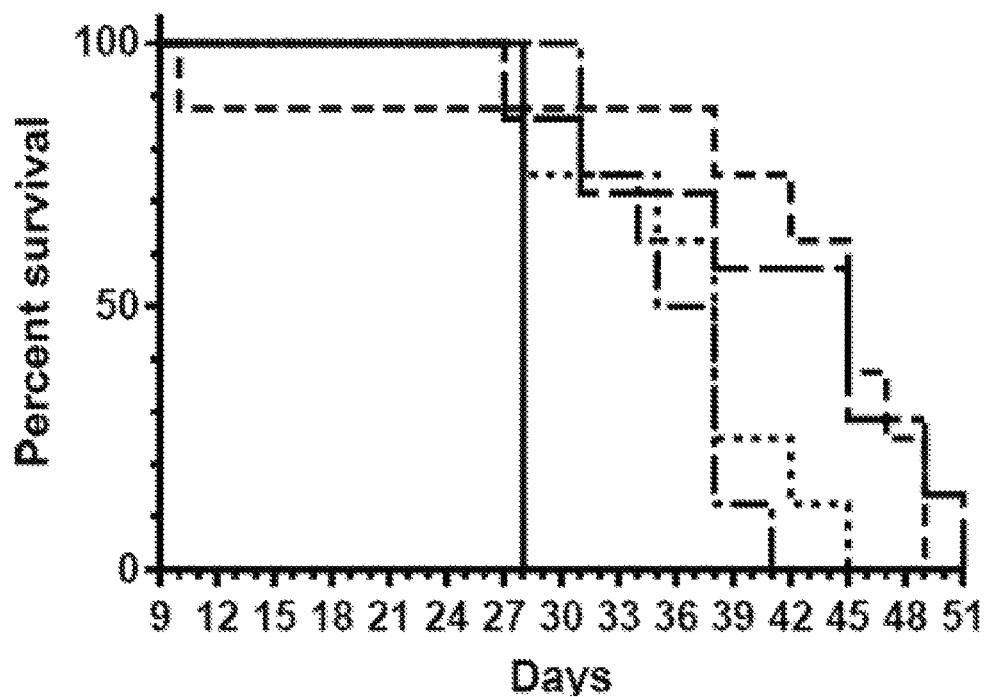
FIG. 11 is a graph showing survival curve of PA0165 xenografts by administration of either Compound A, Abraxane, or a combination of Compound A and Abraxane. —— Control; - - - - Compound A 25 mg/kg; - —— - —— Abraxane 10 mg/kg; —— —— Compound A 25 mg/kg combined with Abraxane 10 mg/kg; - - - Compound A 12.5 mg/kg combined with Abraxane 10 mg/kg.

Cohorts of NSG mice bearing PA0165 were treated with Abraxane 10 mg/kg, IV×3 Q4D; Compound A 25 mg/kg orally QD 3 days on then 4 days off; or with a combination of Abraxane 10 mg/kg iv Q7D and Compound A 25 or 12.5 mg/kg orally QD 3 days on then 4 days off. The treatment lasted 21 days. Significant tumor growth inhibitions, as measured by tumor volumes, were observed for all treatment groups (FIG. 10). Abraxane alone induced significant TGI of 55%. Compound A alone induced significant TGIs of 49.3%. The combination of Compound A and Abraxane demonstrated synergy, and was significantly superior to all other regimens in terms of TGI (78.1% with Abraxane in combination with 25 mg/kg Compound A; 79.1% with Abraxane in combination with 12.5 mg/kg Compound A). Moderate weight loss was observed during part of the study course in all groups; Body weight loss observed in larger tumor bearing mic. The combination treatment groups displayed significantly greater survival rates compared to the individual treatment groups (FIG. 11). At day 41 following the initial treatment, the survival rate for Abraxane only treatment group was 0% and for Compound A only treatment group was about 20%. In contrast, the survival rate for the combination groups was about 60% with the treatment of Abraxane in combination with 25 mg/kg Compound A and 70% with Abraxane in combination with 12.5 mg/kg Compound A, respectively.

We claim:

1. A method for treating cancer or neoplastic disease comprising administering to a human patient a therapeutically effective amount of:
   (i) at least one bromodomain and extra-terminal protein (BET) inhibitor; and
   (ii) at least one chemotherapeutic agent, which does not inhibit BET directly, wherein the BET inhibitor has the structure of Formula I, or a pharmaceutically acceptable salt thereof,

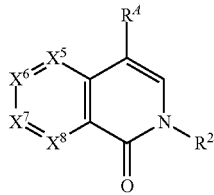

Formula I wherein:
   $R^2$ is $CH_3$, $CH_2CH_3$, $CH_2CF_3$, $CH_2F$, $CHF_2$, $CF_3$, $CH_2D$, $CHD_2$, or $CD_3$;
   $X^5$ is C—$R^5$, wherein:
      $R^5$ is hydrogen, halogen, OH, CN, $OR^{61}$, $NHR^{61}$, $N(R^{61})_2$, alkyl, cycloalkyl, cycloalkylalkyl, aryl, aralkyl, heterocyclyl, heterocyclylalkyl, heteroaryl, or heteroarylalkyl, in which
         each $R^{61}$ is independently selected from alkyl, cycloalkyl, cycloalkylalkyl, aryl, aralkyl, heterocyclyl, heterocyclylalkyl, heteroaryl, or heteroarylalkyl;

$X^6$ is C—$R^6$, wherein:
   $R^6$ is hydrogen, halogen, OH, CN, alkyl, cycloalkyl, cycloalkylalkyl, amino, alkylamino, dialkylamino, cycloalkylalkylamino, alkoxy, or cycloalkylalkoxy;
$X^7$ is C—$R^7$, wherein:
   $R^7$ is hydrogen, halogen, OH, CN, $OR^{61}$, $NHR^{61}$, $N(R^{61})_2$, alkyl, cycloalkyl, cycloalkylalkyl, aryl, aralkyl, heterocyclyl, heterocyclylalkyl, heteroaryl, or heteroarylalkyl;
$X^8$ is C—$R^8$, wherein
   $R^8$ is hydrogen, halogen, or alkyl; and
$R^A$ is

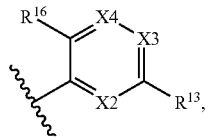

wherein:
   $X^2$ is or C—$R^{12}$, wherein $R^{12}$ is hydrogen, halogen, alkyl, or alkoxy;
   $R^{13}$ is Y—Z, wherein
      Y is selected from a bond, $CH_2$, $CH(C_1$-$C_4$ alkyl); and
      Z is selected from $SO_2R^{21}$, $N(R^{22})SO_2R^{21}$, $SO_2N(R^{22})_2$, $N(R^{22})SO_2N(R^{22})_2$, $CON(R^{22})_2$, $N(R^{22})CO_2R^{21}$, $N(R^{22})CON(R^{22})_2$, $N(R^{22})COR^{21}$, $COR^{21}$, $OC(O)N(R^{22})_2$, $OSO_2N(R^{22})_2$, or $N(R^{22})SO_3R^{21}$; wherein
         each $R^{21}$ is independently selected from alkyl, cycloalkyl, cycloalkylalkyl, aryl, aralkyl, heterocyclyl, heterocyclylalkyl, heteroaryl, or heteroarylalkyl; and
         each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl;
   $X^3$ is C—$R^{14}$, wherein $R^{14}$ is hydrogen, halogen, —CN, alkyl, cycloalkyl, or alkoxy; and
   $X^4$ is C—$R^{15}$, wherein $R^{15}$ is hydrogen, halogen, alkyl, CN, or alkoxy; and
   $R^{16}$ is hydrogen, halogen, or W—X, wherein
      W is a bond, O, or S, and
      X is selected from alkyl, aryl, aralkyl, cycloalkyl, cyclo-alkylalkyl, alkynyl, cycloalkylalkynyl, heterocyclyl, heterocyclylalkyl, heteroaryl or heteroarylalkyl;
wherein the chemotherapeutic agent is selected from the group consisting of temozolomide, romidepsin, and protein-bound paclitaxel, wherein the BET inhibitor is present in an amount to enhance the therapeutic effect of the chemotherapeutic agent, and the cancer or neoplastic disease is selected from the group consisting of non-Hodgkin's lymphoma, leukemia, non-small cell lung cancer, pancreatic cancer, breast cancer, NUT carcinoma, and medulloblastoma.

2. The method of claim 1, wherein administering the BET inhibitor and the chemotherapeutic agent results in a synergistic reduction in cell proliferation in a tumor of the patient, or a synergistic increase in apoptosis in a tumor of the patient, as compared with administration of either the BET inhibitor or the chemotherapeutic agent alone.

3. The method of claim 1, wherein the therapeutic effective amount for both the BET inhibitor and chemotherapeutic agent when administered together can be at least 50% lower than that when the BET inhibitor and chemotherapeutic agent are used individually.

4. The method of claim 1, wherein the chemotherapeutic agent is temozolomide.

5. The method of claim 1, wherein the chemotherapeutic agent is romidepsin.

6. The method of claim 1, wherein the chemotherapeutic agent is protein-bound paclitaxel.

7. The method of claim 1, wherein the cancer or neoplastic disease is non-Hodgkin's lymphoma.

8. The method of claim 1, wherein the cancer or neoplastic disease is leukemia.

9. The method of claim 1, wherein the cancer or neoplastic disease is non-small cell lung cancer.

10. The method of claim 1, wherein the cancer or neoplastic disease is pancreatic cancer.

11. The method of claim 1, wherein the cancer or neoplastic disease is breast cancer.

12. The method of claim 1, wherein the cancer or neoplastic disease is NUT carcinoma.

13. The method of claim 1, wherein the at least one bromodomain and extra-terminal protein (BET) inhibitor is 4-[2-(cyclopropylmethoxy)-5-methylsulfonylphenyl]-2-methylisoquinolin-1-one or the pharmaceutically acceptable salt thereof.

14. The method of claim 1, wherein the cancer is temozolomide-resistant.

15. The method of claim 1, wherein the cancer or neoplastic disease is medulloblastoma.

* * * * *

UNITED STATES PATENT AND TRADEMARK OFFICE
CERTIFICATE OF CORRECTION

| | | |
|---|---|---|
| PATENT NO. | : 11,464,771 B2 | Page 1 of 1 |
| APPLICATION NO. | : 17/033311 | |
| DATED | : October 11, 2022 | |
| INVENTOR(S) | : Robert Cho and Jeffrey Alan Stafford | |

It is certified that error appears in the above-identified patent and that said Letters Patent is hereby corrected as shown below:

On the Title Page

Under Other Publications:
Column 2, Line 19, "iantitumor" should be replaced with -- antitumor --

In the Claims

Column 90, Line 23, In Claim 1, "$X^2$ is or C-$R^{12}$" should read -- $X^2$ is C-$R^{12}$ --

Signed and Sealed this
Twenty-eighth Day of March, 2023

*Katherine Kelly Vidal*

Katherine Kelly Vidal
*Director of the United States Patent and Trademark Office*